(12) United States Patent
Hsieh et al.

(10) Patent No.: US 11,427,846 B2
(45) Date of Patent: Aug. 30, 2022

(54) SYSTEM AND METHOD FOR NUCLEIC ACID LIBRARY PREPARATION VIA TEMPLATE SWITCHING MECHANISM

(71) Applicant: Kapa Biosystems, Inc., Wilmington, MA (US)

(72) Inventors: Jennifer Hsieh, Cape Town (ZA); Paul McEwan, Diablo, CA (US); Martin Ranik, Santa Clara, CA (US); Marliz Strydom, Cape Town (ZA); Eric van der Walt, Cape Town (ZA); Ross Wadsworth, Cape Town (ZA)

(73) Assignee: Kapa Biosystems, Inc., Wilmington, MA (US)

( * ) Notice: Subject to any disclaimer, the term of this patent is extended or adjusted under 35 U.S.C. 154(b) by 104 days.

(21) Appl. No.: 16/892,541

(22) Filed: Jun. 4, 2020

(65) Prior Publication Data
US 2020/0291440 A1 Sep. 17, 2020

Related U.S. Application Data

(63) Continuation of application No. PCT/US2018/064227, filed on Dec. 6, 2018.

(60) Provisional application No. 62/595,393, filed on Dec. 6, 2017.

(51) Int. Cl.
*C12P 19/34* (2006.01)
*C12Q 1/6853* (2018.01)
*C12Q 1/686* (2018.01)

(52) U.S. Cl.
CPC .............. *C12P 19/34* (2013.01); *C12Q 1/686* (2013.01); *C12Q 1/6853* (2013.01); *C12Y 207/07007* (2013.01); *C12Y 207/07049* (2013.01)

(58) Field of Classification Search
None
See application file for complete search history.

(56) References Cited

U.S. PATENT DOCUMENTS 9,410,173 B2   8/2016   Betts et al.

FOREIGN PATENT DOCUMENTS

WO   2014/066179 A1   5/2014
WO   2015/094861 A1   6/2015

OTHER PUBLICATIONS

Turchinovich et al., "Capture and Amplification by Tailing and Switching (CATS)," RNA Biol. 2014, 11(7):817-828. (Year: 2014).*

(Continued)

*Primary Examiner* — Kaijiang Zhang
(74) *Attorney, Agent, or Firm* — Eric Grant Lee

(57) ABSTRACT

The disclosure provides a composition comprising a double-stranded deoxyribonucleic acid (dsDNA) sequence comprising from 5' to 3', a sequence comprising a first adaptor sequence, a template sequence, and a second adaptor sequence, wherein the second adaptor sequence comprises a hybridization site for a template switching oligonucleotide (TSO). The disclosure provides methods for making the compositions of the disclosure using a template switching mechanism to add non-templated basepairs to the ends of a DNA molecule, hybridize a TSO to the non-templated basepairs, and then extend the sequence complementary to the TSO to add an adaptor.

50 Claims, 34 Drawing Sheets
(6 of 34 Drawing Sheet(s) Filed in Color)
Specification includes a Sequence Listing.

(56) References Cited

OTHER PUBLICATIONS

International Search Report for International Patent Application No. PCT/US2018/064227 (dated Jun. 13, 2019).
Written Opinion of the International Searching Authority for International Patent Application No. PCT/US2018/064227 (dated Jun. 13, 2019).
Integrated DNA Technologies, "Use of template switching oligos (TS oligos, TSOs) for efficient cDNA library construction," (Mar. 8, 2017).
Kapteyn, et al., "Incorporation of non-natural nucleotides into template-switching oligonucleotides reduces background and improves cDNA synthesis from very small RNA samples," BMC Genomics 11:413 (2010).
Lopes Pinto & Lindblad, "A guide for in-house design of template-switch-based 5' rapid amplification of cDNA ends systems," Analytical Biochemistry 397:227-232 (2010).
Tang, et al., "Suppression of artifacts and barcode bias in high-throughput transcriptome analyses utilizing template switching," Nucleic Acid Research 41(3):e44 (2013).
Turchinovich, et al., "Capture and Amplification by Tailing and Switching (CATS): An ultrasensitive ligation-independent method for generation of DNA libraries for deep sequencing from picogram amounts of DNA and RNA," RNA Biology 11(7):817-828 (2014).

\* cited by examiner

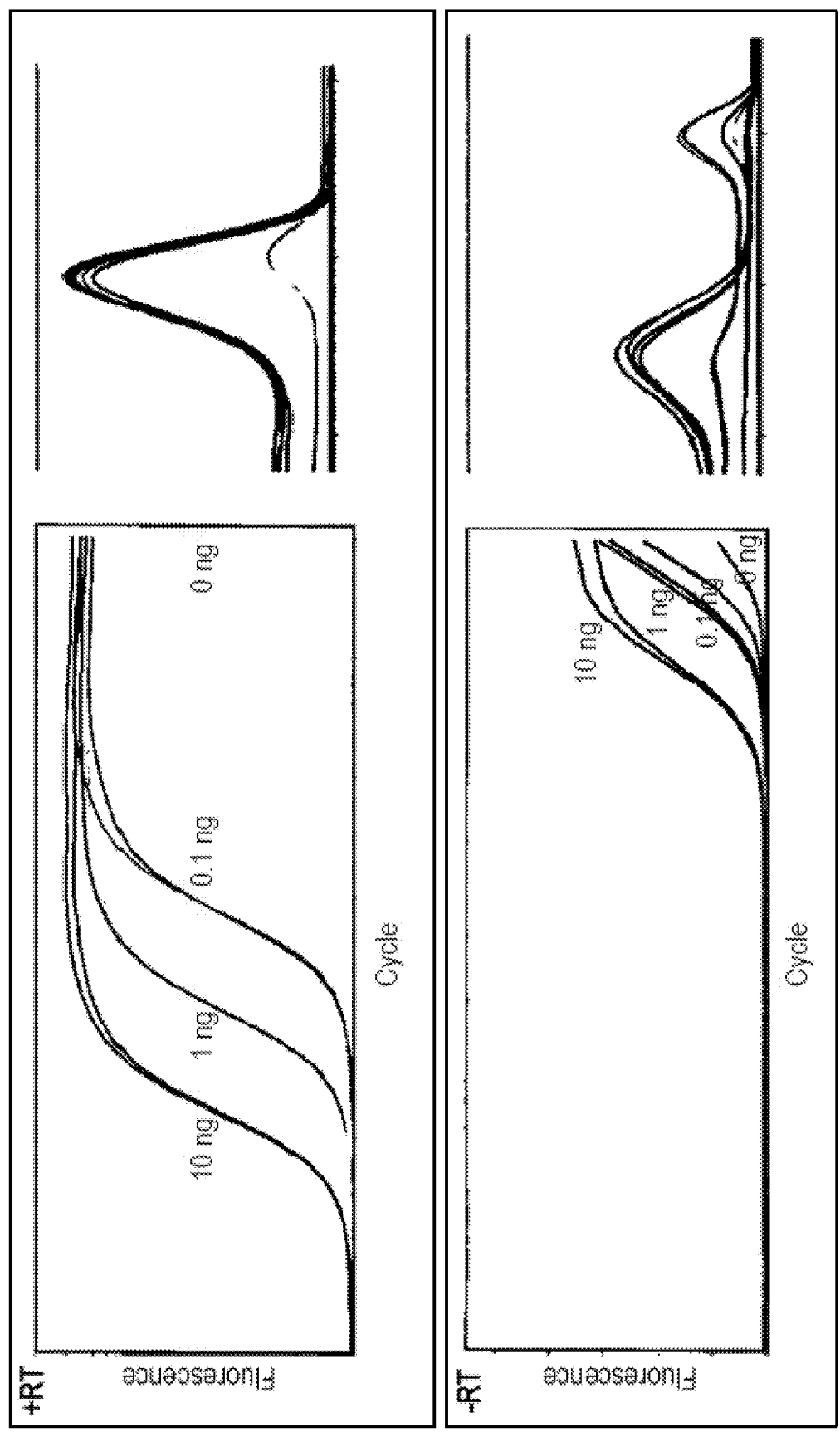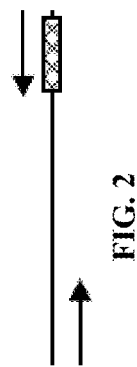
FIG. 2

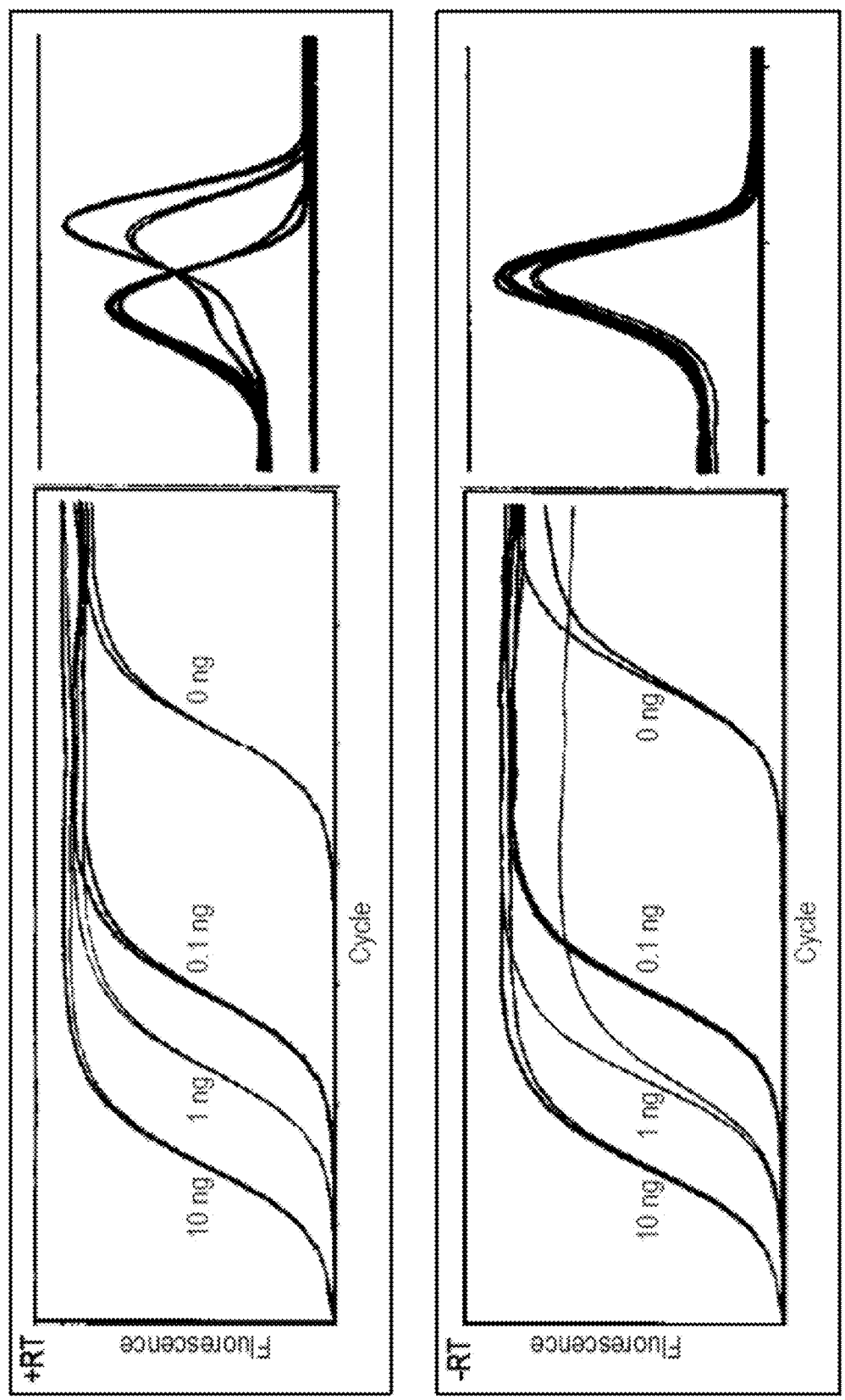
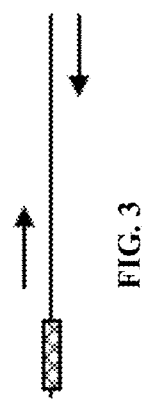
FIG. 3

SEQUENCE LISTING

<160> NUMBER OF SEQ ID NOS: 14

<210> SEQ ID NO 1
<211> LENGTH: 2337
<212> TYPE: DNA
<213> ORGANISM: Artificial Sequence
<220> FEATURE:
<223> OTHER INFORMATION: synthetic sequence

<400> SEQUENCE: 1

| | | | | | |
|---|---|---|---|---|---|
| atggctagcg | ccattctgga | taccgactat | atcacggaag | atggcaaacc | ggtgatacgt | 60 |
| atttttaaga | aagagaatgg | tgagttcaaa | atcgagtacg | accgcacttt | tgagccatat | 120 |
| ttctacgcgt | tactgaagga | cgatagcgcc | attgaagaag | ttaaaaaaat | caccgcagag | 180 |
| cggcatggga | cagtggtaac | cgtgaagaga | gttgaaaaag | tccagaaaaa | attttttggga | 240 |
| cgacctgtag | aagtgtggaa | actttatttc | actcaccccc | aagatgttcc | ggctatacgt | 300 |
| gataaaattc | gcgaacatcc | agcggtcatt | gatatttacg | aatatgatat | accttttgcc | 360 |
| aagcgttacc | tcatcgacaa | aggcctggtg | ccgatggaag | gtgatgaaga | attaaaaatg | 420 |
| ttggcattcg | acattgaaac | actttatcac | gaggggaag | agtttgctga | gggtcccatc | 480 |
| ctgatgattt | cttatgcgga | tgaagagggt | gcccgcgtaa | taacctggaa | gaacgttgat | 540 |
| ctcccgtacg | tggacgtcgt | tagtacgaaa | cgggaaatga | tcaaacgttt | cctgcgcgta | 600 |
| gtgaaagaga | aagatccaga | cgtcttaatt | acctataatg | gtgataactt | tgattttgca | 660 |
| tacctgaaaa | aagatgcga | aaagttgggc | ataaatttcg | ctcttggtcg | agacgggtca | 720 |
| gagcctaaaa | tccagcgtat | gggagatcgc | tttgcggttg | aagtgaaagg | ccggattcat | 780 |
| ttcgacctgt | atccggtaat | tcgtcgcact | atcaacctcc | ccacatacac | gttagaagcc | 840 |
| gtctatgagg | cagtttttgg | tcaaccgaag | gaaaaagttt | acgctgagga | aattaccact | 900 |
| gcgtgggaaa | caggcgagaa | tctggaacgt | gtagcccgct | attctatgga | ggatgcaaaa | 960 |
| gttacctatg | aattgggtaa | ggaatttctt | ccaatggagg | cgcagctgag | tcgtttagtc | 1020 |
| ggacaacctc | tgtgggacgt | ttcacgctcc | tcgactggca | atctcgtgga | gtggttcctg | 1080 |
| ttgagaaaag | cctatgaacg | aaacgaagta | gcaccgaata | accaagcga | ggaagaatat | 1140 |
| cagcgtcgcc | ttcgcgagtc | ttacacaggt | gggtttgtta | aggaaccgga | gaaaggtctt | 1200 |
| tgggaaaaca | tcgtgtattt | agatttccgt | gcgctgtacc | ccagtattat | aatcacccac | 1260 |
| aatgtctcac | ctgacacgct | caacttggaa | ggttgcaaaa | attatgatat | tgctccgcaa | 1320 |
| gttggacata | agttttgtaa | agatattccg | ggcttcatcc | cgtccctgct | tggtcactta | 1380 |
| ctggaagagc | gccaaaaaat | taagaccaaa | atgaaagaga | ctcaggatcc | cattgaaaag | 1440 |
| atcctgctcg | attaccggca | aaaagccatt | aaattgcttg | caaactcgtt | ttatgggtac | 1500 |
| tatggctatg | cgaaggctcg | ttggtactgc | aaagaatgtg | ccgagagcgt | gacagcatgg | 1560 |
| ggtcgcaaat | atatagaatt | agtatggaag | gagctggaag | aaaaattcgg | attcaaagtc | 1620 |
| ctgtacatcg | atacggatgg | cctctatgcg | accattcctg | gtgggagtc | tgaagaaatc | 1680 |
| aagaaaaaag | ccttggaatt | ccttaagtat | ataaatgcta | aattacctgg | tgccctggag | 1740 |
| ctggaatacg | aagggttta | caaacgcgga | ttctttgtta | ctaagaaaaa | atatgcggtg | 1800 |
| atcgacgagg | aaggcaagat | tacgaccaga | ggcctcgaga | ttgtacggcg | tgattggagc | 1860 |
| gaaatcgcta | agaaacacg | ggcacgtgtc | ttggaggcat | tactgaaaga | tgggacgtt | 1920 |
| gaaaaggcgt | gcgaattgt | aaagaagtc | accgaaaaac | tttctaagta | cgaagttccg | 1980 |
| ccagagaaac | tggtgataca | cgaacaaatc | actcgtgatc | tgaaagacta | taaggctaca | 2040 |

```
ggcccgcatg tagcagtcgc caaacgcctc gcggctcggg gtgttaaaat tcgtcccgga    2100
acggtgatca gttacattgt attgaagggc tcaggtcgca tagggatag agcaatccct     2160 ttcgacgagt ttgatccaac caaacacaaa tatgatgccg aatactatat tgaaaaccag    2220
gtcttgccgg cggttgagcg tatactcgcg gctttcggct atcgaaagga agatcttcgt    2280
taccaaaaaa ctagacaggt gggtctgtcc gcatggctca aacctaaggg aacgtaa       2337
```

<210> SEQ ID NO 2
<211> LENGTH: 778
<212> TYPE: PRT
<213> ORGANISM: Artificial sequence
<220> FEATURE:
<223> OTHER INFORMATION: synthetic sequence

<400> SEQUENCE: 2

```
Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
            20                  25                  30

Tyr Asp Arg Thr Phe Glu Pro Tyr Phe Tyr Ala Leu Leu Lys Asp Asp
        35                  40                  45

Ser Ala Ile Glu Glu Val Lys Lys Ile Thr Ala Glu Arg His Gly Thr
    50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205

Leu Ile Thr Tyr Asn Gly Asp Asn Phe Asp Phe Ala Tyr Leu Lys Lys
    210                 215                 220

Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
                245                 250                 255

Gly Arg Ile His Phe Asp Leu Tyr Pro Val Ile Arg Arg Thr Ile Asn
            260                 265                 270

Leu Pro Thr Tyr Thr Leu Glu Ala Val Tyr Glu Ala Val Phe Gly Gln
        275                 280                 285

Pro Lys Glu Lys Val Tyr Ala Glu Glu Ile Thr Thr Ala Trp Glu Thr
    290                 295                 300

Gly Glu Asn Leu Glu Arg Val Ala Arg Tyr Ser Met Glu Asp Ala Lys
```

-continued

```
            305                 310                 315                 320
        Val Thr Tyr Glu Leu Gly Lys Glu Phe Leu Pro Met Glu Ala Gln Leu
                        325                 330                 335

Ser Arg Leu Val Gly Gln Pro Leu Trp Asp Val Ser Arg Ser Ser Thr
                        340                 345                 350

Gly Asn Leu Val Glu Trp Phe Leu Arg Lys Ala Tyr Glu Arg Asn
                        355                 360                 365

Glu Val Ala Pro Asn Lys Pro Ser Glu Glu Tyr Gln Arg Arg Leu
        370                 375                 380

Arg Glu Ser Tyr Thr Gly Gly Phe Val Lys Glu Pro Glu Lys Gly Leu
        385                 390                 395                 400

Trp Glu Asn Ile Val Tyr Leu Asp Phe Arg Ala Leu Tyr Pro Ser Ile
                        405                 410                 415

Ile Ile Thr His Asn Val Ser Pro Asp Thr Leu Asn Leu Glu Gly Cys
                        420                 425                 430

Lys Asn Tyr Asp Ile Ala Pro Gln Val Gly His Lys Phe Cys Lys Asp
                        435                 440                 445

Ile Pro Gly Phe Ile Pro Ser Leu Leu Gly His Leu Leu Glu Glu Arg
        450                 455                 460

Gln Lys Ile Lys Thr Lys Met Lys Glu Thr Gln Asp Pro Ile Glu Lys
        465                 470                 475                 480

Ile Leu Leu Asp Tyr Arg Gln Lys Ala Ile Lys Leu Leu Ala Asn Ser
                        485                 490                 495

Phe Tyr Gly Tyr Tyr Gly Tyr Ala Lys Ala Arg Trp Tyr Cys Lys Glu
                        500                 505                 510

Cys Ala Glu Ser Val Thr Ala Trp Gly Arg Lys Tyr Ile Glu Leu Val
                        515                 520                 525

Trp Lys Glu Leu Glu Glu Lys Phe Gly Phe Lys Val Leu Tyr Ile Asp
                        530                 535                 540

Thr Asp Gly Leu Tyr Ala Thr Ile Pro Gly Gly Glu Ser Glu Glu Ile
        545                 550                 555                 560

Lys Lys Lys Ala Leu Glu Phe Leu Lys Tyr Ile Asn Ala Lys Leu Pro
                        565                 570                 575

Gly Ala Leu Glu Leu Glu Tyr Glu Gly Phe Tyr Lys Arg Gly Phe Phe
                        580                 585                 590

Val Thr Lys Lys Lys Tyr Ala Val Ile Asp Glu Glu Gly Lys Ile Thr
                        595                 600                 605

Thr Arg Gly Leu Glu Ile Val Arg Arg Asp Trp Ser Glu Ile Ala Lys
        610                 615                 620

Glu Thr Gln Ala Arg Val Leu Glu Ala Leu Leu Lys Asp Gly Asp Val
        625                 630                 635                 640

Glu Lys Ala Val Arg Ile Val Lys Glu Val Thr Glu Lys Leu Ser Lys
                        645                 650                 655

Tyr Glu Val Pro Pro Glu Lys Leu Val Ile His Glu Gln Ile Thr Arg
                        660                 665                 670

Asp Leu Lys Asp Tyr Lys Ala Thr Gly Pro His Val Ala Val Ala Lys
                        675                 680                 685

Arg Leu Ala Ala Arg Gly Val Lys Ile Arg Pro Gly Thr Val Ile Ser
        690                 695                 700

Tyr Ile Val Leu Lys Gly Ser Gly Arg Ile Gly Asp Arg Ala Ile Pro
        705                 710                 715                 720

Phe Asp Glu Phe Asp Pro Thr Lys His Lys Tyr Asp Ala Glu Tyr Tyr
                        725                 730                 735
```

```
Ile Glu Asn Gln Val Leu Pro Ala Val Glu Arg Ile Leu Arg Ala Phe
                740                 745                 750

Gly Tyr Arg Lys Glu Asp Leu Arg Tyr Gln Lys Thr Arg Gln Val Gly
            755                 760                 765

Leu Ser Ala Trp Leu Lys Pro Lys Gly Thr
        770                 775

<210> SEQ ID NO 3
<211> LENGTH: 2334
<212> TYPE: DNA
<213> ORGANISM: Artificial Sequence
<220> FEATURE:
<223> OTHER INFORMATION: synthetic sequence

<400> SEQUENCE: 3
atggctagcg ccattctgga tgtggactat atcaccgaag agggcaaacc ggttatacgt      60
ttatttaaga agagaatgg taaattcaag atcgagcatg accgcacgtt ccgtccatac     120
atttacgcgt tgcttcggga tgatagcaaa attgaggaag tcaaaaagat caccggggaa     180
cgtcatggaa aaatagtaag aattgtggac gttgaaaaag tcgaaaagaa atttctgggc     240
aaaccgatca ctgtatggaa gctctatctg aacatcctc aggatgtgcc cacaattcga     300
gaaaaagttc gtgagcaccc agccgtcgtg gatatatttg aatatgacat ccctttttgca    360 aaacgctact taattgataa aggcctgatc ccgatggagg gggaagaaga acttaaaatt     420
ctggcttttg acatagaaac gctctatcat gagggagaag aatttggcaa aggtcccatc     480
attatgattt cttacgcgga tgagaacgaa gccaaggtaa tcacttggaa aaatattgac     540
ctgccgtacg ttgaagtggt cagttcagag cgggaaatga ttaaacgttt tttacgcatc     600
attagagaga aagatccaga tataatcgtt acatataacg gcgactcctt cgatttttcct    660 tacctggcaa acgagctga aaaattgggt attaaactta ccatcgggcg tgacggatcg     720
gaaccgaaaa tgcaacgcat ggcgatatg acggcgtag aggtgaaagg tcggatacac       780
tttgatctgt atcatgtcat caccccgtact attaatctcc ccacatacac gttagaagcc    840
gtttatgagg caatattcgg caagccgaaa gaaaaagtgt acgctgacga atcgcgaag      900 gcatgggaga gcggcgaaaa cctggagcgc gtagcaaaat attctatgga agatgctaaa    960
gcgacctacg aattgggaa agaatttctt ccaatggaaa ttcagctgtc gagattaata    1020
gggcagagcc tgtgggacgt gtctcgaagt tcaacgggaa acctcgtcga atggtttctg    1080
ttgcggaaag catacgagcg taatgaactt gcccctaaca aaccggatga aaaggagctg    1140
gcacgccgtc gccaatccta tgaaggcggt tacgttaaag aaccagagcg ggggttatgg    1200
gaaaatatcg tgtatctgga tttccgttcg ctctacccga gcattatcat tacccacaac    1260
gtatctcccg acactttgaa tcgcgagggc tgtaaagaat atgatgtcgc gccgcaggtt    1320
ggtcatagat tttgcaagga cttcccggga tttataccaa gtctgcttgg cgatttactg    1380
gaagagcgac aaaaaatcaa aaagaaaatg aaagctacaa tcgatccgat agaacgtaag    1440
ctgctcgact accgccagcg ggccatcaaa attttggcaa actcatatta tggttactat    1500
gggtacgcgc gtgctcgctg gtattgtaaa gagtgcgccg aatccgtgac ggcatggggc    1560
cgtgaataca tcaccatgac tattaaggag atagaagaga aatatggttt caaagtaatc    1620
tactcggata cagacggatt cttttgcgacg attcccggtg ccgatgcaga aaccgtcaag    1680
aaaaaagcga tggaattcgt taagtacatt aatagtaaat accgggact gcttgaactg    1740 gagtatgaag gcttctacaa aagaggttt tttcgttacta agaaacgata tgccgtaata    1800
```

```
gatgaagagg ggaaagtcat cacacgtggc ctcgagattg ttcgccggga ctggtcagag   1860
atagcaaagg aaacgcaggc gcgcgtgctc gaaaccatct tgaaacatgg tgatgtagag   1920
gaagccgtcc gcattgttaa agaggtgatc cagaagttag caaactatga aattccaccg   1980
gaaaaactgg cgatatacga gcaaatcact cgtccccttc acgaatataa agctattgga   2040
cctcatgtag ccgtcgcgaa gaaactggct gcaaaaggcg ttaagataaa accaggtatg   2100
gtgatcgggt acattgtact ccgcggcgac ggtccgattt ccaatagagc catcttggcg   2160
gaggaatatg atcctaaaaa gcataaatac gacgctgaat attacattga gaaccaggtc   2220
ttgccggcag ttctgcggat acttgaagga tttggctatc gtaaagaaga tctgcgctat   2280
caaaagacgc gacaggtggg tctgactagc tggttgaata tcaaaaaatc gtaa         2334
```

<210> SEQ ID NO 4
<211> LENGTH: 777
<212> TYPE: PRT
<213> ORGANISM: Artificial Sequence
<220> FEATURE:
<223> OTHER INFORMATION: synthetic sequence

<400> SEQUENCE: 4

```
Met Ala Ser Ala Ile Leu Asp Val Asp Tyr Ile Thr Glu Glu Gly Lys
1               5                   10                  15

Pro Val Ile Arg Leu Phe Lys Lys Glu Asn Gly Lys Phe Lys Ile Glu
            20                  25                  30

His Asp Arg Thr Phe Arg Pro Tyr Ile Tyr Ala Leu Leu Arg Asp Asp
        35                  40                  45

Ser Lys Ile Glu Glu Val Lys Lys Ile Thr Gly Glu Arg His Gly Lys
    50                  55                  60

Ile Val Arg Ile Val Asp Val Glu Lys Val Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110

Phe Glu Tyr Asp Ile Pro Phe Ala Lys Arg Tyr Leu Ile Asp Lys Gly
        115                 120                 125

Leu Ile Pro Met Glu Gly Glu Glu Leu Lys Ile Leu Ala Phe Asp
    130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
            180                 185                 190

Met Ile Lys Arg Phe Leu Arg Ile Ile Arg Glu Lys Asp Pro Asp Ile
        195                 200                 205

Ile Val Thr Tyr Asn Gly Asp Ser Phe Asp Phe Pro Tyr Leu Ala Lys
    210                 215                 220

Arg Ala Glu Lys Leu Gly Ile Lys Leu Thr Ile Gly Arg Asp Gly Ser
225                 230                 235                 240

Glu Pro Lys Met Gln Arg Ile Gly Asp Met Thr Ala Val Glu Val Lys
                245                 250                 255

Gly Arg Ile His Phe Asp Leu Tyr His Val Ile Thr Arg Thr Ile Asn
            260                 265                 270
```

```
Leu Pro Thr Tyr Thr Leu Glu Ala Val Tyr Glu Ala Ile Phe Gly Lys
            275                 280                 285

Pro Lys Glu Lys Val Tyr Ala Asp Glu Ile Ala Lys Ala Trp Glu Ser
290                 295                 300

Gly Glu Asn Leu Glu Arg Val Ala Lys Tyr Ser Met Glu Asp Ala Lys
305                 310                 315                 320

Ala Thr Tyr Glu Leu Gly Lys Glu Phe Leu Pro Met Glu Ile Gln Leu
                325                 330                 335

Ser Arg Leu Ile Gly Gln Ser Leu Trp Asp Val Ser Arg Ser Ser Thr
            340                 345                 350

Gly Asn Leu Val Glu Trp Phe Leu Leu Arg Lys Ala Tyr Glu Arg Asn
        355                 360                 365

Glu Leu Ala Pro Asn Lys Pro Asp Glu Lys Leu Ala Arg Arg Arg
370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
                405                 410                 415

Ile Thr His Asn Val Ser Pro Asp Thr Leu Asn Arg Glu Gly Cys Lys
            420                 425                 430

Glu Tyr Asp Val Ala Pro Gln Val Gly His Arg Phe Cys Lys Asp Phe
        435                 440                 445

Pro Gly Phe Ile Pro Ser Leu Leu Gly Asp Leu Leu Glu Glu Arg Gln
450                 455                 460

Lys Ile Lys Lys Lys Met Lys Ala Thr Ile Asp Pro Ile Glu Arg Lys
465                 470                 475                 480

Leu Leu Asp Tyr Arg Gln Arg Ala Ile Lys Ile Leu Ala Asn Ser Tyr
                485                 490                 495

Tyr Gly Tyr Tyr Gly Tyr Ala Arg Ala Arg Trp Tyr Cys Lys Glu Cys
            500                 505                 510

Ala Glu Ser Val Thr Ala Trp Gly Arg Glu Tyr Ile Thr Met Thr Ile
        515                 520                 525

Lys Glu Ile Glu Glu Lys Tyr Gly Phe Lys Val Ile Tyr Ser Asp Thr
530                 535                 540

Asp Gly Phe Phe Ala Thr Ile Pro Gly Ala Asp Ala Glu Thr Val Lys
545                 550                 555                 560

Lys Lys Ala Met Glu Phe Val Lys Tyr Ile Asn Ser Lys Leu Pro Gly
                565                 570                 575

Leu Leu Glu Leu Glu Tyr Glu Gly Phe Tyr Lys Arg Gly Phe Phe Val
            580                 585                 590

Thr Lys Lys Arg Tyr Ala Val Ile Asp Glu Glu Gly Lys Val Ile Thr
        595                 600                 605

Arg Gly Leu Glu Ile Val Arg Arg Asp Trp Ser Glu Ile Ala Lys Glu
610                 615                 620

Thr Gln Ala Arg Val Leu Glu Thr Ile Leu Lys His Gly Asp Val Glu
625                 630                 635                 640

Glu Ala Val Arg Ile Val Lys Glu Val Ile Gln Lys Leu Ala Asn Tyr
                645                 650                 655

Glu Ile Pro Pro Glu Lys Leu Ala Ile Tyr Glu Gln Ile Thr Arg Pro
            660                 665                 670

Leu His Glu Tyr Lys Ala Ile Gly Pro His Val Ala Val Ala Lys Lys
        675                 680                 685
```

```
Leu Ala Ala Lys Gly Val Lys Ile Lys Pro Gly Met Val Ile Gly Tyr
        690             695             700

Ile Val Leu Arg Gly Asp Gly Pro Ile Ser Asn Arg Ala Ile Leu Ala
705             710             715             720

Glu Glu Tyr Asp Pro Lys Lys His Lys Tyr Asp Ala Glu Tyr Tyr Ile
                725             730             735

Glu Asn Gln Val Leu Pro Ala Val Leu Arg Ile Leu Glu Gly Phe Gly
            740             745             750

Tyr Arg Lys Glu Asp Leu Arg Tyr Gln Lys Thr Arg Gln Val Gly Leu
        755             760             765

Thr Ser Trp Leu Asn Ile Lys Lys Ser
    770             775

<210> SEQ ID NO 5
<211> LENGTH: 2334
<212> TYPE: DNA
<213> ORGANISM: Artificial Sequence
<220> FEATURE:
<223> OTHER INFORMATION: synthetic sequence

<400> SEQUENCE: 5
```

| | | | | | |
|---|---|---|---|---|---|
| atggctagcg | ccattctgga | taccgactat | atcacggaag | atggcaaacc | ggtgatacgt | 60 |
| attttaaga | aagagaatgg | tgagttcaaa | atcgagtacg | accgcacttt | tgagccatat | 120 |
| ttctacgcgt | tactgaagga | cgatagcgcc | attgaagaag | ttaaaaaaat | caccgcagag | 180 |
| cggcatggga | cagtggtaac | cgtgaagaga | gttgaaaaag | tccagaaaaa | atttttggga | 240 |
| cgacctgtag | aagtgtggaa | actttatttc | actcaccccc | aagatgttcc | ggctatacgt | 300 |
| gataaaattc | gcgaacatcc | agcggtcatt | gatatttacg | aatatgatat | accttttgcc | 360 |
| aagcgttacc | tcatcgacaa | aggcctggtg | ccgatggaag | tgatgaaga | attaaaaatg | 420 |
| ttggcattcg | acattgaaac | actttatcac | gagggggaag | agtttgctga | gggtcccatc | 480 |
| ctgatgattt | cttatgcgga | tgaagagggt | gcccgcgtaa | taacctggaa | gaacgttgat | 540 |
| ctcccgtacg | tggacgtcgt | tagtacggaa | cgggaaatga | tcaaacgttt | cctgcgcgta | 600 |
| gtgaaagaga | aagatccaga | cgtcttaatt | acctataatg | gtgataactt | tgattttgca | 660 |
| tacctgaaaa | aagatgcga | aaagttgggc | ataaatttcg | ctcttggtcg | agacgggtca | 720 |
| gagcctaaaa | tccagcgtat | gggagatcgc | tttgcggttg | aagtgaaagg | ccggattcat | 780 |
| ttcgacctgt | atccggtaat | tcgtcgcact | atcaacctcc | ccacatacac | gttagaagcc | 840 |
| gtctatgagg | cagttttttgg | tcaaccgaag | gaaaaagttt | acgctgagga | aattaccact | 900 |
| gcgtgggaaa | caggcgagaa | tctggaacgt | gtagcccgct | attctatgga | ggatgcaaaa | 960 |
| gttacctatg | aattgggtaa | ggaatttctt | ccaatggagg | cgcagctgtc | gagattaata | 1020 |
| gggcagagcc | tgtgggacgt | gtctcgaagt | tcaacgggaa | acctcgtcga | atggtttctg | 1080 |
| ttgcggaaag | catacgagcg | taatgaactt | gcccctaaca | aaccggatga | aaaggagctg | 1140 |
| gcacgccgtc | gccaatccta | tgaaggcggt | tacgttaaag | aaccagagcg | ggggttatgg | 1200 |
| gaaaatatcg | tgtatctgga | tttccgttcg | ctctacccga | gcattatcat | tacccacaac | 1260 |
| gtatctcccg | acactttgaa | tcgcgagggc | tgtaaagaat | atgatgtcgc | gccgcaggtt | 1320 |
| ggtcatagat | tttgcaagga | cttcccggga | tttataccaa | gtctgcttgg | cgatttactg | 1380 |
| gaagagcgac | aaaaaatcaa | aaagaaaatg | aaagctacaa | tcgatccgat | agaacgtaag | 1440 |
| ctgctcgact | accgccagcg | ggccatcaaa | attttggcaa | actcatatta | tggttactat | 1500 |
| gggtacgcgc | gtgctcgctg | gtattgtaaa | gagtgcgccg | aatccgtgac | ggcatggggc | 1560 |

```
cgtgaataca tcaccatgac tattaaggag atagaagaga aatatggttt caaagtaatc    1620
tactcggata cagacggatt ctttgcgacg attcccggtg ccgatgcaga aaccgtcaag    1680
aaaaaagcga tggaattcct taagtatata aatgctaaat tacctggtgc cctggagctg    1740
gaatacgaag ggttttacaa acgcggattc tttgttacta agaaaaaata tgcggtgatc    1800
gacgaggaag gcaagattac gaccagaggc ctcgagattg tacggcgtga ttggagcgaa    1860
atcgctaaag aaacacaggc acgtgtcttg gaggcattac tgaaagatgg ggacgttgaa    1920
aaggcggtgc gaattgtaaa agaagtcacc gaaaaacttt ctaagtacga agttccgcca    1980
gagaaactgg tgatacacga acaaatcact cgtgatctga agactataa ggctacaggc    2040 ccgcatgtag cagtcgccaa acgcctcgcg gctcggggtg ttaaaattcg tcccggaacg    2100
gtgatcagtt acattgtatt gaagggctca ggtcgcatag gggatagagc aatcccttc    2160 gacgagtttg atccaaccaa acacaaatat gatgccgaat actatattga aaaccaggtc    2220
ttgccggcgg ttgagcgtat actgcgcgct ttcggctatc gaaaggaaga tcttcgttac    2280
caaaaaacta gacaggtggg tctgtccgca tggctcaaac ctaagggaac gtaa          2334

<210> SEQ ID NO 6
<211> LENGTH: 777
<212> TYPE: PRT
<213> ORGANISM: Artificial Sequence
<220> FEATURE:
<223> OTHER INFORMATION: synthetic sequence

<400> SEQUENCE: 6

Met Ala Ser Ala Ile Leu Asp Thr Asp Tyr Ile Thr Glu Asp Gly Lys
1               5                   10                  15

Pro Val Ile Arg Ile Phe Lys Lys Glu Asn Gly Glu Phe Lys Ile Glu
            20                  25                  30

Tyr Asp Arg Thr Phe Glu Pro Tyr Phe Tyr Ala Leu Leu Lys Asp Asp
        35                  40                  45

Ser Ala Ile Glu Glu Val Lys Lys Ile Thr Ala Glu Arg His Gly Thr
    50                  55                  60

Val Val Thr Val Lys Arg Val Glu Lys Val Gln Lys Lys Phe Leu Gly
65                  70                  75                  80

Arg Pro Val Glu Val Trp Lys Leu Tyr Phe Thr His Pro Gln Asp Val
                85                  90                  95

Pro Ala Ile Arg Asp Lys Ile Arg Glu His Pro Ala Val Ile Asp Ile
            100                 105                 110

Tyr Glu Tyr Asp Ile Pro Phe Ala Lys Arg Tyr Leu Ile Asp Lys Gly
        115                 120                 125

Leu Val Pro Met Glu Gly Asp Glu Glu Leu Lys Met Leu Ala Phe Asp
    130                 135                 140

Ile Glu Thr Leu Tyr His Glu Gly Glu Glu Phe Ala Glu Gly Pro Ile
145                 150                 155                 160

Leu Met Ile Ser Tyr Ala Asp Glu Glu Gly Ala Arg Val Ile Thr Trp
                165                 170                 175

Lys Asn Val Asp Leu Pro Tyr Val Asp Val Val Ser Thr Glu Arg Glu
            180                 185                 190

Met Ile Lys Arg Phe Leu Arg Val Val Lys Glu Lys Asp Pro Asp Val
        195                 200                 205

Leu Ile Thr Tyr Asn Gly Asp Asn Phe Asp Phe Ala Tyr Leu Lys Lys
    210                 215                 220
```

```
Arg Cys Glu Lys Leu Gly Ile Asn Phe Ala Leu Gly Arg Asp Gly Ser
225                 230                 235                 240

Glu Pro Lys Ile Gln Arg Met Gly Asp Arg Phe Ala Val Glu Val Lys
            245                 250                 255

Gly Arg Ile His Phe Asp Leu Tyr Pro Val Ile Arg Arg Thr Ile Asn
                260                 265                 270

Leu Pro Thr Tyr Thr Leu Glu Ala Val Tyr Glu Ala Val Phe Gly Gln
        275                 280                 285

Pro Lys Glu Lys Val Tyr Ala Glu Glu Ile Thr Thr Ala Trp Glu Thr
    290                 295                 300

Gly Glu Asn Leu Glu Arg Val Ala Arg Tyr Ser Met Glu Asp Ala Lys
305                 310                 315                 320

Val Thr Tyr Glu Leu Gly Lys Glu Phe Leu Pro Met Glu Ala Gln Leu
                325                 330                 335

Ser Arg Leu Ile Gly Gln Ser Leu Trp Asp Val Ser Arg Ser Ser Thr
                340                 345                 350

Gly Asn Leu Val Glu Trp Phe Leu Leu Arg Lys Ala Tyr Glu Arg Asn
        355                 360                 365

Glu Leu Ala Pro Asn Lys Pro Asp Glu Lys Glu Leu Ala Arg Arg Arg
    370                 375                 380

Gln Ser Tyr Glu Gly Gly Tyr Val Lys Glu Pro Glu Arg Gly Leu Trp
385                 390                 395                 400

Glu Asn Ile Val Tyr Leu Asp Phe Arg Ser Leu Tyr Pro Ser Ile Ile
                405                 410                 415

Ile Thr His Asn Val Ser Pro Asp Thr Leu Asn Arg Glu Gly Cys Lys
        420                 425                 430

Glu Tyr Asp Val Ala Pro Gln Val Gly His Arg Phe Cys Lys Asp Phe
    435                 440                 445

Pro Gly Phe Ile Pro Ser Leu Leu Gly Asp Leu Leu Glu Glu Arg Gln
450                 455                 460

Lys Ile Lys Lys Lys Met Lys Ala Thr Ile Asp Pro Ile Glu Arg Lys
465                 470                 475                 480

Leu Leu Asp Tyr Arg Gln Arg Ala Ile Lys Ile Leu Ala Asn Ser Tyr
                485                 490                 495

Tyr Gly Tyr Tyr Gly Tyr Ala Arg Ala Arg Trp Tyr Cys Lys Glu Cys
        500                 505                 510

Ala Glu Ser Val Thr Ala Trp Gly Arg Glu Tyr Ile Thr Met Thr Ile
    515                 520                 525

Lys Glu Ile Glu Glu Lys Tyr Gly Phe Lys Val Ile Tyr Ser Asp Thr
530                 535                 540

Asp Gly Phe Phe Ala Thr Ile Pro Gly Ala Asp Ala Glu Thr Val Lys
545                 550                 555                 560

Lys Lys Ala Met Glu Phe Leu Lys Tyr Ile Asn Ala Lys Leu Pro Gly
                565                 570                 575

Ala Leu Glu Leu Glu Tyr Glu Gly Phe Tyr Lys Arg Gly Phe Phe Val
        580                 585                 590

Thr Lys Lys Lys Tyr Ala Val Ile Asp Glu Glu Gly Lys Ile Thr Thr
    595                 600                 605

Arg Gly Leu Glu Ile Val Arg Arg Asp Trp Ser Glu Ile Ala Lys Glu
    610                 615                 620

Thr Gln Ala Arg Val Leu Glu Ala Leu Leu Lys Asp Gly Asp Val Glu
625                 630                 635                 640

Lys Ala Val Arg Ile Val Lys Glu Val Thr Glu Lys Leu Ser Lys Tyr
```

```
              645                 650                 655
Glu Val Pro Pro Glu Lys Leu Val Ile His Glu Gln Ile Thr Arg Asp
            660                 665                 670

Leu Lys Asp Tyr Lys Ala Thr Gly Pro His Val Ala Val Ala Lys Arg
            675                 680                 685

Leu Ala Ala Arg Gly Val Lys Ile Arg Pro Gly Thr Val Ile Ser Tyr
            690                 695                 700

Ile Val Leu Lys Gly Ser Gly Arg Ile Gly Asp Arg Ala Ile Pro Phe
705                 710                 715                 720

Asp Glu Phe Asp Pro Thr Lys His Lys Tyr Asp Ala Glu Tyr Tyr Ile
                725                 730                 735

Glu Asn Gln Val Leu Pro Ala Val Glu Arg Ile Leu Arg Ala Phe Gly
            740                 745                 750

Tyr Arg Lys Glu Asp Leu Arg Tyr Gln Lys Thr Arg Gln Val Gly Leu
            755                 760                 765

Ser Ala Trp Leu Lys Pro Lys Gly Thr
            770                 775

<210> SEQ ID NO 7
<211> LENGTH: 2337
<212> TYPE: DNA
<213> ORGANISM: Artificial Sequence
<220> FEATURE:
<223> OTHER INFORMATION: synthetic sequence

<400> SEQUENCE: 7
```

| | | | | | |
|---|---|---|---|---|---|
| atggctagcg | ccattctgga | tgtggactat | atcaccgaag | agggcaaacc | ggttatacgt | 60 |
| ttatttaaga | aagagaatgg | taaattcaag | atcgagcatg | accgcacgtt | ccgtccatac | 120 |
| atttacgcgt | tgcttcggga | tgatagcaaa | attgaggaag | tcaaaaagat | caccggggaa | 180 |
| cgtcatggaa | aaatagtaag | aattgtggac | gttgaaaaag | tcgaaaagaa | atttctgggc | 240 |
| aaaccgatca | ctgtatggaa | gctctatctg | aacatcctc | aggatgtgcc | acaattcga | 300 |
| gaaaaagttc | gtgagcaccc | agccgtcgtg | atatatttg | aatatgacat | cccttttgca | 360 |
| aaacgctact | taattgataa | aggcctgatc | ccgatggagg | gggaagaaga | acttaaaatt | 420 |
| ctggcttttg | acatagaaac | gctctatcat | gagggagaag | aatttggcaa | aggtcccatc | 480 |
| attatgattt | cttacgcgga | tgagaacgaa | gccaaggtaa | tcacttggaa | aaatattgac | 540 |
| ctgccgtacg | ttgaagtggt | cagttcagag | cgggaaatga | ttaaacgttt | tttacgcatc | 600 |
| attagagaga | aagatccaga | tataatcgtt | acatataacg | gcgactcctt | cgattttcct | 660 |
| tacctggcaa | aacgagctga | aaaattgggt | attaaactta | ccatcgggcg | tgacggatcg | 720 |
| gaaccgaaaa | tgcaacgcat | tggcgatatg | acggcggtag | aggtgaaagg | tcggatacac | 780 |
| tttgatctgt | atcatgtcat | cacccgtact | attaatctcc | ccacatacac | gttagaagcc | 840 |
| gtttatgagg | caatattcgg | caagccgaaa | gaaaaagtgt | acgctgacga | aatcgcgaag | 900 |
| gcatgggaga | gcggcgaaaa | cctggagcgc | gtagcaaaat | attctatgga | agatgctaaa | 960 |
| gcgacctacg | aattggggaa | agaatttctt | ccaatggaaa | ttcagctgag | tcgtttagtc | 1020 |
| ggacaacctc | tgtgggacgt | tcacgctcc | tcgactggca | atctcgtgga | gtggttcctg | 1080 |
| ttgagaaaag | cctatgaacg | aaacgaagta | gcaccgaata | accaagcga | ggaagaatat | 1140 |
| cagcgtcgcc | ttcgcgagtc | ttacacaggt | gggtttgtta | aggaaccgga | gaaaggtctt | 1200 |
| tgggaaaaca | tcgtgtattt | agatttccgt | gcgctgtacc | ccagtattat | aatcacccac | 1260 |
| aatgtctcac | ctgacacgct | caacttggaa | ggttgcaaaa | attatgatat | tgctccgcaa | 1320 |

```
gttggacata agttttgtaa agatattccg ggcttcatcc cgtccctgct tggtcactta   1380
ctggaagagc gccaaaaaat taagaccaaa atgaaagaga ctcaggatcc cattgaaaag   1440
atcctgctcg attaccggca aaaagccatt aaattgcttg caaactcgtt ttatgggtac   1500
tatggctatg cgaaggctcg ttggtactgc aaagaatgtg ccgagagcgt gacagcatgg   1560
ggtcgcaaat atatagaatt agtatggaag gagctggaag aaaaattcgg attcaaagtc   1620
ctgtacatcg atacggatgg cctctatgcg accattcctg gtggggagtc tgaagaaatc   1680
aagaaaaaag ccttggaatt cgttaagtac attaatagta aattaccggg actgcttgaa   1740
ctggagtatg aaggcttcta caaaagaggt tttttcgtta ctaagaaacg atatgccgta   1800
atagatgaag aggggaaagt catcacacgt ggcctcgaga ttgttcgccg ggactggtca   1860
gagatagcaa aggaaacgca ggcgcgcgtg ctcgaaacca tcttgaaaca tggtgatgta   1920
gaggaagccg tccgcattgt taaagaggtg atccagaagt tagcaaacta tgaaattcca   1980
ccggaaaaac tggcgatata cgagcaaatc actcgtcccc ttcacgaata taaagctatt   2040
ggacctcatg tagccgtcgc gaagaaactg gctgcaaaag gcgttaagat aaaaccaggt   2100
atggtgatcg ggtacattgt actccgcggc gacggtccga tttccaatag agccatcttg   2160
gcggaggaat atgatcctaa aaagcataaa tacgacgctg aatattacat tgagaaccag   2220
gtcttgccgg cagttctgcg gatacttgaa ggatttggct atcgtaaaga agatctgcgc   2280
tatcaaaaga cgcgacaggt gggtctgact agctggttga atatcaaaaa atcgtaa     2337
```

<210> SEQ ID NO 8  
<211> LENGTH: 778  
<212> TYPE: PRT  
<213> ORGANISM: Artificial Sequence  
<220> FEATURE:  
<223> OTHER INFORMATION: synthetic sequence

<400> SEQUENCE: 8

```
Met Ala Ser Ala Ile Leu Asp Val Asp Tyr Ile Thr Glu Glu Gly Lys
1               5                  10                  15

Pro Val Ile Arg Leu Phe Lys Lys Glu Asn Gly Lys Phe Lys Ile Glu
            20                  25                  30

His Asp Arg Thr Phe Arg Pro Tyr Ile Tyr Ala Leu Leu Arg Asp Asp
        35                  40                  45

Ser Lys Ile Glu Glu Val Lys Lys Ile Thr Gly Glu Arg His Gly Lys
    50                  55                  60

Ile Val Arg Ile Val Asp Val Glu Lys Val Lys Lys Phe Leu Gly
65                  70                  75                  80

Lys Pro Ile Thr Val Trp Lys Leu Tyr Leu Glu His Pro Gln Asp Val
                85                  90                  95

Pro Thr Ile Arg Glu Lys Val Arg Glu His Pro Ala Val Val Asp Ile
            100                 105                 110

Phe Glu Tyr Asp Ile Pro Phe Ala Lys Arg Tyr Leu Ile Asp Lys Gly
        115                 120                 125

Leu Ile Pro Met Glu Gly Glu Glu Leu Lys Ile Leu Ala Phe Asp
    130                 135                 140

Ile Glu Thr Leu Tyr His Glu Gly Glu Glu Phe Gly Lys Gly Pro Ile
145                 150                 155                 160

Ile Met Ile Ser Tyr Ala Asp Glu Asn Glu Ala Lys Val Ile Thr Trp
                165                 170                 175

Lys Asn Ile Asp Leu Pro Tyr Val Glu Val Val Ser Ser Glu Arg Glu
```

```
                    180                 185                 190
Met Ile Lys Arg Phe Leu Arg Ile Arg Glu Lys Asp Pro Asp Ile
                195                 200                 205
Ile Val Thr Tyr Asn Gly Asp Ser Phe Asp Phe Pro Tyr Leu Ala Lys
            210                 215                 220
Arg Ala Glu Lys Leu Gly Ile Lys Leu Thr Ile Gly Arg Asp Gly Ser
225                 230                 235                 240
Glu Pro Lys Met Gln Arg Ile Gly Asp Met Thr Ala Val Glu Val Lys
                245                 250                 255
Gly Arg Ile His Phe Asp Leu Tyr His Val Ile Thr Arg Thr Ile Asn
            260                 265                 270
Leu Pro Thr Tyr Thr Leu Glu Ala Val Tyr Glu Ala Ile Phe Gly Lys
        275                 280                 285
Pro Lys Glu Lys Val Tyr Ala Asp Glu Ile Ala Lys Ala Trp Glu Ser
    290                 295                 300
Gly Glu Asn Leu Glu Arg Val Ala Lys Tyr Ser Met Glu Asp Ala Lys
305                 310                 315                 320
Ala Thr Tyr Glu Leu Gly Lys Glu Phe Leu Pro Met Glu Ile Gln Leu
                325                 330                 335
Ser Arg Leu Val Gly Gln Pro Leu Trp Asp Val Ser Arg Ser Ser Thr
            340                 345                 350
Gly Asn Leu Val Glu Trp Phe Leu Leu Arg Lys Ala Tyr Glu Arg Asn
        355                 360                 365
Glu Val Ala Pro Asn Lys Pro Ser Glu Glu Tyr Gln Arg Arg Leu
    370                 375                 380
Arg Glu Ser Tyr Thr Gly Gly Phe Val Lys Glu Pro Glu Lys Gly Leu
385                 390                 395                 400
Trp Glu Asn Ile Val Tyr Leu Asp Phe Arg Ala Leu Tyr Pro Ser Ile
                405                 410                 415
Ile Ile Thr His Asn Val Ser Pro Asp Thr Leu Asn Leu Glu Gly Cys
            420                 425                 430
Lys Asn Tyr Asp Ile Ala Pro Gln Val Gly His Lys Phe Cys Lys Asp
        435                 440                 445
Ile Pro Gly Phe Ile Pro Ser Leu Leu Gly His Leu Leu Glu Glu Arg
    450                 455                 460
Gln Lys Ile Lys Thr Lys Met Lys Glu Thr Gln Asp Pro Ile Glu Lys
465                 470                 475                 480
Ile Leu Leu Asp Tyr Arg Gln Lys Ala Ile Lys Leu Leu Ala Asn Ser
                485                 490                 495
Phe Tyr Gly Tyr Tyr Gly Tyr Ala Lys Ala Arg Trp Tyr Cys Lys Glu
            500                 505                 510
Cys Ala Glu Ser Val Thr Ala Trp Gly Arg Lys Tyr Ile Glu Leu Val
        515                 520                 525
Trp Lys Glu Leu Glu Lys Phe Gly Phe Lys Val Leu Tyr Ile Asp
    530                 535                 540
Thr Asp Gly Leu Tyr Ala Thr Ile Pro Gly Gly Glu Ser Glu Glu Ile
545                 550                 555                 560
Lys Lys Lys Ala Leu Glu Phe Val Lys Tyr Ile Asn Ser Lys Leu Pro
                565                 570                 575
Gly Leu Leu Glu Leu Glu Tyr Glu Gly Phe Tyr Lys Arg Gly Phe Phe
            580                 585                 590
Val Thr Lys Lys Arg Tyr Ala Val Ile Asp Glu Glu Gly Lys Val Ile
        595                 600                 605
```

-continued

Thr Arg Gly Leu Glu Ile Val Arg Arg Asp Trp Ser Glu Ile Ala Lys
610                 615                 620

Glu Thr Gln Ala Arg Val Leu Glu Thr Ile Leu Lys His Gly Asp Val
625                 630                 635                 640

Glu Glu Ala Val Arg Ile Val Lys Glu Val Ile Gln Lys Leu Ala Asn
                645                 650                 655

Tyr Glu Ile Pro Pro Glu Lys Leu Ala Ile Tyr Glu Gln Ile Thr Arg
            660                 665                 670

Pro Leu His Glu Tyr Lys Ala Ile Gly Pro His Val Ala Val Ala Lys
        675                 680                 685

Lys Leu Ala Ala Lys Gly Val Lys Ile Lys Pro Gly Met Val Ile Gly
690                 695                 700

Tyr Ile Val Leu Arg Gly Asp Gly Pro Ile Ser Asn Arg Ala Ile Leu
705                 710                 715                 720

Ala Glu Glu Tyr Asp Pro Lys Lys His Lys Tyr Asp Ala Glu Tyr Tyr
                725                 730                 735

Ile Glu Asn Gln Val Leu Pro Ala Val Leu Arg Ile Leu Glu Gly Phe
            740                 745                 750

Gly Tyr Arg Lys Glu Asp Leu Arg Tyr Gln Lys Thr Arg Gln Val Gly
        755                 760                 765

Leu Thr Ser Trp Leu Asn Ile Lys Lys Ser
770                 775

<210> SEQ ID NO 9
<211> LENGTH: 560
<212> TYPE: PRT
<213> ORGANISM: Moloney murine leukemia virus
<220> FEATURE:
<221> NAME/KEY: misc_feature
<222> LOCATION: (229)..(229)
<223> OTHER INFORMATION: Xaa can be any naturally occurring amino acid

<400> SEQUENCE: 9

Ala Phe Pro Leu Glu Arg Pro Asp Trp Asp Tyr Thr Thr Gln Ala Gly
1               5                   10                  15

Arg Asn His Leu Val His Tyr Arg Gln Leu Leu Leu Ala Gly Leu Gln
                20                  25                  30

Asn Ala Gly Arg Ser Pro Thr Asn Leu Ala Lys Val Lys Gly Ile Thr
            35                  40                  45

Gln Gly Pro Asn Glu Ser Pro Ser Ala Phe Leu Glu Arg Leu Lys Glu
        50                  55                  60

Ala Tyr Arg Arg Tyr Thr Pro Tyr Asp Pro Glu Asp Pro Gly Gln Glu
65                  70                  75                  80

Thr Asn Val Ser Met Ser Phe Ile Trp Gln Ser Ala Pro Asp Ile Gly
                85                  90                  95

Arg Lys Leu Gly Arg Leu Glu Asp Leu Lys Ser Lys Thr Leu Gly Asp
            100                 105                 110

Leu Val Arg Glu Ala Glu Lys Ile Phe Asn Lys Arg Glu Thr Pro Glu
        115                 120                 125

Glu Arg Glu Glu Arg Ile Arg Arg Glu Thr Glu Glu Lys Glu Glu Arg
    130                 135                 140

Arg Arg Thr Val Asp Glu Gln Lys Lys Glu Arg Asp Arg Arg Arg
145                 150                 155                 160

His Arg Glu Met Ser Lys Leu Leu Ala Thr Val Val Ile Gly Gln Glu
                165                 170                 175

```
Gln Asp Arg Gln Glu Gly Glu Arg Lys Arg Pro Gln Leu Asp Lys Asp
            180                 185                 190

Gln Cys Ala Tyr Cys Lys Glu Lys Gly His Trp Ala Lys Asp Cys Pro
        195                 200                 205

Lys Lys Pro Arg Gly Pro Arg Gly Pro Arg Pro Gln Thr Ser Leu Leu
    210                 215                 220

Thr Leu Gly Asp Xaa Gly Gln Gly Gln Asp Pro Pro Glu Pro
225                 230                 235                 240

Arg Ile Thr Leu Lys Val Gly Gln Pro Val Thr Phe Leu Val Asp
            245                 250                 255

Thr Gly Ala Gln His Ser Val Leu Thr Gln Asn Pro Gly Pro Leu Ser
        260                 265                 270

Asp Lys Ser Ala Trp Val Gln Gly Ala Thr Gly Gly Lys Arg Tyr Arg
    275                 280                 285

Trp Thr Thr Asp Arg Lys Val His Leu Ala Thr Gly Lys Val Thr His
        290                 295                 300

Ser Phe Leu His Val Pro Asp Cys Pro Tyr Pro Leu Leu Gly Arg Asp
305                 310                 315                 320

Leu Leu Thr Lys Leu Lys Ala Gln Ile His Phe Glu Gly Ser Gly Ala
            325                 330                 335

Gln Val Val Gly Pro Met Gly Gln Pro Leu Gln Val Leu Thr Leu Asn
        340                 345                 350

Ile Glu Asp Glu Tyr Arg Leu His Glu Thr Ser Lys Glu Pro Asp Val
    355                 360                 365

Ser Leu Gly Phe Thr Trp Leu Ser Asp Phe Pro Gln Ala Trp Ala Glu
370                 375                 380

Ser Gly Gly Met Gly Leu Ala Val Arg Gln Ala Pro Leu Ile Ile Pro
385                 390                 395                 400

Leu Lys Ala Thr Ser Thr Pro Val Ser Ile Lys Gln Tyr Pro Met Ser
            405                 410                 415

Gln Glu Ala Arg Leu Gly Ile Lys Pro His Ile Gln Arg Leu Leu Asp
        420                 425                 430

Gln Gly Ile Leu Val Pro Cys Gln Ser Pro Trp Asn Thr Pro Leu Leu
    435                 440                 445

Pro Val Lys Lys Pro Gly Thr Asn Asp Tyr Arg Pro Val Gln Asp Leu
450                 455                 460

Arg Glu Val Asn Lys Arg Val Glu Asp Ile His Pro Thr Val Pro Asn
465                 470                 475                 480

Pro Tyr Asn Leu Leu Ser Gly Leu Pro Pro Ser His Gln Trp Tyr Thr
            485                 490                 495

Val Leu Asp Leu Lys Asp Ala Phe Phe Cys Leu Arg Leu His Pro Thr
        500                 505                 510

Ser Gln Pro Leu Phe Ala Phe Glu Trp Arg Asp Pro Glu Met Gly Ile
    515                 520                 525

Ser Gly Gln Leu Thr Trp Thr Arg Leu Pro Gln Gly Phe Lys Asn Ser
530                 535                 540

Pro Thr Leu Phe Asp Glu Ala Leu His Arg Asp Leu Ala Asp Phe Arg
545                 550                 555                 560
```

<210> SEQ ID NO 10
<211> LENGTH: 893
<212> TYPE: PRT
<213> ORGANISM: Avian Myeloblastosis Virus

<400> SEQUENCE: 10

-continued

```
Ile Gly Arg Ala Thr Val Leu Thr Val Ala Leu His Leu Ala Ile Pro
 1               5                  10                  15
Leu Lys Trp Lys Pro Asn His Thr Pro Val Trp Ile Asp Gln Trp Pro
             20                  25                  30
Leu Pro Glu Gly Lys Leu Val Ala Leu Thr Gln Leu Val Glu Lys Glu
         35                  40                  45
Leu Gln Leu Gly His Ile Glu Pro Ser Leu Ser Cys Trp Asn Thr Pro
     50                  55                  60
Val Phe Val Ile Arg Lys Ala Ser Gly Ser Tyr Arg Leu Leu His Asp
 65                  70                  75                  80
Leu Arg Ala Val Asn Ala Lys Leu Val Pro Phe Gly Ala Val Gln Gln
                 85                  90                  95
Gly Ala Pro Val Leu Ser Ala Leu Pro Arg Gly Trp Pro Leu Met Val
             100                 105                 110
Leu Asp Leu Lys Asp Cys Phe Phe Ser Ile Pro Leu Ala Glu Gln Asp
         115                 120                 125
Arg Glu Ala Phe Ala Phe Thr Leu Pro Ser Val Asn Asn Gln Ala Pro
     130                 135                 140
Ala Arg Arg Phe Gln Trp Lys Val Leu Pro Gln Gly Met Thr Cys Ser
145                 150                 155                 160
Pro Thr Ile Cys Gln Leu Ile Val Gly Gln Ile Leu Glu Pro Leu Arg
                 165                 170                 175
Leu Lys His Pro Ser Leu Arg Met Leu His Tyr Met Asp Asp Leu Leu
             180                 185                 190
Leu Ala Ala Ser Ser His Asp Gly Leu Glu Ala Ala Gly Glu Glu Val
         195                 200                 205
Ile Ser Thr Leu Glu Arg Ala Gly Phe Thr Ile Ser Pro Asp Lys Val
     210                 215                 220
Gln Arg Glu Pro Gly Val Gln Tyr Leu Gly Tyr Lys Leu Gly Ser Thr
225                 230                 235                 240
Tyr Val Ala Pro Val Gly Leu Val Ala Glu Pro Arg Ile Ala Thr Leu
                 245                 250                 255
Trp Asp Val Gln Lys Leu Val Gly Ser Leu Gln Trp Leu Arg Pro Ala
             260                 265                 270
Leu Gly Ile Pro Pro Arg Leu Arg Gly Pro Phe Tyr Glu Gln Leu Arg
         275                 280                 285
Gly Ser Asp Pro Asn Glu Ala Arg Glu Trp Asn Leu Asp Met Lys Met
     290                 295                 300
Ala Trp Arg Glu Ile Val Arg Leu Ser Thr Thr Ala Ala Leu Glu Arg
305                 310                 315                 320
Trp Asp Pro Ala Leu Pro Leu Glu Gly Ala Val Ala Arg Cys Glu Gln
                 325                 330                 335
Gly Ala Ile Gly Val Leu Gly Gln Gly Leu Ser Thr His Pro Arg Pro
             340                 345                 350
Cys Leu Trp Leu Phe Ser Thr Gln Pro Thr Lys Ala Phe Thr Ala Trp
         355                 360                 365
Leu Glu Val Leu Thr Leu Leu Ile Thr Lys Leu Arg Ala Ser Ala Val
     370                 375                 380
Arg Thr Phe Gly Lys Glu Val Asp Ile Leu Leu Leu Pro Ala Cys Phe
385                 390                 395                 400
Arg Asp Asp Leu Pro Leu Pro Glu Gly Ile Leu Leu Ala Leu Arg Gly
                 405                 410                 415
```

```
Phe Ala Gly Lys Ile Arg Ser Ser Asp Thr Pro Ser Ile Phe Asp Ile
            420                 425                 430

Ala Arg Pro Leu His Val Ser Leu Lys Val Arg Val Thr Asp His Pro
        435                 440                 445

Val Pro Gly Pro Thr Val Phe Thr Asp Ala Ser Ser Ser Thr His Lys
    450                 455                 460

Gly Val Val Val Trp Arg Glu Gly Pro Arg Trp Glu Ile Lys Glu Ile
465                 470                 475                 480

Ala Asp Leu Gly Ala Ser Val Gln Gln Leu Glu Ala Arg Ala Val Ala
                485                 490                 495

Met Ala Leu Leu Leu Trp Pro Thr Thr Pro Thr Asn Val Val Thr Asp
            500                 505                 510

Ser Ala Phe Val Ala Lys Met Leu Leu Lys Met Gly Gln Glu Gly Val
        515                 520                 525

Pro Ser Thr Ala Ala Ala Phe Ile Leu Glu Asp Ala Leu Ser Gln Arg
    530                 535                 540

Ser Ala Met Ala Ala Val Leu His Val Arg Ser His Ser Glu Val Pro
545                 550                 555                 560

Gly Phe Phe Thr Glu Gly Asn Asp Val Ala Asp Ser Gln Ala Thr Phe
                565                 570                 575

Gln Ala Tyr Pro Leu Arg Glu Ala Lys Asp Leu His Thr Ala Leu His
            580                 585                 590

Ile Gly Pro Arg Ala Leu Ser Lys Ala Cys Asn Ile Ser Met Gln Gln
        595                 600                 605

Ala Arg Glu Val Val Gln Thr Cys Pro His Cys Asn Ser Ala Pro Ala
    610                 615                 620

Leu Glu Ala Gly Val Asn Pro Arg Gly Leu Gly Pro Leu Gln Ile Trp
625                 630                 635                 640

Gln Thr Asp Phe Thr Leu Glu Pro Arg Met Ala Pro Arg Ser Trp Leu
                645                 650                 655

Ala Val Thr Val Asp Thr Ala Ser Ser Ala Ile Val Val Thr Gln His
            660                 665                 670

Gly Arg Val Thr Ser Val Ala Ala Gln His His Trp Ala Thr Ala Ile
        675                 680                 685

Ala Val Leu Gly Arg Pro Lys Ala Ile Lys Thr Asp Asn Gly Ser Cys
    690                 695                 700

Phe Thr Ser Lys Ser Thr Arg Glu Trp Leu Ala Arg Trp Gly Ile Ala
705                 710                 715                 720

His Thr Thr Gly Ile Pro Gly Asn Ser Gln Gly Gln Ala Met Val Glu
                725                 730                 735

Arg Ala Asn Arg Leu Leu Lys Asp Lys Ile Arg Val Leu Ala Glu Gly
            740                 745                 750

Asp Gly Phe Met Lys Arg Ile Pro Thr Ser Lys Gln Gly Glu Leu Leu
        755                 760                 765

Ala Lys Ala Met Tyr Ala Leu Asn His Phe Glu Arg Gly Glu Asn Thr
    770                 775                 780

Lys Thr Pro Ile Gln Lys His Trp Arg Pro Thr Val Leu Thr Glu Gly
785                 790                 795                 800

Pro Pro Val Lys Ile Arg Ile Glu Thr Gly Glu Trp Glu Lys Gly Trp
                805                 810                 815

Asn Val Leu Val Trp Gly Arg Gly Tyr Ala Ala Val Lys Asn Arg Asp
            820                 825                 830

Thr Asp Lys Val Ile Trp Val Pro Ser Arg Lys Val Lys Pro Asp Ile
```

```
                835                 840                 845
Ala Gln Lys Asp Glu Val Thr Lys Lys Asp Glu Ala Ser Pro Leu Phe
            850                 855                 860
Ala Gly Trp Arg His Ile Asp Lys Arg Ile Ile Thr Leu His Ser Ser
865                 870                 875                 880
Phe Ser Lys Ile Asn Leu Leu Val Cys Phe Ile Phe His
                885                 890
```

<210> SEQ ID NO 11
<211> LENGTH: 47
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(41)
<223> OTHER INFORMATION: n is a, c, g, t or u

<400> SEQUENCE: 11
tcgtcggcag cgtcagatgt gtataagaga cagnnnnnnnn nrgrgrg       47

<210> SEQ ID NO 12
<211> LENGTH: 47
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (34)..(41)
<223> OTHER INFORMATION: n is a, c, g, t or u

<400> SEQUENCE: 12
tcgtcggcag cgtcagatgt gtataagaga cagnnnnnnnn nrgrgrg       47

<210> SEQ ID NO 13
<211> LENGTH: 22
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (9)..(14)
<223> OTHER INFORMATION: n is a, c, g, or t

<400> SEQUENCE: 13
acgcgacgnn nnntgggac ga       22

<210> SEQ ID NO 14
<211> LENGTH: 6
<212> TYPE: PRT
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(6)
<223> OTHER INFORMATION: Xaa can be any naturally occurring amino acid

<400> SEQUENCE: 14

Xaa Xaa Xaa Xaa Xaa Xaa
1               5

SYSTEM AND METHOD FOR NUCLEIC ACID LIBRARY PREPARATION VIA TEMPLATE SWITCHING MECHANISM

RELATED APPLICATIONS

This application is a Continuation of International Patent Application No. PCT/US2018/064227, filed Dec. 6, 2018, which claims the benefit of U.S. provisional application U.S. Provisional Patent Application No. 62/595,393, filed Dec. 6, 2017, the contents of which are herein incorporated by reference in their entirety.

FIELD OF THE DISCLOSURE

The disclosure relates to the fields of molecular biology and DNA sequencing.

INCORPORATION OF SEQUENCE LISTING

The contents of the text file named "RMSI-012-001WO_SeqListing_ST25.txt," which was created on Dec. 6, 2018 and is 53 KB in size, are hereby incorporated by reference in their entirety.

BACKGROUND

It is difficult to efficiently detect novel DNA fusion events from a small amount of starting material. Current protocols in the field typically call for time consuming ligation steps that require large amounts DNA. The disclosure provides compositions and methods for the efficient detection novel fusion events through the addition of adaptors to the ends of DNA sequences via a template switching mechanism.

SUMMARY

The disclosure provides a composition comprising a double-stranded deoxyribonucleic acid (dsDNA) sequence comprising (a) a sense strand comprising, from 5' to 3', a sequence comprising a first adaptor sequence, a template sequence, and a second adaptor sequence, and (b) an anti-sense strand comprising a sequence comprising a sequence complementary to the sequence of the sense strand (a), wherein the second adaptor sequence comprises a hybridization site for a template switching oligonucleotide (TSO). In some embodiments of the compositions of the disclosure, the anti-sense strand of (b) comprises, from 5' to 3', a sequence comprising a reverse complement of the sequence of the sense strand (a).

In some embodiments of the compositions of the disclosure, the first adaptor sequence comprises between 1 and 5 nucleotides, inclusive of the endpoints. In some embodiments, the first adaptor sequence comprises three nucleotides. In some embodiments, the first adaptor sequence comprises a poly(G) sequence. In some embodiments, the first adaptor sequence comprises a poly(G) sequence or a poly (C) sequence.

In some embodiments of the compositions of the disclosure, the second adaptor sequence comprises between 1 and 5 nucleotides, inclusive of the endpoints. In some embodiments, the second adaptor sequence comprises three nucleotides. In some embodiments, the second adaptor sequence comprises a poly(C) sequence. In some embodiments, the second adaptor sequence comprises a poly(G) sequence or a poly (C) sequence.

In some embodiments of the compositions of the disclosure, the first adaptor sequence and the second adaptor sequence are not identical.

In some embodiments of the compositions of the disclosure, the hybridization site for the TSO comprises the poly(C) sequence. In some embodiments of the compositions of the disclosure, the hybridization site for the TSO comprises the poly(C) sequence or the poly (G) sequence. In some embodiments, the hybridization site for the TSO consists of the poly(C) sequence. In some embodiments, the hybridization site for the TSO consists of the poly(C) sequence or the poly (G) sequence.

In some embodiments of the compositions of the disclosure, the template sequence comprises a fragmented DNA sequence. In some embodiments, the fragmented DNA sequence comprises a PCR product, a sheared DNA, or a repaired DNA. In some embodiments, the PCR product is a blunt-ended product or a product with blunted ends.

In some embodiments of the compositions of the disclosure, the template sequence comprises a fragmented DNA sequence. In some embodiments, the fragmented DNA sequence comprises a PCR product, a sheared DNA, or a repaired DNA. In some embodiments, the sheared DNA comprises a mechanically or enzymatically sheared DNA. In some embodiments, the sheared DNA comprises genomic DNA. In some embodiments, the sheared DNA comprises a vector. In some embodiments, the sheared DNA comprises a natively sheared DNA. In some embodiments, the natively sheared DNA comprises a cell free DNA (cfDNA).

In some embodiments of the compositions of the disclosure, the template sequence comprises a fragmented DNA sequence. In some embodiments, the fragmented DNA sequence comprises a PCR product, a sheared DNA, or a repaired DNA. In some embodiments, the repaired DNA has been enzymatically repaired to be double-stranded.

In some embodiments of the compositions of the disclosure, the TSO comprises a single-stranded deoxyribonucleic acid (ssDNA) sequence. In some embodiments, the TSO further comprises a secondary structure. In some embodiments, the secondary structure comprises a hairpin. In some embodiments, the ssDNA sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the TSO. In some embodiments, the ssDNA sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO. In some embodiments, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO are continuous.

In some embodiments of the compositions of the disclosure, the TSO comprises a hybridization site having at least 50% complementarity to the hybridization site of the second adaptor. In some embodiments, the hybridization site has 100% complementarity to the hybridization site of the second adaptor. In some embodiments, hybridization site comprises a single-stranded nucleic acid sequence. In some embodiments, the single-stranded nucleic acid sequence comprises between 1 and 5 nucleotides, inclusive of the endpoints. In some embodiments, the single-stranded nucleic acid sequence comprises three nucleotides. In some embodiments, the single-stranded nucleic acid sequence is a DNA sequence. In some embodiments, the DNA sequence comprises a poly(G) sequence or a poly (C) sequence.

In some embodiments, the single-stranded nucleic acid sequence is an RNA sequence. In some embodiments, the RNA sequence comprises a poly(G) sequence. In some embodiments, the RNA sequence comprises a poly(G) sequence or a poly (C) sequence.

In some embodiments of the compositions of the disclosure, the TSO comprises a single-stranded deoxyribonucleic acid (ssDNA) sequence. In some embodiments, the ssDNA comprises a sequence having at least 50% identity or complementarity to a sequence of a primer, an adaptor, or a component of an array. In some embodiments, the ssDNA comprises a sequence having at least 50%, at least 55%, at least 60%, at least 65%, at least 70%, at least 75%, at least 80%, at least 85%, at least 90%, at least 95%, at least 97%, at least 99%, at least 100% or any percentage in between identity or complementarity to a sequence of a primer, an adaptor, or a component of an array.

In some embodiments of the compositions of the disclosure, the first adaptor sequence or the second adaptor sequence comprises a sequence of the TSO. In some embodiments, the first adaptor sequence or the second adaptor sequence comprises a sequence identical to a sequence of the TSO or a sequence complementary to a sequence of the TSO. In some embodiments, the first adaptor sequence comprises a sequence identical to a sequence of a first TSO or a sequence complementary to a sequence of the first TSO and the second adaptor sequence comprises a sequence identical to a sequence of a second TSO or a sequence complementary to a sequence of the second TSO, wherein the first TSO and the second TSO are not identical.

In some embodiments of the compositions of the disclosure, the first adaptor sequence or the second adaptor sequence comprises a sequence of the TSO. In some embodiments, the first adaptor sequence or the second adaptor sequence comprises a sequence identical to a sequence of the TSO or a sequence complementary to a sequence of the TSO. In some embodiments, the first adaptor sequence or the second adaptor sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the sequence of the TSO. In some embodiments, the first adaptor sequence or the second adaptor sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO. In some embodiments, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO are continuous.

In some embodiments of the compositions of the disclosure, the first adaptor sequence comprises a sequence identical to a sequence of a first TSO or a sequence complementary to a sequence of the first TSO and the second adaptor sequence comprises a sequence identical to a sequence of a second TSO or a sequence complementary to a sequence of the second TSO, and in some embodiments the first TSO and the second TSO are not identical. In some embodiments, the first adaptor sequence or the second adaptor sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the sequence of the first TSO or the second TSO, respectively.

In some embodiments, the first adaptor sequence or the second adaptor sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the first TSO or the second TSO, respectively. In some embodiments, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the first TSO or the second TSO, respectively, are continuous.

In some embodiments of the compositions of the disclosure, the sense strand comprises, from 5' to 3', a sequence comprising a first adaptor sequence, a template sequence, and a second adaptor sequence, wherein the first adaptor sequence comprises a sequence identical to the sequence of the TSO, a sequence identical to the sequence of a unique identifier (UID) sequence and the poly(G) sequence, and wherein the second adaptor sequence comprises a sequence complementary to the sequence of the TSO, a sequence complementary to the UID sequence and the poly(C) sequence.

In some embodiments of the compositions of the disclosure, the sense strand comprises, from 5' to 3', a sequence comprising a first adaptor sequence, a template sequence, and a second adaptor sequence, wherein the first adaptor sequence comprises a sequence identical to the sequence of the TSO, a sequence identical to the sequence of a unique identifier (UID) sequence, a sample identifier (SID) or a unique molecular identifier (UMI) sequence and the poly(G) sequence, and wherein the second adaptor sequence comprises a sequence complementary to the sequence of the TSO, a sequence complementary to the UID sequence, the SID sequence, or the UMI sequence and the poly(C) sequence.

In some embodiments of the compositions of the disclosure, the sense strand comprises, from 5' to 3', a sequence comprising a first adaptor sequence, a template sequence, and a second adaptor sequence, wherein the first adaptor sequence comprises a sequence identical to the sequence of the TSO, a sequence identical to the sequence of a unique identifier (UID) sequence, a sample identifier (SID) or a unique molecular identifier (UMI) sequence and the poly(C) sequence, and wherein the second adaptor sequence comprises a sequence complementary to the sequence of the TSO, a sequence complementary to the UID sequence, the SID sequence, or the UMI sequence and the poly(G) sequence.

In some embodiments of the compositions of the disclosure, the TSO comprises a UID sequence. In some embodiments of the compositions of the disclosure, the TSO comprises one or more of a UID sequence, a SID sequence or a UMI sequence. In some embodiments, the UID sequence comprises a random sequence. In some embodiments, the UID sequence, the SID sequence or the UMI sequence comprises a random sequence. In some embodiments, the UID sequence comprises a pre-determined sequence. In some embodiments, the UID sequence, the SID sequence or the UMI sequence comprises a pre-determined sequence. In some embodiments, the UID comprises a sequence between 1 and 20 nucleotides, inclusive of the endpoints. In some embodiments, the UID sequence, the SID sequence or the UMI sequence comprises a sequence between 1 and 20 nucleotides, inclusive of the endpoints. In some embodiments, the UID comprises a sequence between 2 and 12 nucleotides, inclusive of the endpoints. In some embodiments, the UID sequence, the SID sequence or the UMI sequence comprises a sequence between 2 and 12 nucleotides, inclusive of the endpoints. In some embodiments, the UID comprises a sequence between 4 and 10 nucleotides, inclusive of the endpoints. In some embodiments, the UID sequence, the SID sequence or the UMI sequence comprises a sequence between 4 and 10 nucleotides, inclusive of the endpoints. In some embodiments, the UID sequence comprises eight nucleotides. In some embodiments, the UID sequence or the SID sequence comprises eight nucleotides. In some embodiments, the UMI sequence comprises or consists of seven nucleotides. In some embodiments, the UMI sequence comprises or consists of five nucleotides.

The disclosure provides methods of making the dsDNA compositions of the disclosure comprising: (a) contacting a template sequence and a polymerase under conditions sufficient to allow for terminal transferase activity, to produce an intermediate double-stranded deoxyribonucleic acid (dsDNA) sequence, wherein the intermediate dsDNA comprises the adaptor sequence at the 3' end of the sense strand and the antisense strand; (b) contacting the intermediate dsDNA, the polymerase and at least one template switching oligonucleotide (TSO) under conditions sufficient to allow for DNA-dependent DNA polymerase activity, to produce the dsDNA of the compositions of the disclosure. In some embodiments, the adaptor sequence at the 3' end of the sense strand and the antisense strand comprises a poly(G) sequence or a poly(C) sequence. In some embodiments, the adaptor sequence at the 3' end of the sense strand and the antisense strand comprises a poly(G) sequence.

In some embodiments of the methods of the disclosure, the conditions sufficient to allow for terminal transferase activity or DNA-dependent DNA polymerase activity comprise a plurality of deoxynucleotides (dNTPs). In some embodiments, the conditions sufficient to allow for terminal transferase activity comprise a plurality of dCTPs. In some embodiments, the conditions sufficient to allow for terminal transferase activity comprise a plurality of dCTPs, a plurality of dGTPs, or a combination thereof. In some embodiments, the conditions sufficient to allow for terminal transferase activity comprise a combination of dCTPs and dGTPs. In some embodiments, the conditions sufficient to allow for DNA-dependent DNA polymerase activity comprise an incubation at temperatures from between 27° C. and 50° C., inclusive of the endpoints, for a period of 10 minutes. In some embodiments, the conditions sufficient to allow for DNA-dependent DNA polymerase activity comprise an incubation at 42° C. for 10 minutes. In some embodiments, the conditions sufficient to allow for DNA-dependent DNA polymerase activity comprise an incubation at temperatures from between 27° C. and 50° C., inclusive of the endpoints, for a period of between 2 and 20 minutes. In some embodiments, the conditions sufficient to allow for DNA-dependent DNA polymerase activity comprise an incubation at 42° C. for 10 minutes. In some embodiments, the conditions sufficient to allow for DNA-dependent DNA polymerase activity comprise an incubation at 42° C. for 5 minutes.

In some embodiments of the methods of the disclosure, the polymerase comprises a reverse transcriptase. In some embodiments, the reverse transcriptase is a Moloney Murine Leukemia Virus Reverse Transcriptase (MMLV) reverse transcriptase. In some embodiments, the reverse transcriptase is an Avian Myeloblastosis Virus (AMV) reverse transcriptase. In some embodiments, the conditions sufficient to allow for DNA-dependent DNA polymerase activity comprise the co-factor $Mg^{2+}$. In some embodiments, the co-factor $Mg^{2+}$ is present at a concentration of between 20 and 40 mM. In some embodiments, the co-factor $Mg^{2+}$ is present at a concentration of between 24 and 36 mM.

In some embodiments of the methods of the disclosure, a concentration of template DNA in (a) is between 0.1 ng and 100 ng, inclusive of the endpoints. In some embodiments, the concentration of template DNA in (a) is equal to or less than 0.1 ng, 1 ng, 10 ng or 100 ng.

The disclosure provides methods of making a DNA fragment library comprising: contacting a composition of the disclosure with a first forward primer, a first reverse primer, a polymerase and a plurality of dNTPs, and amplifying a first portion of the composition under conditions sufficient for the amplification to proceed, thereby producing a first amplification product.

In some embodiments of the methods of making a DNA fragment library of the disclosure, the first forward primer and the first reverse primer hybridize to the sense strand of the composition. In some embodiments, the first forward primer and the first reverse primer hybridize to the antisense strand of the composition. In some embodiments, the first forward primer hybridizes with a sequence within the first adaptor sequence. In some embodiments, the first forward primer hybridizes with a portion of a sequence identical to a sequence of the TSO. In some embodiments, the first reverse primer hybridizes with a sequence within the second adaptor sequence. In some embodiments, the first reverse primer hybridizes with a portion of a sequence identical to a sequence of the TSO. In some embodiments, the first reverse primer hybridizes with a sequence within the template sequence.

In some embodiments of the methods of making a DNA fragment library of the disclosure, the methods further comprise contacting the first amplification product, a second forward primer, a second reverse primer, a polymerase and a plurality of dNTPs, and amplifying the first amplification product under conditions sufficient for the amplification to proceed, thereby producing a second amplification product. In some embodiments, the second forward primer hybridizes with a sequence within the first adaptor sequence. In some embodiments, the second forward primer hybridizes with a sequence within a sequence identical to a sequence of the TSO. In some embodiments, the second reverse primer hybridizes with a sequence within the second adaptor sequence. In some embodiments, the second reverse primer hybridizes with a sequence within a sequence identical to a sequence of the TSO. In some embodiments, the second reverse primer hybridizes with a sequence within the template sequence. In some embodiments, the first forward primer and first reverse primer form a first primer pair, wherein the second forward primer and second reverse primer form a second primer pair, wherein the first primer pair contacted a composition of the disclosure and wherein the second primer pair contact the first amplification product.

In some embodiments of the methods of making a DNA fragment library of the disclosure, a forward primer or a reverse primer comprises a sample identifier (SID) sequence. In some embodiments of the methods of making a DNA fragment library of the disclosure, a forward primer or a reverse primer comprises a UID sequence or a SID sequence. In some embodiments, the SID sequence comprises a random sequence. In some embodiments, the UID sequence or the SID sequence comprises a random sequence. In some embodiments, the SID sequence comprises a pre-determined sequence. In some embodiments, the UID sequence or the SID sequence comprises a pre-determined sequence. In some embodiments, the SID comprises a sequence between 1 and 20 nucleotides, inclusive of the endpoints. In some embodiments, the UID sequence or the SID sequence a sequence between 1 and 20 nucleotides, inclusive of the endpoints. In some embodiments, the SID comprises a sequence between 2 and 12 nucleotides, inclusive of the endpoints. In some embodiments, the UID sequence or the SID sequence comprises a sequence between 2 and 12 nucleotides, inclusive of the endpoints. In some embodiments, the SID comprises a sequence between 4 and 10 nucleotides, inclusive of the endpoints. In some embodiments, the UID sequence or the SID sequence comprises a sequence between 4 and 10 nucleotides, inclusive of the endpoints. In some embodiments, the SID sequence comprises eight nucleotides. In some embodiments, the UID sequence or the SID sequence comprises eight nucleotides. In some embodiments, the SID sequence and the UID sequence are not identical. In some embodiments, the UID sequence or the SID sequence of the forward or reverse primer and the UID sequence the SID sequence or the UMI sequence of the TSO are not identical.

The disclosure provides a composition comprising a single-stranded deoxyribonucleic acid (ssDNA), the ssDNA comprising, from 5' to 3', a template sequence and an adaptor sequence, wherein the adaptor sequence comprises a hybridization site for a TSO.

In some embodiments of the ssDNA compositions of the disclosure, the adaptor sequence comprises between 1 and 5 nucleotides, inclusive of the endpoints. In some embodiments, the adaptor sequence comprises three nucleotides. In some embodiments, the adaptor sequence comprises a poly(C) sequence. In some embodiments, the adaptor sequence comprises a poly(C) sequence or a poly(G) sequence. In some embodiments, the hybridization site for the TSO comprises the poly(C) sequence. In some embodiments, the hybridization site for the TSO comprises the poly(C) sequence or the poly(G) sequence.

In some embodiments of the ssDNA compositions of the disclosure, the template sequence comprises a fragmented DNA sequence. In some embodiments, the fragmented DNA sequence comprises a PCR product, a sheared DNA, or a repaired DNA. In some embodiments, the PCR product is a blunt-ended product or a product with blunted ends.

In some embodiments of the ssDNA compositions of the disclosure, the template sequence comprises a fragmented DNA sequence. In some embodiments, the fragmented DNA sequence comprises a PCR product, a sheared DNA, or a repaired DNA. In some embodiments, the sheared DNA comprises a mechanically or enzymatically sheared DNA. In some embodiments, the sheared DNA comprises genomic DNA. In some embodiments, the sheared DNA comprises a vector. In some embodiments, the sheared DNA comprises a natively sheared DNA. In some embodiments, the natively sheared DNA comprises a cell free DNA (cfDNA).

In some embodiments of the ssDNA compositions of the disclosure, the template sequence comprises a fragmented DNA sequence. In some embodiments, the fragmented DNA sequence comprises a PCR product, a sheared DNA, or a repaired DNA. In some embodiments, the repaired DNA has been enzymatically repaired to be double-stranded.

In some embodiments of the ssDNA compositions of the disclosure, the TSO comprises a single-stranded deoxyribonucleic acid (ssDNA) sequence. In some embodiments, the TSO further comprises a secondary structure. In some embodiments, the secondary structure comprises a hairpin. In some embodiments, the ssDNA sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the TSO. In some embodiments, the ssDNA sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO. In some embodiments, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO are continuous.

In some embodiments of the ssDNA compositions of the disclosure, the TSO comprises a hybridization site having at least 50% complementarity to the hybridization site of the adaptor. In some embodiments, the hybridization site has 100% complementarity to the hybridization site of the adaptor. In some embodiments, the hybridization site comprises a single-stranded nucleic acid sequence. In some embodiments, the single-stranded nucleic acid sequence comprises between 1 and 5 nucleotides, inclusive of the endpoints. In some embodiments, wherein the single-stranded nucleic acid sequence comprises three nucleotides. In some embodiments, the single-stranded nucleic acid sequence is a DNA sequence. In some embodiments, the single-stranded nucleic acid sequence is an RNA sequence. In some embodiments, the RNA sequence comprises a poly(G) sequence.

In some embodiments of the ssDNA compositions of the disclosure, the TSO comprises a single-stranded deoxyribonucleic acid (ssDNA) sequence. In some embodiments, the ssDNA comprises a sequence having at least 50% identity or complementarity to a sequence of a primer, an adaptor, or a component of an array. In some embodiments, the ssDNA comprises a sequence having at least 50%, at least 55%, at least 60%, at least 65%, at least 70%, at least 75%, at least 80%, at least 85%, at least 90%, at least 95%, at least 97%, at least 99%, at least 100% or any percentage in between identity or complementarity to a sequence of a primer, an adaptor, or a component of an array. In some embodiments, the adaptor sequence comprises a sequence of the TSO. In some embodiments, the adaptor sequence comprises a sequence identical to a sequence of the TSO or a sequence complementary to a sequence of the TSO. In some embodiments, the adaptor sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the sequence of the TSO. In some embodiments, the adaptor sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO. In some embodiments, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO are continuous.

In some embodiments of the ssDNA compositions of the disclosure, the ssDNA comprises, from 5' to 3', a sequence comprising a template sequence and an adaptor sequence, wherein the adaptor sequence comprises a sequence complementary to the sequence of the TSO, a sequence complementary to the UID sequence and the poly(C) sequence. In some embodiments of the ssDNA compositions of the disclosure, the ssDNA comprises, from 5' to 3', a sequence comprising a template sequence and an adaptor sequence, and wherein the adaptor sequence comprises a sequence complementary to the sequence of the TSO, a sequence complementary to the UID sequence and the poly(G) sequence.

In some embodiments, the TSO comprises a UID sequence. In some embodiments, the TSO comprises a UID sequence, a SID sequence or a UMI sequence. In some embodiments, the UID sequence comprises a random sequence. In some embodiments, the UID sequence, the SID sequence or the UMI sequence comprises a random sequence. In some embodiments, the UID sequence comprises a pre-determined sequence. In some embodiments, the UID sequence, the SID sequence or the UMI sequence comprises a pre-determined sequence. In some embodiments, the UID comprises a sequence between 1 and 20 nucleotides, inclusive of the endpoints. In some embodiments, the UID sequence, the SID sequence or the UMI sequence comprises a sequence between 1 and 20 nucleotides, inclusive of the endpoints. In some embodiments, the UID comprises a sequence between 2 and 12 nucleotides, inclusive of the endpoints. In some embodiments, the UID sequence, the SID sequence or the UMI sequence comprises a sequence between 2 and 12 nucleotides, inclusive of the endpoints. In some embodiments, the UID comprises a sequence between 4 and 10 nucleotides, inclusive of the endpoints. In some embodiments, the UID sequence, the SID sequence or the UMI sequence comprises a sequence between 4 and 10 nucleotides, inclusive of the endpoints. In some embodiments, the UID sequence comprises eight nucleotides. In some embodiments, the UID sequence or the SID sequence comprises eight nucleotides. In some embodiments, the UMI sequence comprises seven nucleotides. In some embodiments, the UMI sequence comprises five nucleotides.

The disclosure provides methods of making a ssDNA of the disclosure, comprising: (a) denaturing a template sequence to produce a denatured template, (b) contacting the denatured template, a primer that hybridizes with a sequence of the denatured template, and a polymerase under conditions sufficient to allow for an initial primer extension activity followed by a second terminal transferase activity, to produce an intermediate ssDNA sequence, wherein the intermediate ssDNA comprises an adaptor sequence at a 3' end; (c) contacting the intermediate ssDNA, the polymerase and a TSO under conditions sufficient to allow for DNA-dependent DNA polymerase activity, to produce a ssDNA composition. In some embodiments, the adaptor sequence at the 3' end of the sense strand and the antisense strand comprises a poly(G) sequence or a poly(C) sequence. In some embodiments, the adaptor sequence at the 3' end of the sense strand and the antisense strand comprises a poly(G) sequence.

In some embodiments of the methods of making the ssDNAs of the disclosure, the methods further comprise (d) contacting the ssDNA composition of (c) and an exonuclease under conditions sufficient to allow for nuclease activity, to remove the primer of (b) and/or the TSO of (c), and (e) removing the exonuclease or a nuclease activity thereof to produce an isolated ssDNA composition.

In some embodiments of the methods of making the ssDNAs of the disclosure, the removing step comprising heating the ssDNA composition and the exonuclease of (c).

In some embodiments of the methods of making the ssDNAs of the disclosure, the polymerase comprises a thermostable polymerase. In some embodiments, the polymerase comprises a high-fidelity polymerase. In some embodiments, the polymerase has proof-reading activity. In some embodiments, the polymerase has proof-reading activity and is tolerant of uracil. In some embodiments, polymerase comprises a sequence of a Pfu polymerase, a sequence of a KOD polymerase or a combination thereof. In some embodiments, the polymerase comprises an N-terminal domain, an exonuclease domain, and a thumb domain a Pfu polymerase and a palm domain and a fingers domain of a KOD polymerase (also known as a "Pod" polymerase). In some embodiments, the polymerase comprises an N-terminal domain, an exonuclease domain, and a thumb domain a KOD polymerase and a palm domain and a fingers domain of a Pfu polymerase (also known as a "Kofu" polymerase).

In some embodiments of the polymerases of the disclosure, the polymerase is a Kofu polymerase and comprises the nucleic acid sequence of

```
                                                          (SEQ ID NO: 1)
  1 atggctagcg ccattctgga taccgactat atcacggaag atggcaaacc ggtgatacgt 61 atttttaaga aagagaatgg tgagttcaaa atcgagtacg accgcacttt tgagccatat 121 ttctacgcgt tactgaagga cgatagcgcc attgaagaag ttaaaaaaat caccgcagag 181 cggcatggga cagtggtaac cgtgaagaga gttgaaaaag tccagaaaaa atttttggga 241 cgacctgtag aagtgtggaa actttatttc actcaccccc aagatgttcc ggctatacgt 301 gataaaattc gcgaacatcc agcggtcatt gatatttacg aatatgatat accttttgcc 361 aagcgttacc tcatcgacaa aggcctggtg ccgatggaag gtgatgaaga attaaaaatg 421 ttggcattcg acattgaaac actttatcac gaggggggaag agtttgctga gggtcccatc 481 ctgatgattt cttatgcgga tgaagagggt gcccgcgtaa taacctggaa gaacgttgat 541 ctcccgtacg tggacgtcgt tagtacggaa cgggaaatga tcaaacgttt cctgcgcgta 601 gtgaaagaga aagatccaga cgtcttaatt acctataatg gtgataactt tgattttgca 661 tacctgaaaa aaagatgcga aaagttgggc ataaatttcg ctcttggtcg agacgggtca 721 gagcctaaaa tccagcgtat gggagatcgc tttgcggttg aagtgaaagg ccggattcat 781 ttcgacctgt atccggtaat tcgtcgcact atcaacctcc ccacatacac gttagaagcc 841 gtctatgagg cagttttggg tcaaccgaag gaaaaagttt acgctgagga aattaccact
```

-continued

```
 901 gcgtgggaaa caggcgagaa tctggaacgt gtagcccgct attctatgga ggatgcaaaa
 961 gttacctatg aattgggtaa ggaatttctt ccaatggagg cgcagctgag tcgtttagtc
1021 ggacaacctc tgtgggacgt ttcacgctcc tcgactggca atctcgtgga gtggttcctg
1081 ttgagaaaag cctatgaacg aaacgaagta gcaccgaata aaccaagcga ggaagaatat
1141 cagcgtcgcc ttcgcgagtc ttacacaggt gggtttgtta aggaaccgga gaaaggtctt
1201 tgggaaaaca tcgtgtattt agatttccgt gcgctgtacc ccagtattat aatcacccac
1261 aatgtctcac ctgacacgct caacttggaa ggttgcaaaa attatgatat tgctccgcaa
1321 gttggacata agttttgtaa agatattccg ggcttcatcc cgtccctgct tggtcactta
1381 ctggaagagc gccaaaaaat taagaccaaa atgaaagaga ctcaggatcc cattgaaaag
1441 atcctgctcg attaccggca aaaagccatt aaattgcttg caaactcgtt ttatgggtac
1501 tatggctatg cgaaggctcg ttggtactgc aaagaatgtg ccgagagcgt gacagcatgg
1561 ggtcgcaaat atatagaatt agtatggaag gagctggaag aaaaattcgg attcaaagtc
1621 ctgtacatcg atacggatgg cctctatgcg accattcctg gtggggagtc tgaagaaatc
1681 aagaaaaaag ccttggaatt ccttaagtat ataaatgcta aattacctgg tgccctggag
1741 ctggaatacg aagggtttta caaacgcgga ttctttgtta ctaagaaaaa atatgcggtg
1801 atcgacgagg aaggcaagat tacgaccaga ggcctcgaga ttgtacggcg tgattggagc
1861 gaaatcgcta agaaacaca ggcacgtgtc ttggaggcat tactgaaaga tggggacgtt
1921 gaaaaggcgg tgcgaattgt aaaagaagtc accgaaaaac tttctaagta cgaagttccg
1981 ccagagaaac tggtgataca cgaacaaatc actcgtgatc tgaaagacta taaggctaca
2041 ggcccgcatg tagcagtcgc caaacgcctc gcggctcggg gtgttaaaat tcgtcccgga
2101 acggtgatca gttacattgt attgaagggc tcaggtcgca tagggatag agcaatccct
2161 ttcgacgagt ttgatccaac caaacacaaa tatgatgccg aatactatat tgaaaaccag
2221 gtcttgccgg cggttgagcg tatactgcgc gctttcggct atcgaaagga agatcttcgt
2281 taccaaaaaa ctagacaggt gggtctgtcc gcatggctca aacctaaggg aacgtaa.
```

In some embodiments of the polymerases of the disclosure, the polymerase is a Kofu polymerase and comprises the amino acid sequence of (SEQ ID NO: 2)
MASAILDTDYITEDGKPVIRIFKKENGEFKIEYDRTFEPYFYALLKDDSA

IEEVKKITAERHGTVVTVKRVEKVQKKFLGRPVEVWKLYFTHPQDVPAIR

DKIREHPAVIDIYEYDIPEAKRYLIDKGLVPMEGDEELKMLAFDIETLYH

EGEEFAEGPILMISYADEEGARVITWKNVDLPYVDVVSTEREMIKRFLRV

VKEKDPDVLITYNGDNFDFAYLKKRCEKLGINFALGRDGSEPKIQRMGDR

FAVEVKGRIHFDLYPVIRRTINLPTYTLEAVYEAVFGQPKEKVYAEEITT

AWETGENLERVARYSMEDAKVTYELGKEFLPMEAQLSRLVGQPLWDVSRS

STGNLVEWFLLRKAYERNEVAPNKPSEEEYQRRLRESYTGGFVKEPEKGL

WENIVYLDFRALYPSIIITHNVSPDTLNLEGCKNYDIAPQVGHKFCKDIP

GFIPSLLGHLLEERQKIKTKMKETQDPIEKILLDYRQKAIKLLANSFYGY

YGYAKARWYCKECAESVTAWGRKYIELVWKELEEKFGFKVLYIDTDGLYA

TIPGGESEEIKKKALEFLKYINAKLPGALELEYEGFYKRGFFVTKKKYAV

IDEEGKITTRGLEIVRRDWSEIAKETQARVLEALLKDGDVEKAVRIVKEV

TEKLSKYEVPPEKLVIHEQITRDLKDYKATGPHVAVAKRLAARGVKIRPG

TVISYIVLKGSGRIGDRAIPFDEFDPTKHKYDAEYYIENQVLPAVERILR

AFGYRKEDLRYQKTRQVGLSAWLKPKGT.

In some embodiments of the polymerases of the disclosure, the polymerase is a Pod polymerase and comprises the nucleic acid sequence of (SEQ ID NO: 3)
```
  1 atggctagcg ccattctgga tgtggactat atcaccgaag agggcaaacc ggttatacgt
 61 ttatttaaga aagagaatgg taaattcaag atcgagcatg accgcacgtt ccgtccatac
121 atttacgcgt tgcttcggga tgatagcaaa attgaggaag tcaaaaagat caccggggaa
```

-continued

```
 181 cgtcatggaa aaatagtaag aattgtggac gttgaaaaag tcgaaaagaa atttctgggc 241 aaaccgatca ctgtatggaa gctctatctg aacatcctc aggatgtgcc cacaattcga 301 gaaaaagttc gtgagcaccc agccgtcgtg gatatatttg aatatgacat ccctttttgca 361 aaacgctact taattgataa aggcctgatc ccgatggagg gggaagaaga acttaaaatt 421 ctggcttttg acatagaaac gctctatcat gagggagaag aatttggcaa aggtcccatc 481 attatgattt cttacgcgga tgagaacgaa gccaaggtaa tcacttggaa aaatattgac 541 ctgccgtacg ttgaagtggt cagttcagag cgggaaatga ttaaacgttt tttacgcatc 601 attagagaga aagatccaga tataatcgtt acatataacg gcgactcctt cgatttttcct 661 tacctggcaa aacgagctga aaaattgggt attaaactta ccatcgggcg tgacggatcg 721 gaaccgaaaa tgcaacgcat tggcgatatg acggcggtag aggtgaaagg tcggatacac 781 tttgatctgt atcatgtcat cacccgtact attaatctcc ccacatacac gttagaagcc 841 gtttatgagg caatattcgg caagccgaaa gaaaaagtgt acgctgacga aatcgcgaag 901 gcatgggaga gcggcgaaaa cctggagcgc gtagcaaaat attctatgga agatgctaaa 961 gcgacctacg aattggggaa agaatttctt ccaatggaaa ttcagctgtc gagattaata 1021 gggcagagcc tgtgggacgt gtctcgaagt caacgggaa acctcgtcga atggtttctg 1081 ttgcggaaag catacgagcg taatgaactt gccctaaca aaccggatga aaggagctg 1141 gcacgccgtc gccaatccta tgaaggcggt tacgttaaag aaccagagcg ggggttatgg 1201 gaaaatatcg tgtatctgga tttccgttcg ctctacccga gcattatcat tacccacaac 1261 gtatctcccg acactttgaa tcgcgagggc tgtaaagaat atgatgtcgc gccgcaggtt 1321 ggtcatagat tttgcaagga cttcccggga tttataccaa gtctgcttgg cgatttactg 1381 gaagagcgac aaaaaatcaa aaagaaaatg aaagctacaa tcgatccgat agaacgtaag 1441 ctgctcgact accgccagcg ggccatcaaa attttggcaa actcatatta tggttactat 1501 gggtacgcgc gtgctcgctg gtattgtaaa gagtgcgccg aatccgtgac ggcatggggc 1561 cgtgaataca tcaccatgac tattaaggag atagaagaga aatatggttt caaagtaatc 1621 tactcggata cagacggatt ctttgcgacg attcccggtg ccgatgcaga aaccgtcaag 1681 aaaaaagcga tggaattcgt taagtacatt aatagtaaat taccgggact gcttgaactg 1741 gagtatgaag gcttctacaa aagaggtttt ttcgttacta gaaaacgata tgccgtaata 1801 gatgaagagg ggaaagtcat cacacgtggc ctcgagattg ttcgccggga ctggtcagag 1861 atagcaaagg aaacgcaggc gcgcgtgctc gaaaccatct tgaaacatgg tgatgtagag 1921 gaagccgtcc gcattgttaa agaggtgatc cagaagttag caaactatga aattccaccg 1981 gaaaaactgg cgatatacga gcaaatcact cgtcccctttc acgaatataa agctattgga 2041 cctcatgtag ccgtcgcgaa gaaactggct gcaaaaggcg ttaagataaa accaggtatg 2101 gtgatcgggt acattgtact ccgcggcgac ggtccgattt ccaatagagc catcttggcg 2161 gaggaatatg atcctaaaaa gcataaatac gacgctgaat attacattga gaaccaggtc 2221 ttgccggcag ttctgcggat acttgaagga tttggctatc gtaaagaaga tctgcgctat 2281 caaaagacgc gacaggtggg tctgactagc tggttgaata tcaaaaaatc gtaa
```

In some embodiments of the polymerases of the disclosure, the polymerase is a Pod polymerase and comprises the amino acid sequence of (SEQ ID NO: 4)
MASAILDVDYITEEGKPVIRLFKKENGKFKIEHDRTFRPYIYALLRDDSK
IEEVKKITGERHGKIVRIVDVEKVEKKFLGKPITVWKLYLEHPQDVPTIR
EKVREHPAVVDIFEYDIPFAKRYLIDKGLIPMEGEEELKILAFDIETLYH
EGEEFGKGPIIMISYADENEAKVITWKNIDLPYVEVVSSEREMIKRFLRI
IREKDPDIIVTYNGDSFDFPYLAKRAEKLGIKLTIGRDGSEPKMQRIGDM
TAVEVKGRIHFDLYHVITRTINLPTYTLEAVYEAIFGKPKEKVYADEIAK
AWESGENLERVAKYSMEDAKATYELGKEFLPMEIQLSRLIGQSLWDVSRS
STGNLVEWFLLRKAYERNELAPNKPDEKELARRRQSYEGGYVKEPERGLW
ENIVYLDFRSLYPSIIITHNVSPDTLNREGCKEYDVAPQVGHRFCKDFPG
FIPSLLGDLLEERQKIKKKMKATIDPIERKLLDYRQRAIKILANSYYGYY
GYARARWYCKECAESVTAWGREYITMTIKEIEEKYGFKVIYSDTDGFFAT
IPGADAETVKKKAMEFVKYINSKLPGLLELEYEGFYKRGFFVTKKRYAVI
DEEGKVITRGLEIVRRDWSEIAKETQARVLETILKHGDVEEAVRIVKEVI
QKLANYEIPPEKLAIYEQITRPLHEYKAIGPHVAVAKKLAAKGVKIKPGM
VIGYIVLRGDGPISNRAILAEEYDPKKHKYDAEYYIENQVLPAVLRILEG
FGYRKEDLRYQKTRQVGLTSWLNIKKS.

In some embodiments of the polymerases of the disclosure, the polymerase is a KOD polymerase and comprises the nucleic acid sequence of (SEQ ID NO: 5)
```
   1 atggctagcg ccattctgga taccgactat atcacggaag atggcaaacc ggtgatacgt
  61 atttttaaga aagagaatgg tgagttcaaa atcgagtacg accgcacttt tgagccatat
 121 ttctacgcgt tactgaagga cgatagcgcc attgaagaag ttaaaaaaat caccgcagag
 181 cggcatggga cagtggtaac cgtgaagaga gttgaaaaag tccagaaaaa attttttggga
 241 cgacctgtag aagtgtggaa actttatttc actcaccccc aagatgttcc ggctatacgt
 301 gataaaattc gcgaacatcc agcggtcatt gatatttacg aatatgatat accttttgcc
 361 aagcgttacc tcatcgacaa aggcctggtg ccgatggaag gtgatgaaga attaaaaatg
 421 ttggcattcg acattgaaac actttatcac gaggggaag agtttgctga gggtcccatc
 481 ctgatgattt cttatgcgga tgaagagggt gcccgcgtaa taacctggaa gaacgttgat
 541 ctcccgtacg tggacgtcgt tagtacggaa cgggaaatga tcaaacgttt cctgcgcgta
 601 gtgaaagaga aagatccaga cgtcttaatt acctataatg tgataactt tgattttgca
 661 tacctgaaaa aaagatgcga aaagttgggc ataaatttcg ctcttggtcg agacgggtca
 721 gagcctaaaa tccagcgtat gggagatcgc tttgcggttg aagtgaaagg ccggattcat
 781 ttcgacctgt atccggtaat tcgtcgcact atcaacctcc ccacatacac gttagaagcc
 841 gtctatgagg cagtttttgg tcaaccgaag gaaaagtttt acgctgagga aattaccact
 901 gcgtgggaaa caggcgagaa tctggaacgt gtagcccgct attctatgga ggatgcaaaa
 961 gttacctatg aattgggtaa ggaatttctt ccaatggagg cgcagctgtc gagattaata
1021 gggcagagcc tgtgggacgt gtctcgaagt tcaacgggaa acctcgtcga atggtttctg
1081 ttgcggaaag catacgagcg taatgaactt gcccctaaca aaccggatga aaaggagctg
1141 gcacgccgtc gccaatccta tgaaggcggt tacgttaaag aaccagagcg ggggttatgg
1201 gaaaatatcg tgtatctgga tttccgttcg ctctacccga gcattatcat tacccacaac
1261 gtatctcccg acactttgaa tcgcgagggc tgtaaagaat atgatgtcgc gccgcaggtt
1321 ggtcatagat tttgcaagga cttcccggga tttataccaa gtctgcttgg cgatttactg
1381 gaagagcgac aaaaaatcaa aaagaaaatg aaagctacaa tcgatccgat agaacgtaag
1441 ctgctcgact accgccagcg ggccatcaaa attttggcaa actcatatta tggttactat
1501 gggtacgcgc gtgctcgctg gtattgtaaa gagtgcgccg aatccgtgac ggcatggggc
1561 cgtgaataca tcaccatgac tattaaggag atagaagaga aatatggttt caaagtaatc
1621 tactcggata cagacggatt ctttgcgacg attcccgtg ccgatgcaga aaccgtcaag
```

```
1681 aaaaaagcga tggaattcct taagtatata aatgctaaat tacctggtgc cctggagctg 1741 gaatacgaag ggttttacaa acgcggattc tttgttacta agaaaaaata tgcggtgatc 1801 gacgaggaag gcaagattac gaccagaggc ctcgagattg tacggcgtga ttggagcgaa 1861 atcgctaaag aaacacaggc acgtgtcttg gaggcattac tgaaagatgg ggacgttgaa 1921 aaggcggtgc gaattgtaaa agaagtcacc gaaaaacttt ctaagtacga agttccgcca 1981 gagaaactgg tgatacacga acaaatcact cgtgatctga aagactaaa ggctacaggc 2040 ccgcatgtag cagtcgccaa acgcctcgcg gctcggggtg ttaaaattcg tcccggaacg 2100 gtgatcagtt acattgtatt gaagggctca ggtcgcatag gggatagagc aatcccttc 2160 gacgagtttg atccaaccaa acacaaatat gatgccgaat actatattga aaaccaggtc 2220 ttgccggcgg ttgagcgtat actgcgcgct ttcggctatc gaaaggaaga tcttcgttac 2280 caaaaaacta gacaggtggg tctgtccgca tggctcaaac ctaagggaac gtaa.
```

In some embodiments of the polymerases of the disclosure, the polymerase is a KOD polymerase and comprises the amino acid sequence of (SEQ ID NO: 6)
MASAILDTDYITEDGKPVIRIFKKENGEFKIEYDRTFEPYFYALLKDDSA

IEEVKKITAERHGTVVTVKRVEKVQKKFLGRPVEVWKLYFTHPQDVPAIR

DKIREHPAVIDIYEYDIPEAKRYLIDKGLVPMEGDEELKMLAFDIETLYH

EGEEFAEGPILMISYADEEGARVITWKNVDLPYVDVVSTEREMIKRFLRV

VKEKDPDVLITYNGDNFDFAYLKKRCEKLGINFALGRDGSEPKIQRMGDR

FAVEVKGRIHFDLYPVIRRTINLPTYTLEAVYEAVFGQPKEKVYAEEITT

AWETGENLERVARYSMEDAKVTYELGKEFLPMEAQLSRLIGQSLWDVSRS

STGNLVEWFLLRKAYERNELAPNKPDEKELARRRQSYEGGYVKEPERGLW

ENIVYLDFRSLYPSIIITHNVSPDTLNREGCKEYDVAPQVGHRFCKDFPG

FIPSLLGDLLEERQKIKKKMKATIDPIERKLLDYRQRAIKILANSYYGYY

GYARARWYCKECAESVTAWGREYITMTIKEIEEKYGFKVIYSDTDGFFAT

IPGADAETVKKKAMEFLKYINAKLPGALELEYEGFYKRGFFVTKKKYAVI

DEEGKITTRGLEIVRRDWSEIAKETQARVLEALLKDGDVEKAVRIVKEVT

EKLSKYEVPPEKLVIHEQITRDLKDYKATGPHVAVAKRLAARGVKIRPGT

VISYIVLKGSGRIGDRAIPFDEFDPTKHKYDAEYYIENQVLPAVERILRA

FGYRKEDLRYQKTRQVGLSAWLKPKGT.

In some embodiments of the polymerases of the disclosure, the polymerase is a Pfu polymerase and comprises the nucleic acid sequence of

```
(SEQ ID NO: 7)
  1 atggctagcg ccattctgga tgtggactat atcaccgaag agggcaaacc ggttatacgt 61 ttatttaaga aagagaatgg taaattcaag atcgagcatg accgcacgtt ccgtccatac 121 atttacgcgt tgcttcggga tgatagcaaa attgaggaag tcaaaaagat caccggggaa 181 cgtcatggaa aaatagtaag aattgtggac gttgaaaaag tcgaaaagaa atttctgggc 241 aaaccgatca ctgtatggaa gctctatctg gaacatcctc aggatgtgcc cacaattcga 301 gaaaaagttc gtgagcaccc agccgtcgtg gatatatttg aatatgacat cccttttgca 361 aaacgctact taattgataa aggcctgatc ccgatggagg gggaagaaga acttaaaatt 421 ctggcttttg acatagaaac gctctatcat gagggagaag aatttggcaa aggtcccatc 481 attatgattt cttacgcgga tgagaacgaa gccaaggtaa tcacttggaa aaatattgac 541 ctgccgtacg ttgaagtggt cagttcagag cgggaaatga ttaaacgttt tttacgcatc 601 attagagaga agatccagat ataatcgtt acatataacg gcgactcctc cgattttcct 661 tacctggcaa aacgagctga aaaattgggt attaaactta ccatcgggcg tgacggatcg 721 gaaccgaaaa tgcaacgcat ggcgatatg acggcggtag aggtgaaagg tcggatacac 781 tttgatctgt atcatgtcat cacccgtact attaatctcc ccacatacac gttagaagcc 841 gtttatgagg caatattcgg caagccgaaa gaaaaagtgt acgctgacga aatcgcgaag 901 gcatgggaga gcggcgaaaa cctggagcgc gtagcaaaat attctatgga agatgctaaa
```

-continued

```
 961 gcgacctacg aattggggaa agaatttctt ccaatggaaa ttcagctgag tcgtttagtc 1021 ggacaacctc tgtgggacgt ttcacgctcc tcgactggca atctcgtgga gtggttcctg 1081 ttgagaaaag cctatgaacg aaacgaagta gcaccgaata aaccaagcga ggaagaatat 1141 cagcgtcgcc ttcgcgagtc ttacacaggt gggtttgtta aggaaccgga gaaggtctt 1201 tgggaaaaca tcgtgtattt agatttccgt gcgctgtacc ccagtattat aatcacccac 1261 aatgtctcac ctgacacgct caacttggaa ggttgcaaaa attatgatat tgctccgcaa 1321 gttggacata agttttgtaa agatattccg ggcttcatcc cgtccctgct tggtcactta 1381 ctggaagagc gccaaaaaat taagaccaaa atgaaagaga ctcaggatcc cattgaaaag 1441 atcctgctcg attaccggca aaaagccatt aaattgcttg caaactcgtt ttatgggtac 1501 tatggctatg cgaaggctcg ttggtactgc aaagaatgtg ccgagagcgt gacagcatgg 1561 ggtcgcaaat atatagaatt agtatggaag gagctggaag aaaaattcgg attcaaagtc 1621 ctgtacatcg atacggatgg cctctatgcg accattcctg gtggggagtc tgaagaaatc 1681 aagaaaaaag ccttggaatt cgttaagtac attaatagta aattaccggg actgcttgaa 1741 ctggagtatg aaggcttcta caaaagaggt tttttcgtta ctaagaaacg atatgccgta 1801 atagatgaag aggggaaagt catcacacgt ggcctcgaga ttgttcgccg ggactggtca 1861 gagatagcaa aggaaacgca ggcgcgcgtg ctcgaaacca tcttgaaaca tggtgatgta 1921 gaggaagccg tccgcattgt taaagaggtg atccagaagt tagcaaacta tgaaattcca 1981 ccggaaaaac tggcgatata cgagcaaatc actcgtcccc ttcacgaata taaagctatt 2041 ggacctcatg tagccgtcgc gaagaaactg gctgcaaaag gcgttaagat aaaaccaggt 2101 atggtgatcg ggtacattgt actccgcggc gacggtccga tttccaatag agccatcttg 2161 gcggaggaat atgatcctaa aaagcataaa tacgacgctg aatattacat tgagaaccag 2221 gtcttgccgg cagttctgcg gatacttgaa ggatttggct atcgtaaaga agatctgcgc 2281 tatcaaaaga cgcgacaggt gggtctgact agctggttga atatcaaaaa atcgtaa.
```

In some embodiments of the polymerases of the disclosure, the polymerase is a Pfu polymerase and comprises the amino acid sequence of (SEQ ID NO: 8)
MASAILDVDYITEEGKPVIRLFKKENGKFKIEHDRTFRPYIYALLRDDSK

IEEVKKITGERHGKIVRIVDVEKVEKKFLGKPITVWKLYLEHPQDVPTIR

EKVREHPAVVDIFEYDIPFAKRYLIDKGLIPMEGEEELKILAFDIETLYH

EGEEFGKGPIIMISYADENEAKVITWKNIDLPYVEVVSSEREMIKRFLRI

IREKDPDIIVTYNGDSFDFPYLAKRAEKLGIKLTIGRDGSEPKMQRIGDM

TAVEVKGRIHFDLYHVITRTINLPTYTLEAVYEAIFGKPKEKVYADEIAK

AWESGENLERVAKYSMEDAKATYELGKEFLPMEIQLSRLVGQPLWDVSRS

STGNLVEWFLLRKAYERNEVAPNKPSEEEYQRRLRESYTGGFVKEPEKGL

WENIVYLDFRALYPSIIITHNVSPDTLNLEGCKNYDIAPQVGHKFCKDIP

GFIPSLLGHLLEERQKIKTKMKETQDPIEKILLDYRQKAIKLLANSFYGY

YGYAKARWYCKECAESVTAWGRKYIELVWKELEEKFGFKVLYIDTDGLYA

TIPGGESEEIKKKALEFVKYINSKLPGLLELEYEGFYKRGFFVTKKRYAV

IDEEGKVITRGLEIVRRDWSEIAKETQARVLETILKHGDVEEAVRIVKEV

IQKLANYEIPPEKLAIYEQITRPLHEYKAIGPHVAVAKKLAAKGVKIKPG

MVIGYIVLRGDGPISNRAILAEEYDPKKHKYDAEYYIENQVLPAVLRILE

GFGYRKEDLRYQKTRQVGLTSWLNIKKS.

The disclosure provides methods of making a DNA fragment library from ssDNA comprising: contacting the ssDNA composition or the isolated ssDNA composition of disclosure, with a forward primer, a reverse primer, a polymerase and a plurality of dNTPs under conditions sufficient for amplification of at least one ssDNA or a portion thereof, wherein the ssDNA comprises a first amplification product and wherein a second amplification product comprise a second DNA strand, wherein the second DNA strand is complementary to the ssDNA and/or the first amplification product.

In some embodiments of the methods of making a making a DNA fragment library from ssDNA, the forward primer hybridizes with a sequence within the first adaptor sequence. In some embodiments, the forward primer hybridizes with a sequence within a sequence identical to a sequence of the TSO. In some embodiments, the reverse primer hybridizes with a sequence within the template sequence.

In some embodiments of the methods of making a making a DNA fragment library from ssDNA, the reverse primer comprises a linking sequence and an SID sequence. In some embodiments, the reverse primer comprises a linking sequence and a UID sequence or a SID sequence. In some embodiments, the linking sequence comprises a sequence having at least 50% identity or complementarity to a sequence of a primer, an adaptor, or a component of an array. In some embodiments, the linking sequence comprises a sequence having at least 50%, 55%, 60%, 65%, 70%, 75%, 80%, 85%, 90%, 95%, 97%, 99%, 100% or any percentage in between identity or complementarity to a sequence of a primer, an adaptor, or a component of an array. In some embodiments, the SID sequence comprises a random sequence. In some embodiments, the UID sequence or the SID sequence comprises a random sequence. In some embodiments, wherein the SID sequence comprises a pre-determined sequence. In some embodiments, the UID sequence or the SID sequence comprises a pre-determined sequence. In some embodiments, the SID comprises a sequence between 1 and 20 nucleotides, inclusive of the endpoints. In some embodiments, the UID sequence or the SID sequence comprises a sequence between 1 and 20 nucleotides, inclusive of the endpoints. In some embodiments, the SID comprises a sequence between 2 and 12 nucleotides, inclusive of the endpoints. In some embodiments, the UID sequence or the SID sequence comprises a sequence between 2 and 12 nucleotides, inclusive of the endpoints. In some embodiments, the SID comprises a sequence between 4 and 10 nucleotides, inclusive of the endpoints. In some embodiments, the UID sequence or the SID sequence comprises a sequence between 4 and 10 nucleotides, inclusive of the endpoints. In some embodiments, the SID sequence comprises eight nucleotides. In some embodiments, the UID sequence or the SID sequence comprises eight nucleotides. In some embodiments, the SID sequence and the UID sequence are not identical. In some embodiments, the UID sequence or the SID sequence of a primer and the UID sequence, the SID sequence or the UMI sequence of the TSO are not identical.

In some embodiments of the methods of making a making a DNA fragment library from ssDNA, the first amplification product comprises a sequence complementary to a sequence of the reverse primer. In some embodiments, the reverse primer comprise a SID sequence and wherein the first amplification product comprises a sequence complementary to the SID sequence. In some embodiments, the reverse primer comprises a UID sequence or a SID sequence and wherein the first amplification product comprises a sequence complementary to the UID sequence or the SID sequence. In some embodiments, the reverse primer comprises a linking sequence and wherein the first amplification product comprises a sequence complementary to the linking sequence.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is a graph of real time PCR reaction products amplified from a 153 basepair (bp) DNA template that had adaptors added to either end of the template by the template switching reaction of the disclosure. Top panels: template DNA reacted with the template switching oligo (TSO) in the presence of MMLV RT (+RT). Bottom panels: control reaction with no MMLV RT (−RT). On the x-axis is shown the number of reaction cycles from 0 to 35 in increments of 5 (left hand panels), and 80 to 90 in increments of 5 (right hand panels). On the y-axis, fluorescence is shown from 0 to 100 in increments of 10 (both panels). A schematic of the template with the adaptor (hatched box) and the PCR primers (arrows) used in the reaction is shown beneath the panels. In this PCR reaction, one PCR primer (left) hybridizes to the template DNA sequence, while the other PCR primer (right) is specific to the TSO (hatched box).

FIG. 3 is a graph of real time PCR reaction products amplified from a 153 bp DNA template that had adaptors added to either end of the template by the template switching reaction of the disclosure. Top panels: template DNA reacted with the (TSO) in the presence of MMLV RT (+RT). Bottom panels: control reaction with no MMLV RT (−RT). On the x-axis is shown the number of reaction cycles from 0 to 35 in increments of 5 (left hand panels), and 80 to 90 in increments of 5 (right hand panels). On the y-axis, fluorescence is shown from 0 to 100 in increments of 10 (both panels). A schematic of the template with the adaptor (hatched box) and the PCR primers (arrows) used in the reaction is shown below the panels. In this PCR reaction, both PCR primers (left and right) hybridize to the template DNA sequence.

1259; dark blue) and i7 index primer (1258; green; complementary to 1259; dark blue+1244; yellow) adds the i5 (1248; yellow) and i7 (1244; yellow) sequences. Addition of indexing sequences occurs only in the final round of PCR (1262) with this strategy, not in the first round of PCR (1260) or the template switching reaction.

Figure 12:
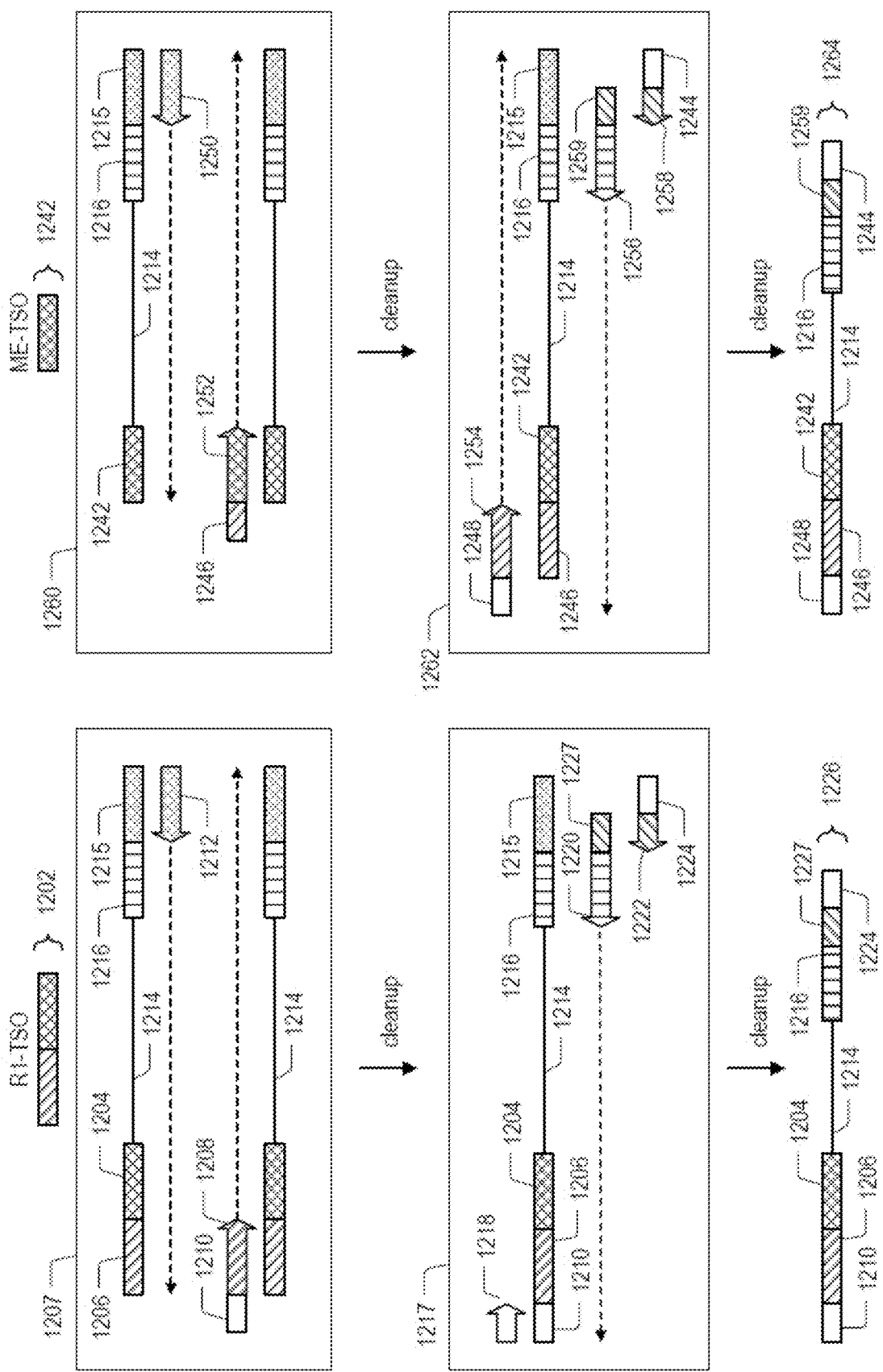
FIG. 12 is a diagram showing two alternative TSO and the associated PCR primers for two rounds of multiplexed PCR. Both strategies lead to the product shown at the bottom of FIG. 12. In the left hand panels (1207 (first round PCR step) and 1217 (second round PCR step)), an extended R1-TSO (1202) is added to the template (1214, comprising a region of interest 1216) by the template switching mechanism. In some embodiments, R1-TSO comprises both a sequence 1204 complementary to the poly(C) sequence added by the MMLV RT and an extended primer sequence 1206, which, in some embodiments, includes a UID sequence. An i5 index primer (1208, which optionally contains a UID or SID (1210)) binds to the R1-TSO and adds additional sequence to the 5' end of the template in a PCR reaction with a gene or template specific reverse primer (outerR primer; 1212, complementary to a sequence 1215). In a second round of PCR (1217), the P1a forward primer (1218) binds to the added i5 index primer sequence (1208+1210), while an inner reverse gene/template specific primer (NexR; 1220+1227) adds the additional i7 index sequence (e.g., 1222+a UID or SID (1224)). In the right hand panels (1260 (first round PCR step) and 1262 (second round PCR step)), the TSO, a minimal ME-TSO (1242), is added to the template (1214, comprising a region of interest 1216). A first round of PCR (1260) with an R1 forward primer (1252+1246) and the outerR primer ((1250); complementary to sequence 1215) adds the R1 sequence (1246) to the 5' end. A second round of PCR (1262) with the i5 index primer (1248+1254) and the NexR primer (1256 (which is complementary to 1216)+1259) and i7 index primer (1258 (complementary to 1259)+1244) adds the i5 (1248) and i7 (1244) sequences. Addition of indexing sequences occurs only in the final round of PCR (1262) with this strategy, not in the first round of PCR (1260) or the template switching reaction. A diagram of the final PCR product produced by the two rounds of multiplex PCR is shown at the bottom of FIG. 12. The final PCR product (1226 for the left-hand process)comprises or consists of, from 5' to 3', of an i5 index sequence (1210), the R1 sequence (1206), the adaptor sequence (1204), the template (1214), the template specific reverse primer binding sequences (1216+1227) and the i7 index sequence (1224). The final PCR product (1264 for the right-hand process) comprises or consists of, from 5' to 3', of an i5 index sequence (1248), the R1 sequence (1246), the adaptor sequence (1242), the template (1214), the template specific reverse primer binding sequences (1216+1259) and the i7 index sequence (1244).
Figure 13A:
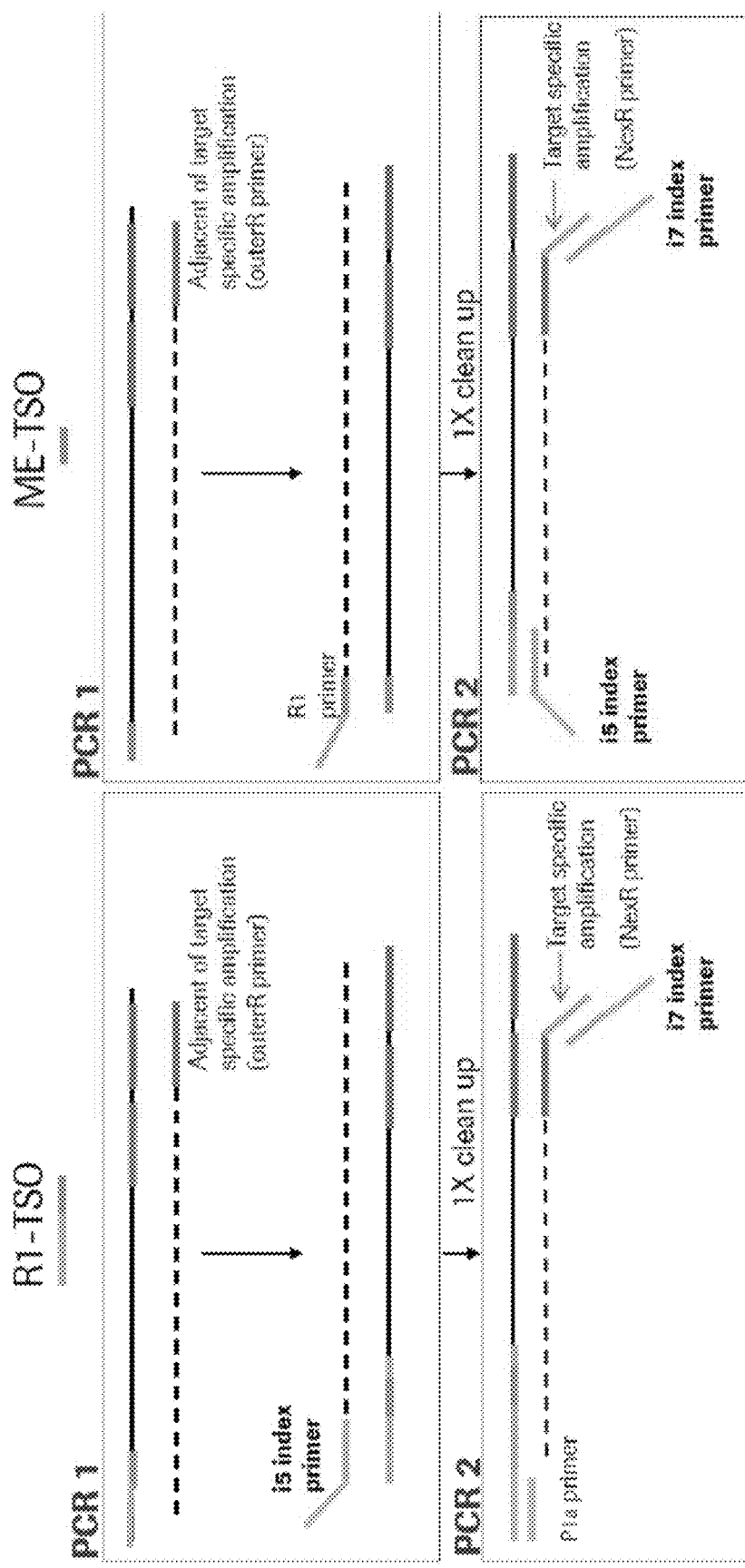
FIG. 13A is a diagram showing two alternative TSO and the associated PCR primers for two rounds of multiplexed PCR. Both strategies lead to the product shown in FIG. 13B. In the left hand panels (1207 (first round PCR step) and 1217 (second round PCR step)), an extended R1-TSO (1202; green+light blue) is added to the template (1214, black line) comprising a region of interest (1216; magenta) by the template switching mechanism. In some embodiments, R1-TSO comprises both a sequence 1204 (light blue) complementary to the poly(C) sequence added by the MMLV RT and an extended primer sequence 1206 (green), which, in some embodiments, includes a UID sequence (not numbered). An i5 index primer (1208; green+yellow) that optionally contains a UID or SID (1210; yellow)) binds to the R1-TSO and adds additional sequence to the 5' end of the template in a PCR reaction with a gene or template specific reverse primer (outerR primer; 1212 (dark blue) complementary to a sequence 1215 (dark blue)). In a second round of PCR (PCR 2, 1217), the P1a forward primer (1218, yellow) binds to the added i5 index primer sequence (1208; green+1210; yellow), while an inner reverse gene/template specific primer (NexR; 1220; magenta+1227; green) adds the additional i7 index sequence (e.g., 1222 (green) a UID or SID (1224; yellow)). In the right hand panels (1260 (first round PCR step) and 1262 (second round PCR step)), the TSO, a minimal ME-TSO (1242; light blue), is added to the template (1214 (black line), comprising a region of interesting 1216; magenta). A first round of PCR (1260) with an R1 forward primer (1252; light blue+1246; green) and the outerR primer ((1250; dark blue); complementary to sequence 1215; dark blue) adds the R1 sequence (1246; green) to the 5' end. A second round of PCR (1262) with the i5 index primer (1248; yellow+1254; green) and the NexR primer (1256; magenta; complementary to 1216; magenta+
Figure 13B:
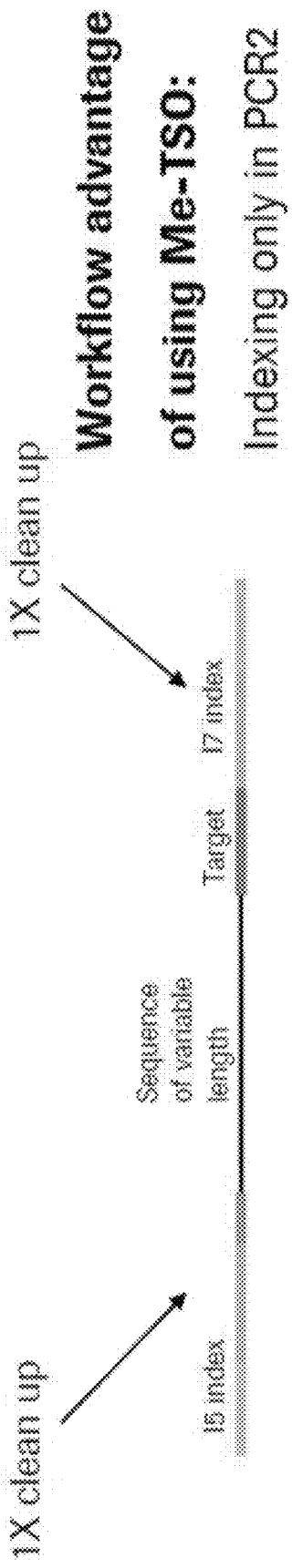

FIG. 13B is a diagram of the final PCR product produced (1226) by the two rounds of multiplex PCR shown in FIG. 12 and 13A. The final PCR product consists, from 5' to 3', of an i5 index sequence (1248 or 1210; yellow), the R1 sequence (1246 or 1206; green), the adaptor sequence (1242 or 1204; light blue), the template (1214, black line), the template specific reverse primer binding sequences (1216; magenta+1259 or 1227; green) and the i7 index sequence (1244 or 1224; yellow).

Figure 14:
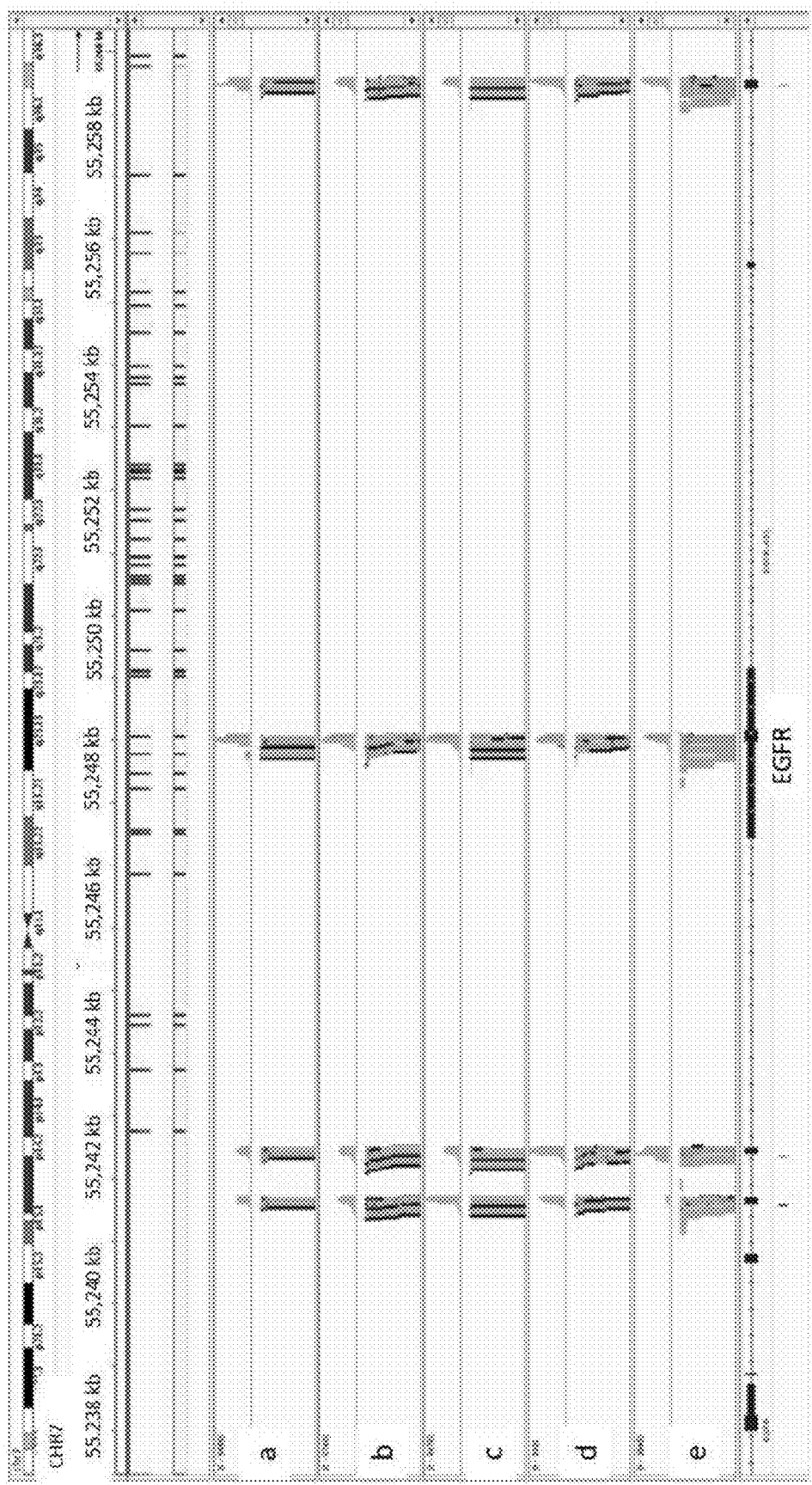

FIG. 14 is an alignment of reads from several template switching libraries with 23 kilobases (kb) of the EGFR locus. Libraries were produced by amplifying different template switched materials with the 31 primer panel. 10 ng of starting DNA that had been either Covaris sheared and end repaired or enzymatically fragmented using the Kapa Frag enzyme, was used in a template switching reaction with either the R1-TSO or the ME-TSO TSO of FIG. 12. The resulting product was either SPRI cleaned or used directly for a first round of multiplex PCR to produce the sequencing libraries. At top, a diagram of human chromosome 7, with the EGFR locus shown as a red bar. Locations are shown below in kb, from left to right, 55238 kb, 55240 kb, 55242 kb, 55246 kb, 55248 kb, 55250 kb, 55252 kb, 55254 kb, 55256 kb, 55258 kb, 55260 kb. Genotype NA 12878 (Genome in a Bottle consortium, HG001) variant data is shown in the two tracks below the DNA ruler. Additional tracks showing alignment data include, in order from top to bottom: Covaris sheared and end repaired DNA, ME-TSO template switch reaction, cleaned up before PCR; Covaris sheared and end repaired DNA, R1-TSO template switch reaction, no cleanup, direct to PCR; enzymatically fragmented DNA, R1-TSO template switch reaction, cleaned up prior to PCR reaction; enzymatically fragmented DNA, R1-TSO template switch reaction, no cleanup, direct to PCR; positive control reaction using a tagmentation-based anchored PCR technique (which does not utilize template switching), performed with the same gene specific primer set. At bottom are shown the annotated EGFR gene and the location of EGFR-specific primers.

Figure 15:
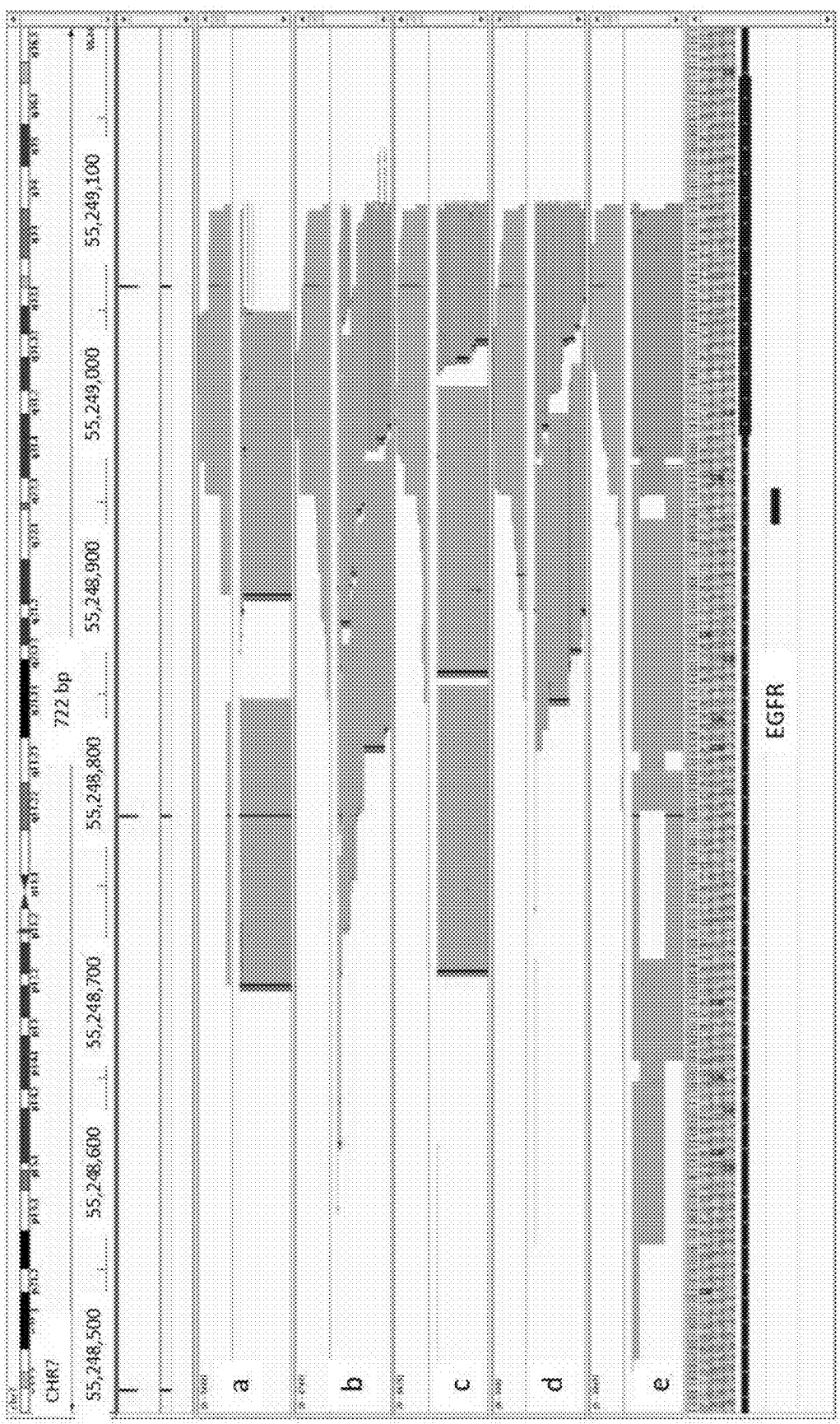

FIG. 15 is an alignment of reads from a template switching libraries with 722 bp of the EGFR locus. At top, a diagram of human chromosome 7, with the EGFR locus shown as a red bar. Genomic locations are shown below in bp, from left to right from 55,248,500 to 55,249,200 in increments of 100 bp. Genotype NA 12878 (Genome in a Bottle consortium, HG001) variant data is shown in the two tracks below the DNA ruler. Additional tracks showing alignment data include, in order from top to bottom: Covaris sheared and end repaired DNA, ME-TSO template switch reaction, cleaned up before PCR; Covaris sheared and end repaired DNA, R1-TSO template switch reaction, no cleanup, direct to PCR; enzymatically fragmented DNA, R1-TSO template switch reaction, cleaned up prior to PCR reaction; enzymatically fragmented DNA, R1-TSO template switch reaction, no cleanup, direct to PCR; positive control reaction using a tagmentation-based anchored PCR technique (which does not utilize template switching), performed with the same gene specific primer set. At bottom are shown the annotated EGFR gene and the location of EGFR specific primers.

Figure 16:
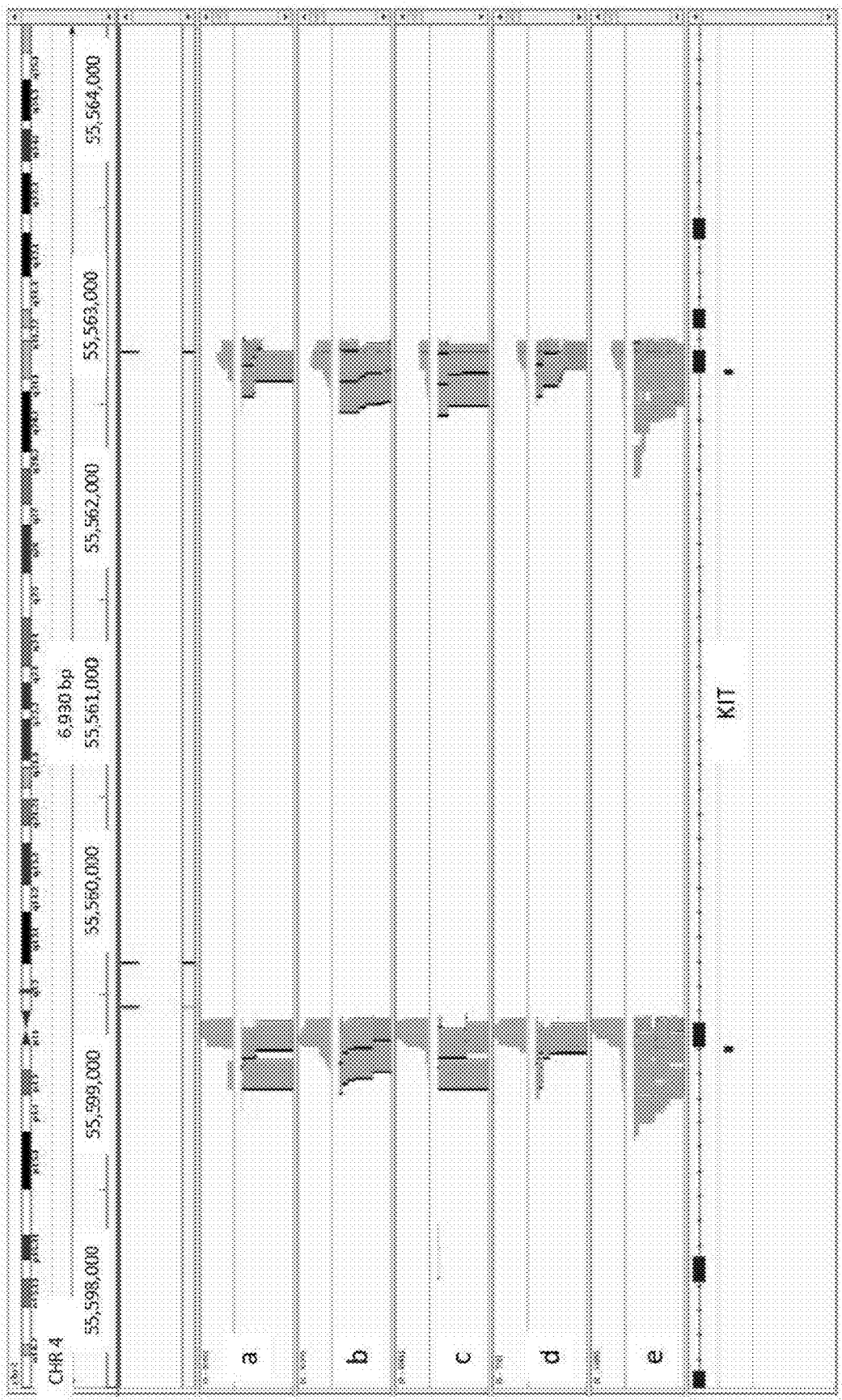

FIG. 16 is an alignment of reads from template switching libraries with 6,930 bp of the Kit locus. At top, a diagram of human chromosome 4, with the Kit locus shown as a red bar. Genomic locations are shown below in bp, from left to right from 55,598,000 to 55,604,000 in increments of 1000 bp. Genotype NA 12878 (Genome in a Bottle consortium, HG001) variant data is shown in the two tracks below the DNA ruler. Additional tracks showing alignment data include, in order from top to bottom: Covaris sheared and end repaired DNA, ME-TSO template switch reaction, cleaned up before PCR; Covaris sheared and end repaired DNA, R1-TSO template switch reaction, no cleanup, direct to PCR; enzymatically fragmented DNA, R1-TSO template switch reaction, cleaned up prior to PCR reaction; enzymatically fragmented DNA, R1-TSO template switch reaction, no cleanup, direct to PCR; positive control reaction using a tagmentation-based anchored PCR technique (which does not utilize template switching), performed with the same gene specific primer set. At bottom are shown the annotated Kit gene and the location of Kit specific primers.

Figure 17:
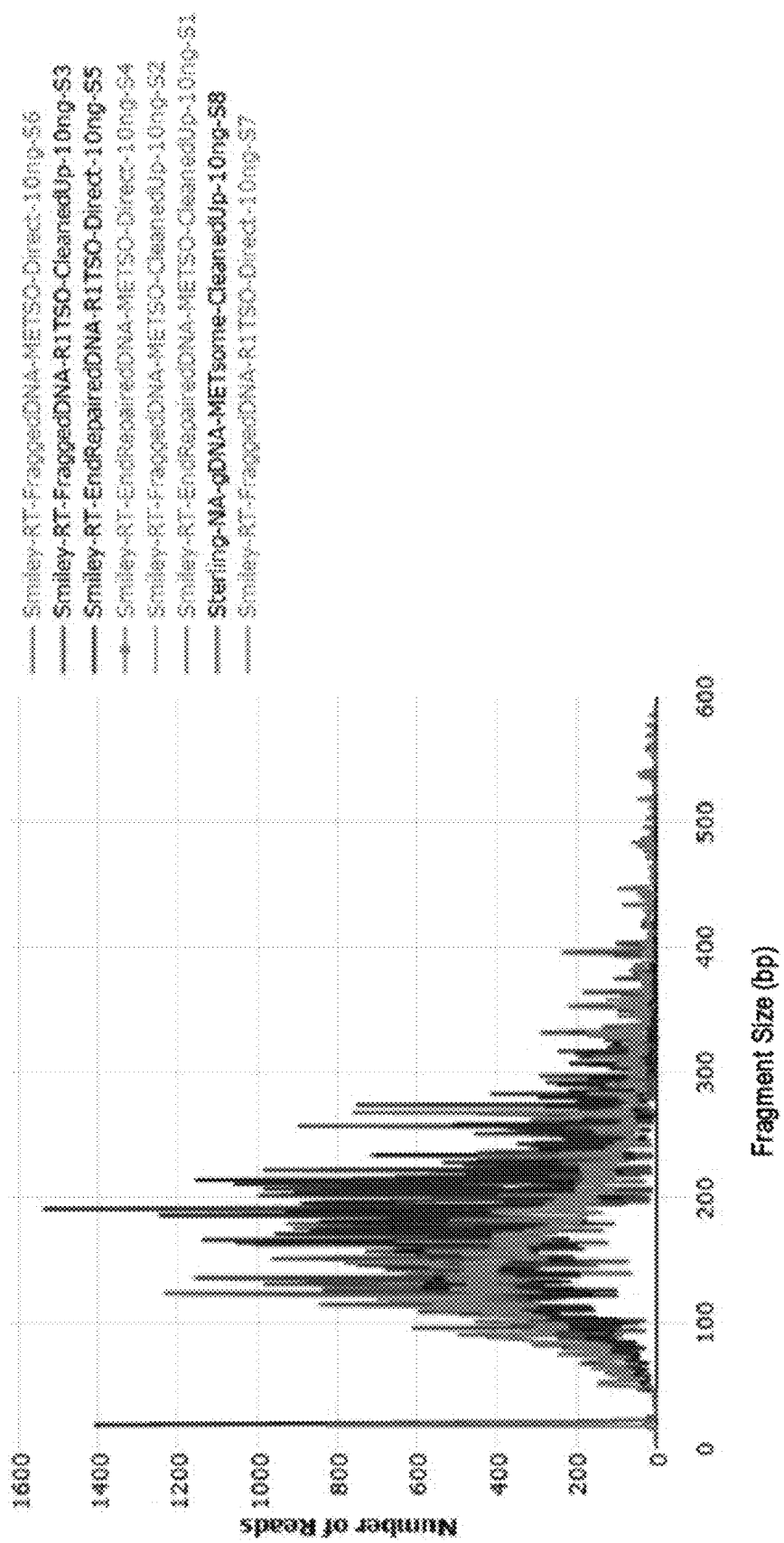

FIG. 17 is a chart of the size distribution of fragments of the libraries produced by amplifying different template switched materials with the 31 primer panel. On the x-axis, fragment size in bp. On the y-axis, number of reads.

Figure 18:
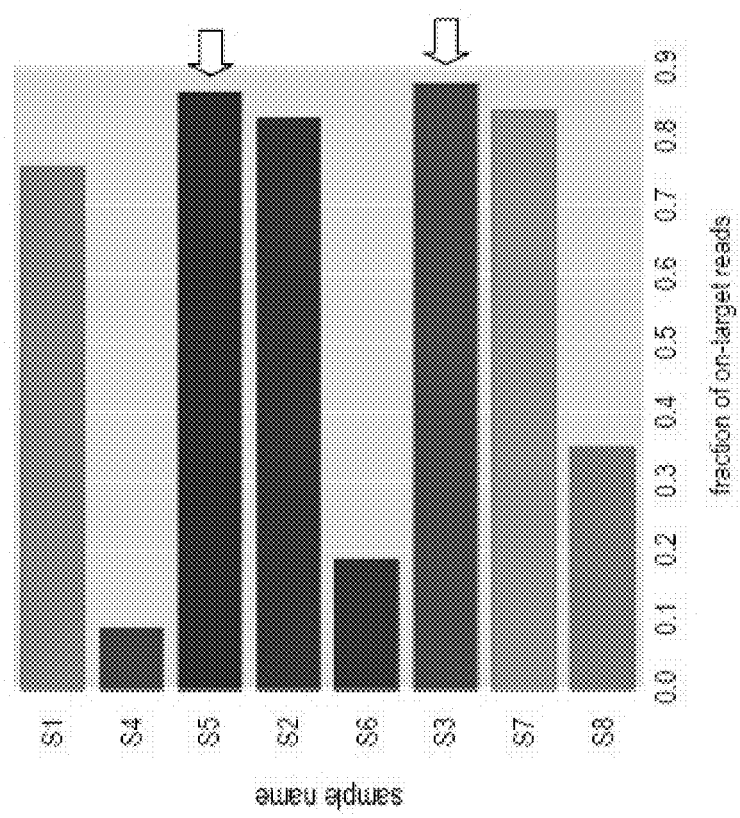

FIG. 18 is a bar chart showing the on-target rates for the template switching libraries. On the x-axis, the fraction of reads on-target, from 0 (left) to 0.9 (right) in increments of 0.1. On the y-axis, individual libraries. The libraries are, in order from top to bottom: (S1) Covaris sheared and end repaired DNA reacted with ME-TSO and cleaned up prior to the PCR, (S4) Covaris sheared and end repaired DNA reacted with the ME-TSO and added directly to the PCR, (S5) Covaris sheared and end repaired DNA reacted with the R1-TSO and added directly to the PCR, (S2) enzymatically fragmented DNA reacted with the ME-TSO and cleaned up prior to the PCR, (S6) enzymatically fragmented DNA reacted with the ME-TSO added directly to the PCR, (S3) enzymatically fragmented DNA reacted with the R1-TSO and cleaned up prior to the PCR, (S7) enzymatically fragmented DNA reacted with the R1-TSO and added directly to the PCR, (S8) positive control reaction using a tagmentation-based anchored PCR technique (which does not utilize template switching), performed with the same gene specific primer set.

Figure 19:
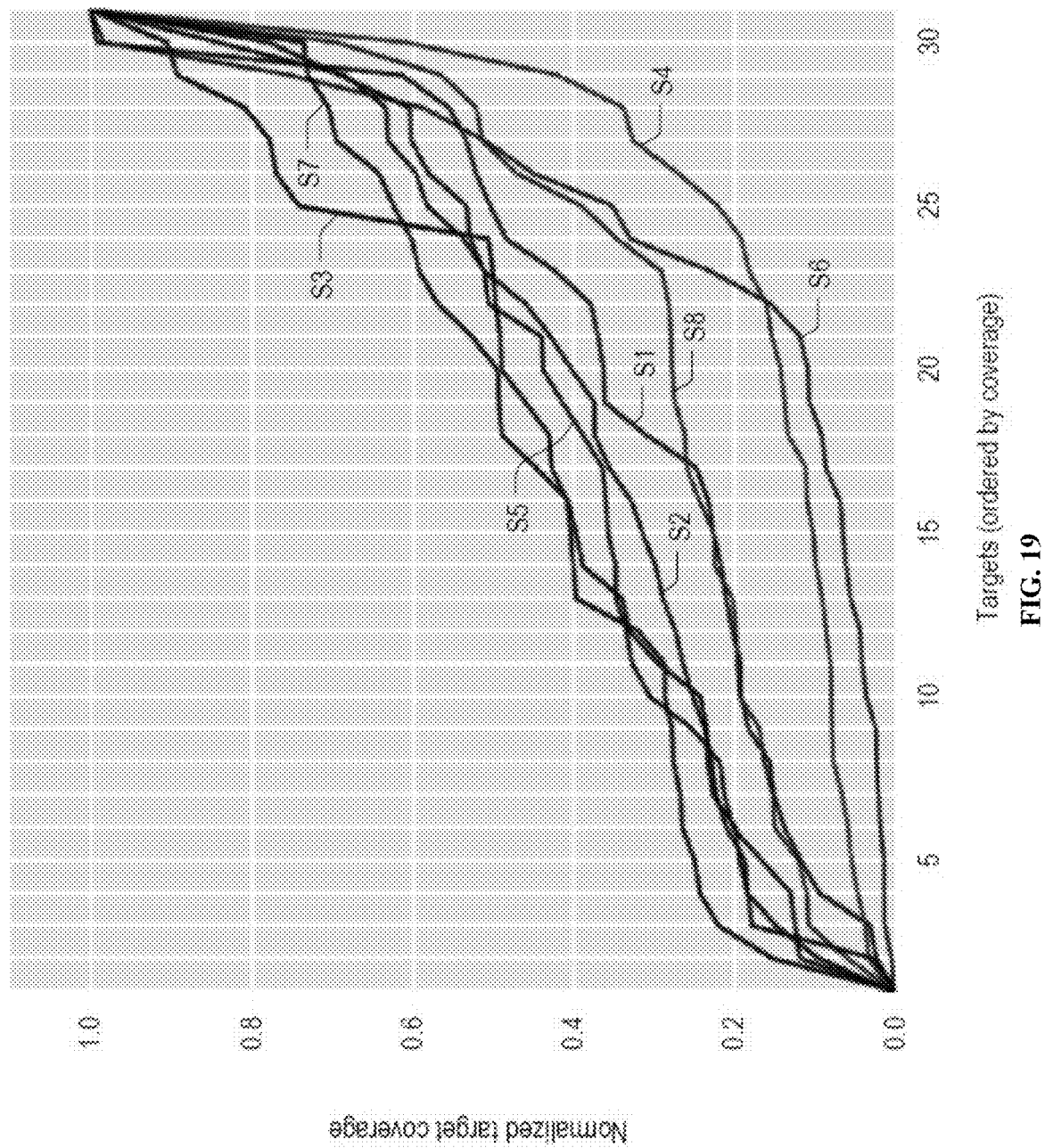

FIG. 19 is a graph showing panel coverage uniformity for the template switching libraries generated using the 31 primer panel. On the x-axis, individual loci in the panel ordered from least (left) to most (right) coverage. On the y-axis, normalized target coverage. Libraries shown, in the order of the curves from top to bottom at locus 20 are: Covaris sheared and end repaired DNA reacted with the R1-TSO and cleaned up prior to the PCR (S3), enzymatically fragmented DNA reacted with the R1-TSO and added directly to the PCR (S7), Covaris sheared and end repaired DNA reacted with the R1-TSO and added directly to the PCR (S5), enzymatically fragmented DNA reacted with the ME-TSO cleaned up prior to the PCR (S2), Covaris sheared and end repaired DNA reacted with the ME-TSO and cleaned up prior to the PCR (Si), positive control reaction using a tagmentation-based anchored PCR technique (which does not utilize template switching), performed with the same gene specific primer set (S8), Covaris sheared and end repaired DNA reacted with the ME-TSO and added directly to the PCR (S4), fragmented DNA reacted with the ME-TSO and added directly to the PCR (S6).

Figure 20:
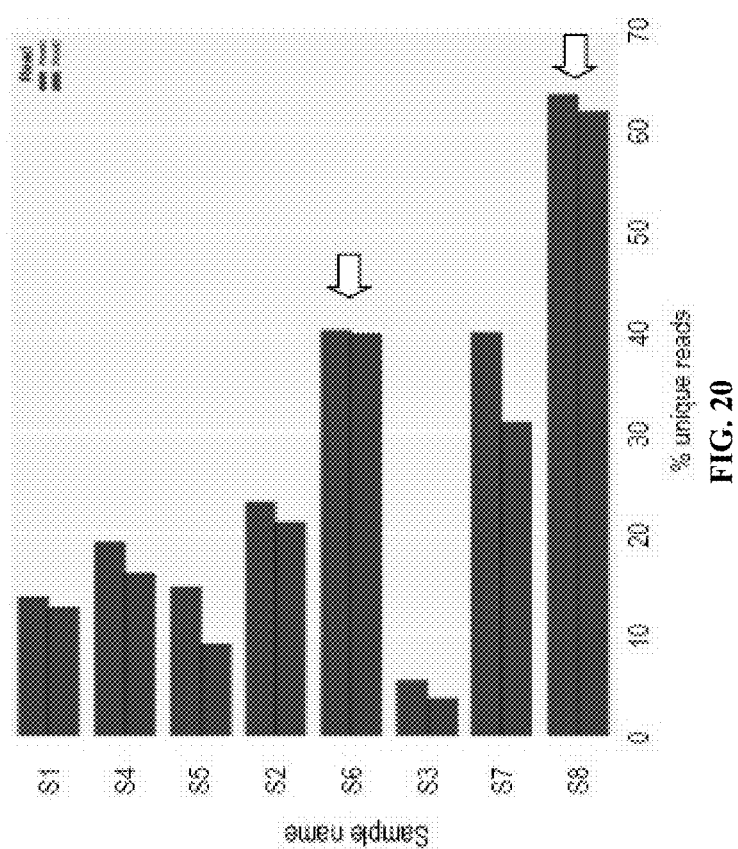

FIG. 20 is a bar chart showing the unique read rate in template switching libraries generated using the 31 primer panel on template switched products. On the x-axis is shown the percent of unique reads, from 0 to 70% in increments of 10%. On the y-axis, the various libraries. The libraries are, in order from top to bottom: (S1) Covaris sheared and end repaired DNA reacted with ME-TSO and cleaned up prior to the PCR, (S4) Covaris sheared and end repaired DNA reacted with the ME-TSO and added directly to the PCR, (S5) Covaris sheared and end repaired DNA reacted with the R1-TSO and added directly to the PCR, (S2) enzymatically fragmented DNA reacted with the ME-TSO and cleaned up prior to the PCR, (S6) enzymatically fragmented DNA reacted with the ME-TSO added directly to the PCR, (S3) enzymatically fragmented DNA reacted with the R1-TSO and cleaned up prior to the PCR, (S7) enzymatically fragmented DNA reacted with the R1-TSO and added directly to the PCR, (S8, "Sterling") positive control reaction using a tagmentation-based anchored PCR technique (which does not utilize template switching), performed with the same gene specific primer set.

Figure 21:
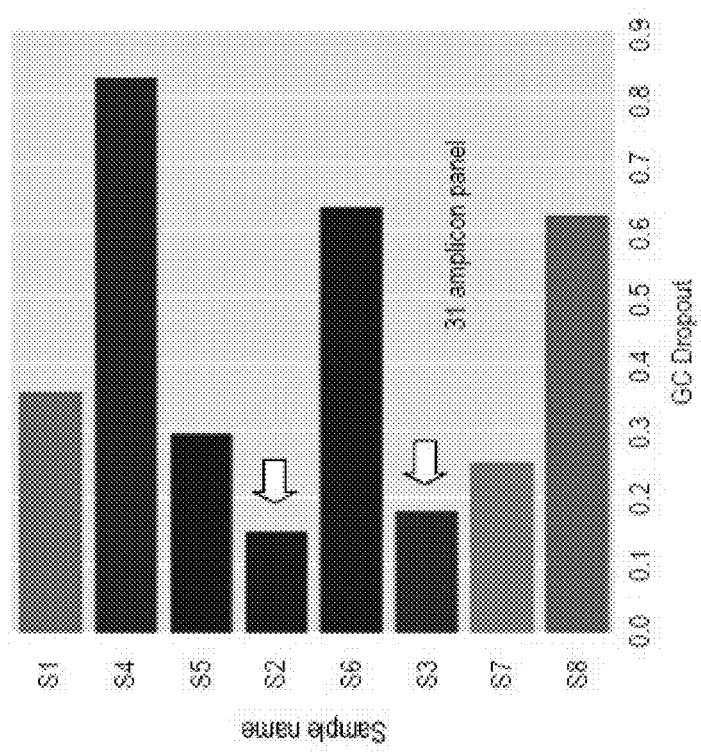

FIG. 21 is a bar chart showing the GC dropout metric (calculated using the CollectGCBiasMetrics program from Picard Tools, github.com/broadinstitute/picard) for template switching libraries generated using the 31 primer panel on template switched products. On the x-axis, GC dropout from 0 to 9 in increments of 1. On the y-axis, the various libraries, in order from top to bottom: (S1) Covaris sheared and end repaired DNA reacted with ME-TSO and cleaned up prior to the PCR, (S4) Covaris sheared and end repaired DNA reacted with the ME-TSO and added directly to the PCR, (S5) Covaris sheared and end repaired DNA reacted with the R1-TSO and added directly to the PCR, (S2) enzymatically fragmented DNA reacted with the ME-TSO and cleaned up prior to the PCR, (S6) enzymatically fragmented DNA reacted with the ME-TSO added directly to the PCR, (S3) enzymatically fragmented DNA reacted with the R1-TSO and cleaned up prior to the PCR, (S7) enzymatically fragmented DNA reacted with the R1-TSO and added directly to the PCR, (S8, "Sterling") positive control reaction using a tagmentation-based anchored PCR technique (which does not utilize template switching), performed with the same gene specific primer set.

Figure 22:
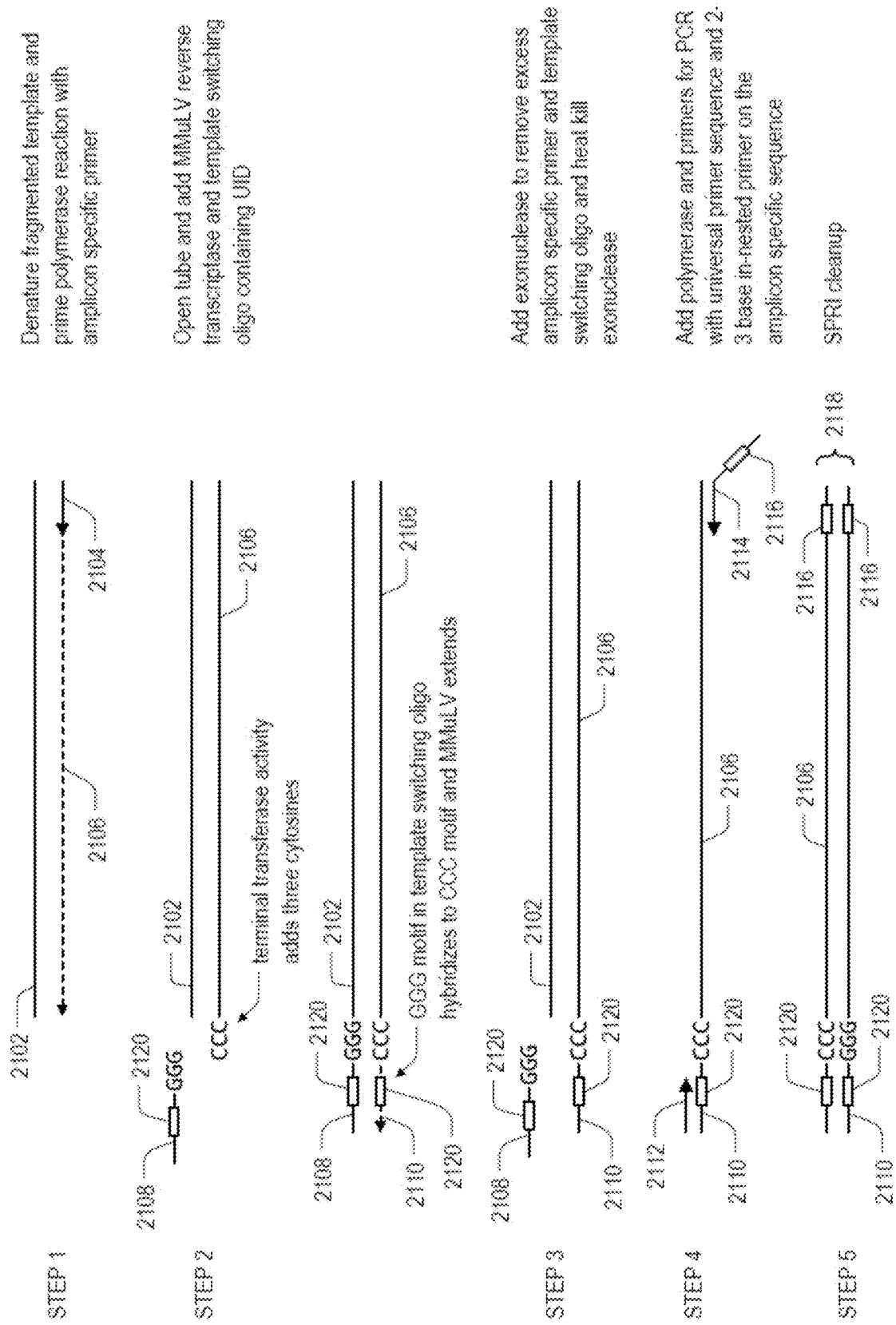

FIG. 22 is a drawing of a template switching method starting with a single stranded DNA template, whereby the extension and template switching reactions can be uncoupled, and adaptor sequences can be added to either end of a template sequence. The method comprises the steps of denaturing a fragmented double stranded DNA (dsDNA) to provide an at least partially single stranded ssDNA (2102), annealing a primer (2104) to the ssDNA to form a ssDNA:primer complex and extending the ssDNA:primer complex using a high-fidelity DNA polymerase (e.g. Kapa HiFi, SEQ ID NO: 1 or 3, step 1) to produce an extension product (2106). The extension product (2106), a TSO (2108) and an enzyme capable of terminal transferase activity and template switching (e.g. MMLV RT) are contacted under conditions sufficient for terminal transferase and template switching activity (the reaction is incubated at a temperature where the DNA polymerase is mostly inactive but the MMLV RT is active, resulting in the addition of a 3' adaptor (2110) to the synthesized strand). The MMLV RT then switches strands to extend the adaptor sequence (2110) complementary to the TSO (2108) in the 5' to 3' direction (step 2). The addition of an exonuclease removed excess amplicon, TSO, and primers. The exonuclease is neutralized either by heating the reaction or by purifying the reacted template DNA (2102) (step 3). Finally, a polymerase and PCR primers (2112) and (2114) that hybridize to the template sequence (2106) and the TSO (2110), which optionally contain SIDs (2116), are added to produce a dsDNA (2118) ready for sequencing (step 4). This method includes a single round of PCR to produce a sequencing ready PCR product comprising a UID (2120) provided by the TSO (2110). This method is expected to increase specificity by ensuring that only (specifically primed and extended) products are subjected to template switching.

Figure 23:
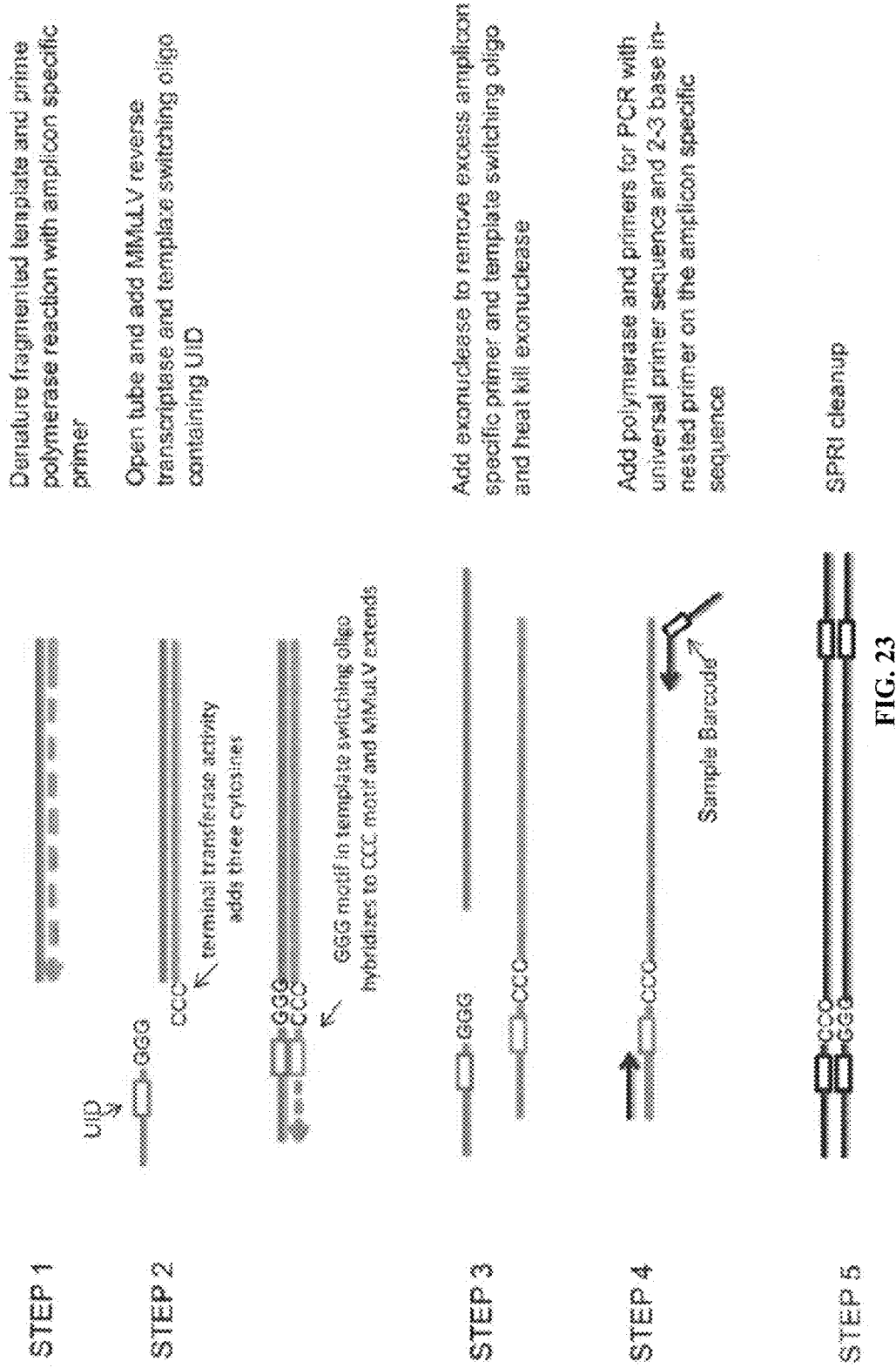

FIG. 23 is a drawing of a template switching method starting with a single stranded DNA template, whereby the extension and template switching reactions can be uncoupled, and adaptor sequences can be added to either end of a template sequence. The method comprises the steps of denaturing a fragmented double stranded DNA (dsDNA) to provide an at least partially single stranded ssDNA (2102; blue line), annealing a primer (2104; red) to the ssDNA to form a ssDNA:primer complex and extending the ssDNA:primer complex using a high-fidelity DNA polymerase (e.g. Kapa HiFi, SEQ ID NO: 1 or 3, step 1) to produce an extension product (2106; dashed red line). The extension product (2106), a TSO (2108, blue line comprising a UMI (2120; blue rectangle)) and an enzyme capable of terminal transferase activity and template switching (e.g. MMLV RT) are contacted under conditions sufficient for terminal transferase and template switching activity (the reaction is incubated at a temperature where the DNA polymerase is mostly inactive but the MMLV RT is active, resulting in the addition of a 3' adaptor (2110; red line and box at step 3 that comprises a UMI (Unique Molecular Identifier, 2120)) to the synthesized strand). The MMLV RT then switches strands to extend the adaptor sequence (2110) complementary to the TSO (2108) in the 5' to 3' direction (step 2). The addition of an exonuclease removed excess amplicon, TSO, and primers. The exonuclease is neutralized either by heating the reaction or by purifying the reacted template DNA (2102) (step 3). Finally, a polymerase and PCR primers (2112; black arrow) and (2114; black arrow comprising SID (2116, black rectangle)) that hybridize to the template sequence (2106) and the TSO (2110), which optionally contain SIDs (2116), are added to produce a dsDNA (2118) ready for sequencing (step 4). This method includes a single round of PCR to produce a sequencing ready PCR product comprising a UID (2120) provided by the TSO (2110). This method is expected to increase specificity by ensuring that only (specifically primed and extended) products are subjected to template switching.

Figure 24:
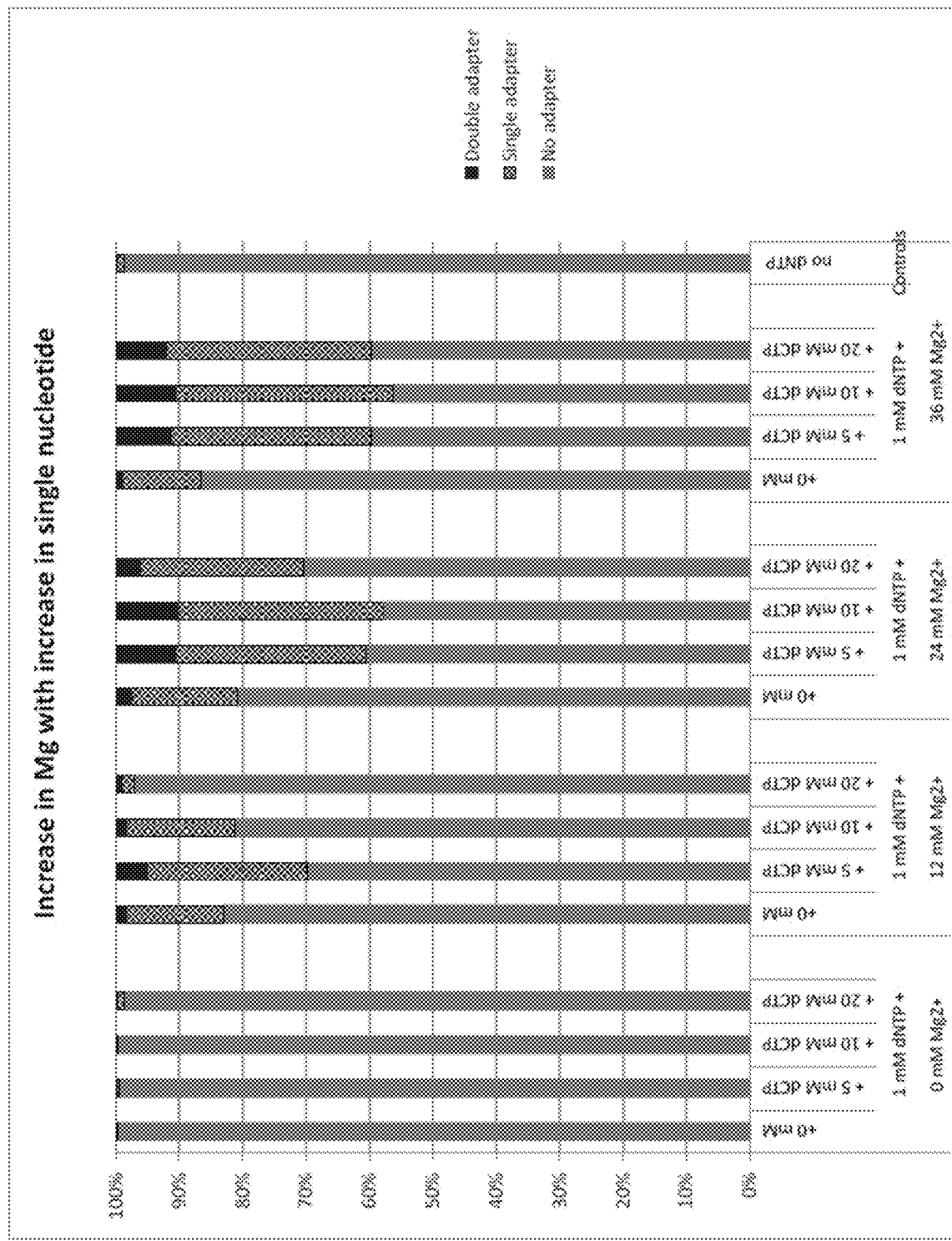

FIG. 24 is a graph showing the ratio of species to the total molarity wherein the species are: 1) the dsDNA amplicon with no adapter addition (no adapter), 2) the amplicon with an adapter added to one end (single adapter), 3) and the amplicon with an adapter added on both ends (double adapter). The y-axis reflects percent of each species in each sample. The x-axis reflects reaction conditions of 1 mM of each dNTP, with an additional dCTP added at 0 mM, 5 mM, 10 mM, or 20 mM. Additionally Mg2+ concentration was included at 0 mM, 12 mM, 24 mM, or 36 mM.

Figure 25:
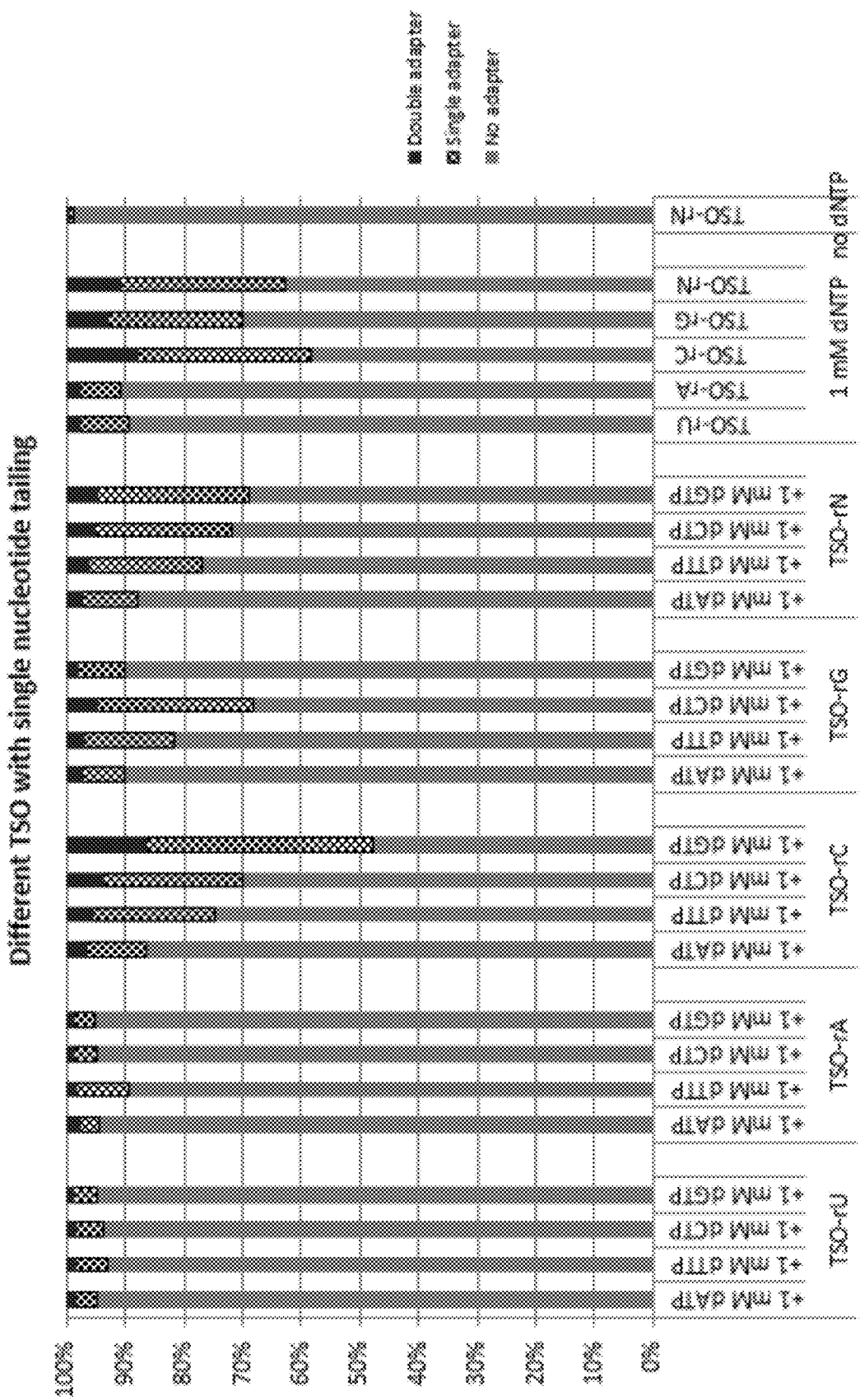

FIG. 25 is a graph showing the ratio of species to the total molarity wherein the species are: 1) the dsDNA amplicon with no adapter addition (no adapter), 2) the amplicon with an adapter added to one end (single adapter), 3) and the amplicon with an adapter added on both ends (double adapter). The y-axis reflects percent of each species in each sample. The x-axis reflects reaction conditions wherein the TSO was varied accordingly: TSO is tailed with 3 Uracil bases (with a V base spacer) (TSO-rU), or 3 Adenine bases (with a B base spacer) (TSO-rA), or 3 Cytidine bases (with a G base spacer) (TSO-rC), or 3 Guanine bases (with an H base spacer) (TSO-rG), or all RNA bases (TSO-rN). Each TSO was tested in the presence of 1 mM dATP, 1 mM dTTP, 1 mM dCTP, 1 mM dGTP single nucleotide. Controls for the experiment include: one reaction with no dNTPs added (performed with TSO-rN) and one reaction for each TSO with all the dNTPs added simultaneously.

Figure 26:
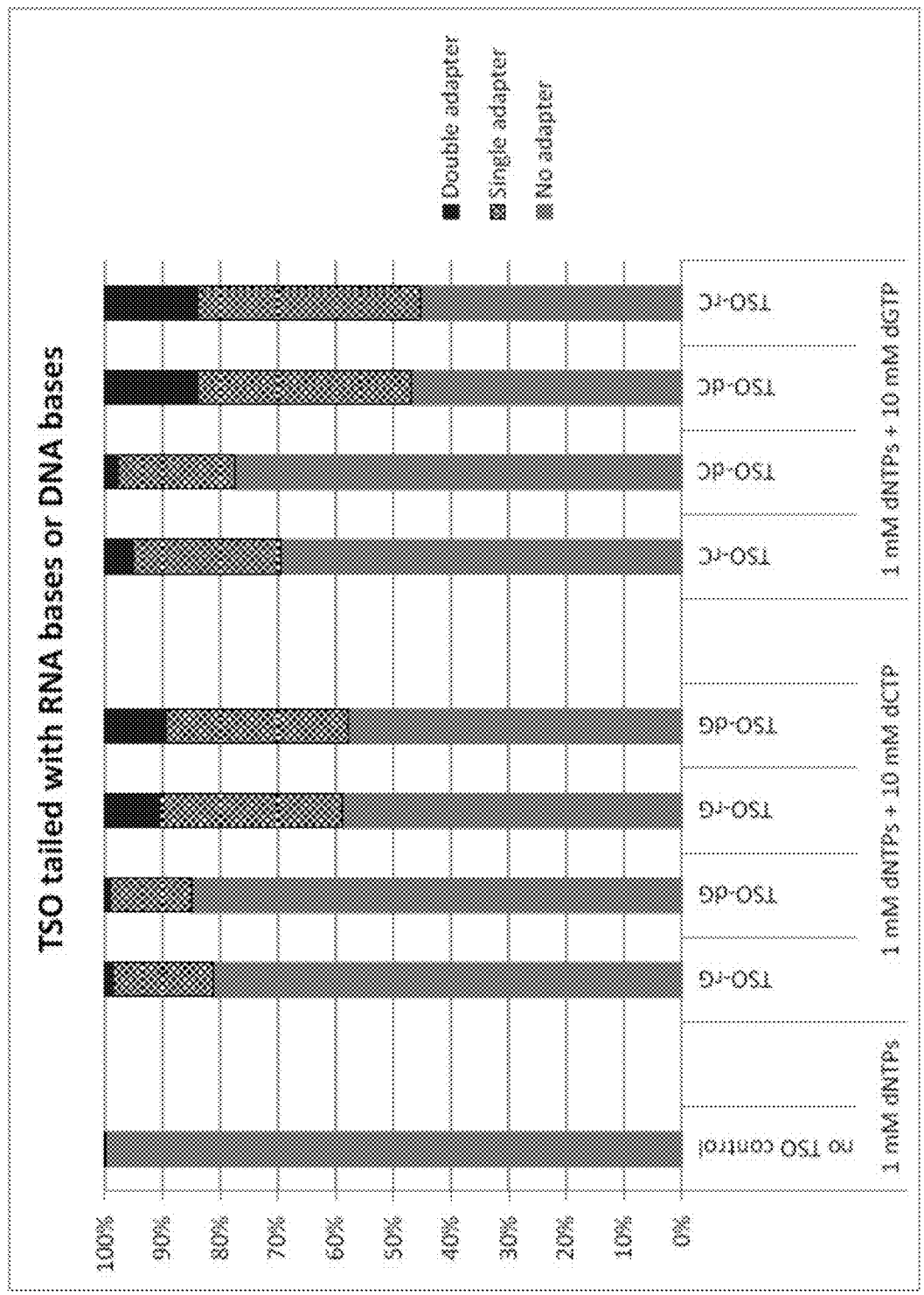

FIG. 26 is a graph showing the ratio of species to the total molarity wherein the species are: 1) the dsDNA amplicon with no adapter addition (no adapter), 2) the amplicon with an adapter added to one end (single adapter), 3) and the amplicon with an adapter added on both ends (double adapter). The y-axis reflects percent of each species in each sample. The x-axis reflects reaction conditions wherein the TSO was varied accordingly: TSO is tailed with 3 RNA Guanine bases (TSO-rG), or 3 RNA Cytosine bases (TSO-rC), or 3 DNA Guanine bases (TSO-dG), or 3 DNA Cytosine bases (TSO-dC). 1 mM of single nucleotide, and reaction buffer was added followed by an additional 10 mM of the complementary nucleotide specific TSO reactions. A no TSO control was included with only 1 mM dNTPs added.

Figure 27:
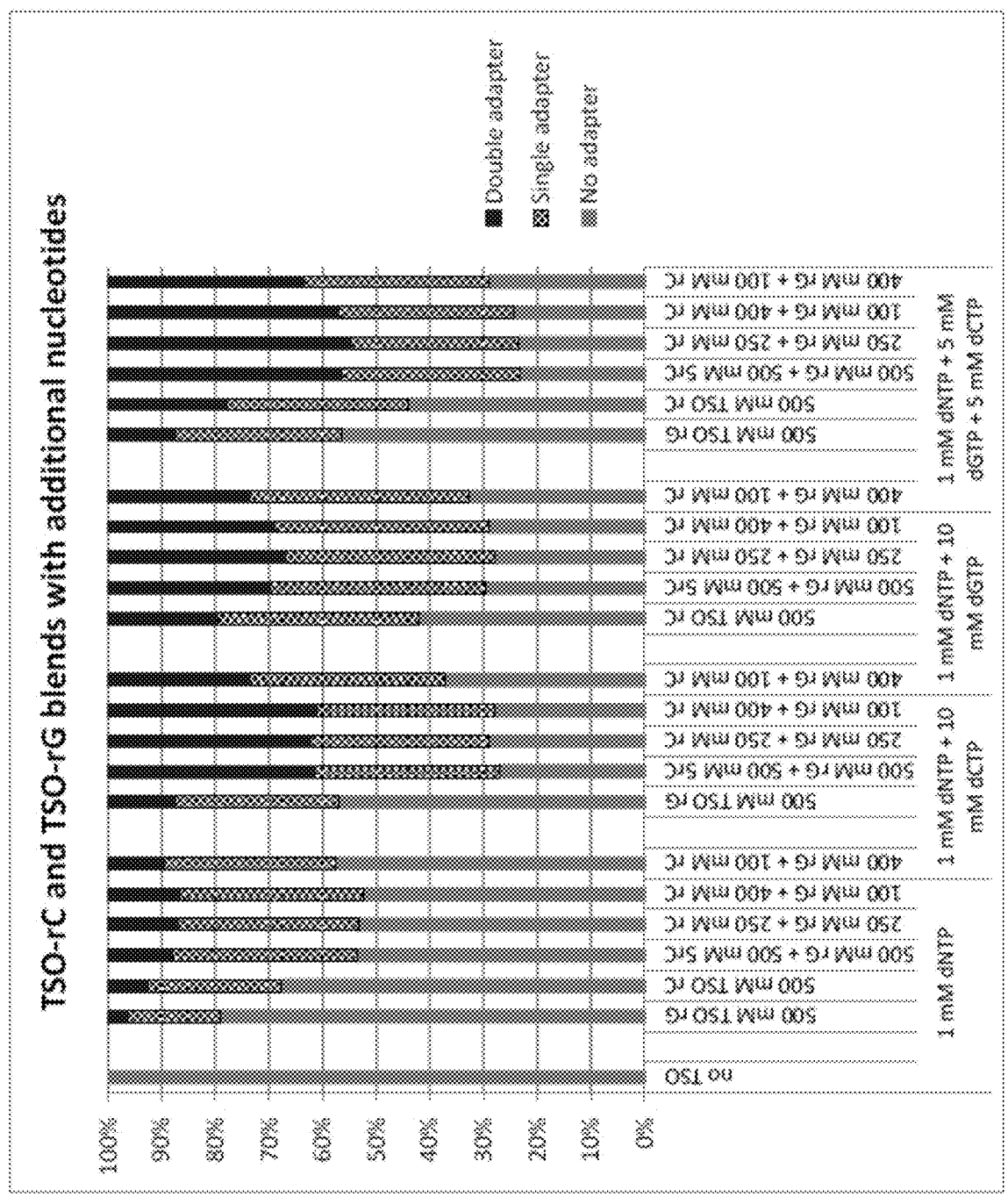

FIG. 27 is a graph showing the ratio of species to the total molarity wherein the species are: 1) the dsDNA amplicon with no adapter addition (no adapter), 2) the amplicon with an adapter added to one end (single adapter), 3) and the amplicon with an adapter added on both ends (double adapter). The y-axis reflects percent of each species in each sample. The x-axis reflects reaction conditions wherein a TSO with three Guanine bases (with an H spacer base) and a TSO with three Cytosine bases (with a D spacer base) were combined in different ratios and incubated with different amounts and combinations of nucleotides, either with no additional nucleotides, or with additional dCTP and/or with additional dGTP in the presence of 24 mM Mg2+. The dsDNA amplicon was incubated with MMLV RT and reaction buffer containing either 1 mM dNTPs, or 1 mM dNTPs+10 mM dCTP, or 1 mM dNTPs+10 mM dGTP, or 1 mM dNTPs+5 mM dCTP+5 mM dGTP. The reactions also contained: no TSO, or 500 mM TSO-rC or TSO-rG, or 500 mM TSO-rC and 500 mM TSO-rG, or 250 mM TSO-rC and 250 mM TSO-rG, or 400 mM TSO-rC and 100 mM TSO-rG, or 100 mM TSO-rC and 400 mM TSO-rG. The reactions were incubated at 42° C. for 10 min.

Figure 28:
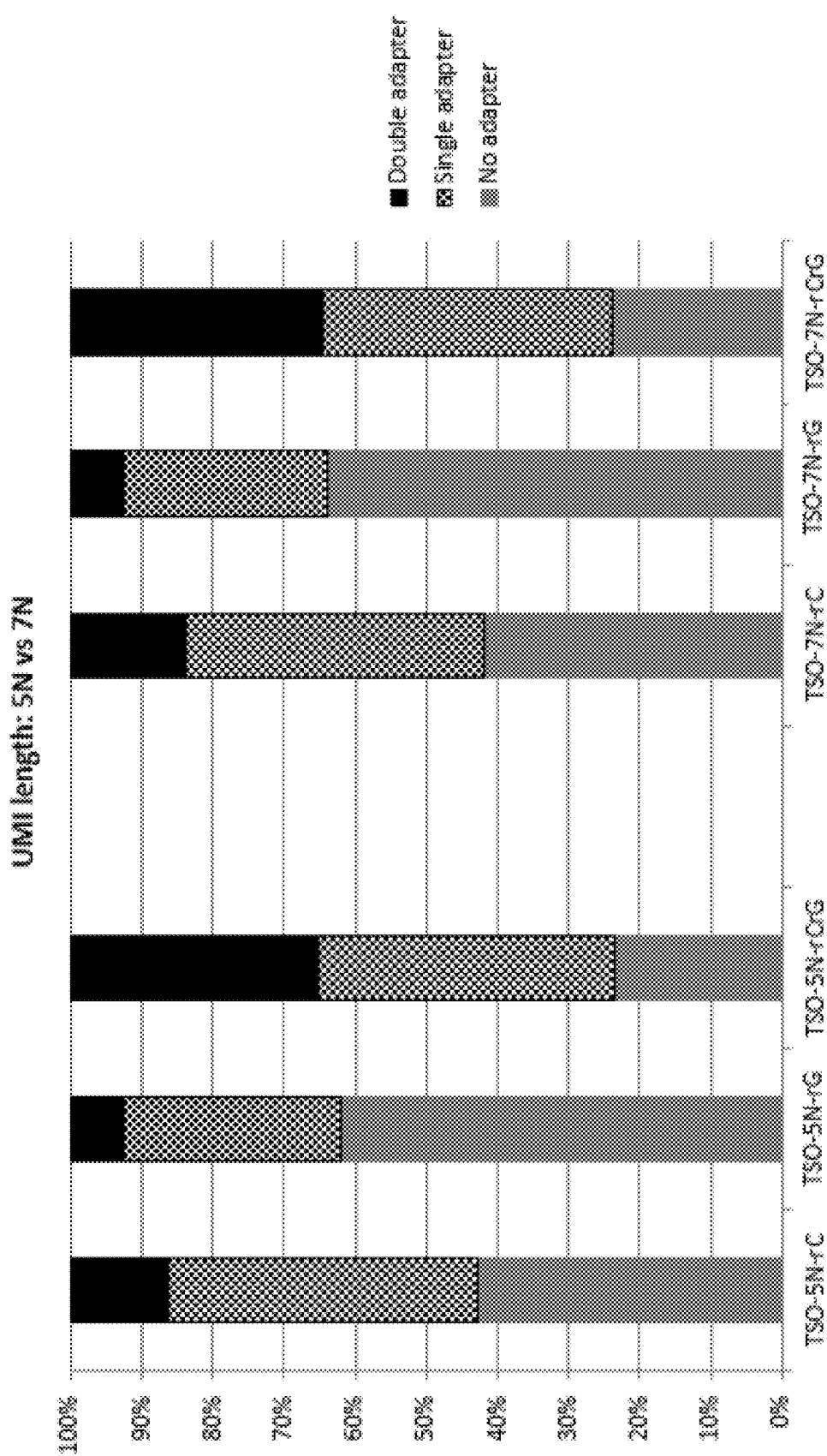

FIG. 28 is a graph showing the ratio of species to the total molarity wherein the species are: 1) the dsDNA amplicon with no adapter addition (no adapter), 2) the amplicon with an adapter added to one end (single adapter), 3) and the amplicon with an adapter added on both ends (double adapter). The y-axis reflects percent of each species in each sample. The x-axis reflects reaction conditions wherein a TSO-rC, TSO-rG, or TSO-rC+TSO-rG either having a 5N UMI or a 7N UMI were incubated with dNTPS.

Figure 29:
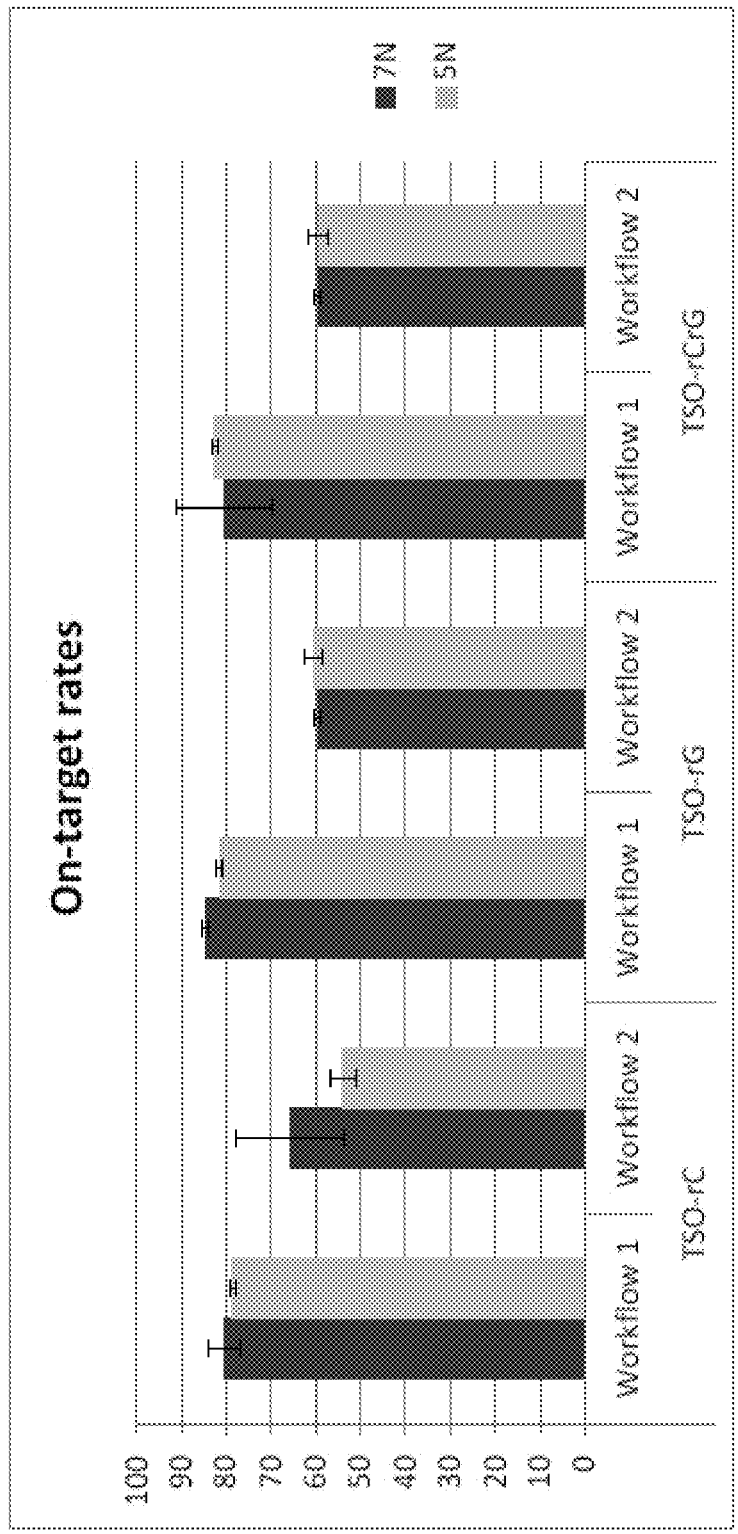

FIG. 29 is a graph showing the on-target rates of 5N or 7N UMI-containing TSOs wherein the TSOs are TSO-rC, TSO-rG or TSO-rCrG using workflow 1 or workflow 2.

Figure 30:
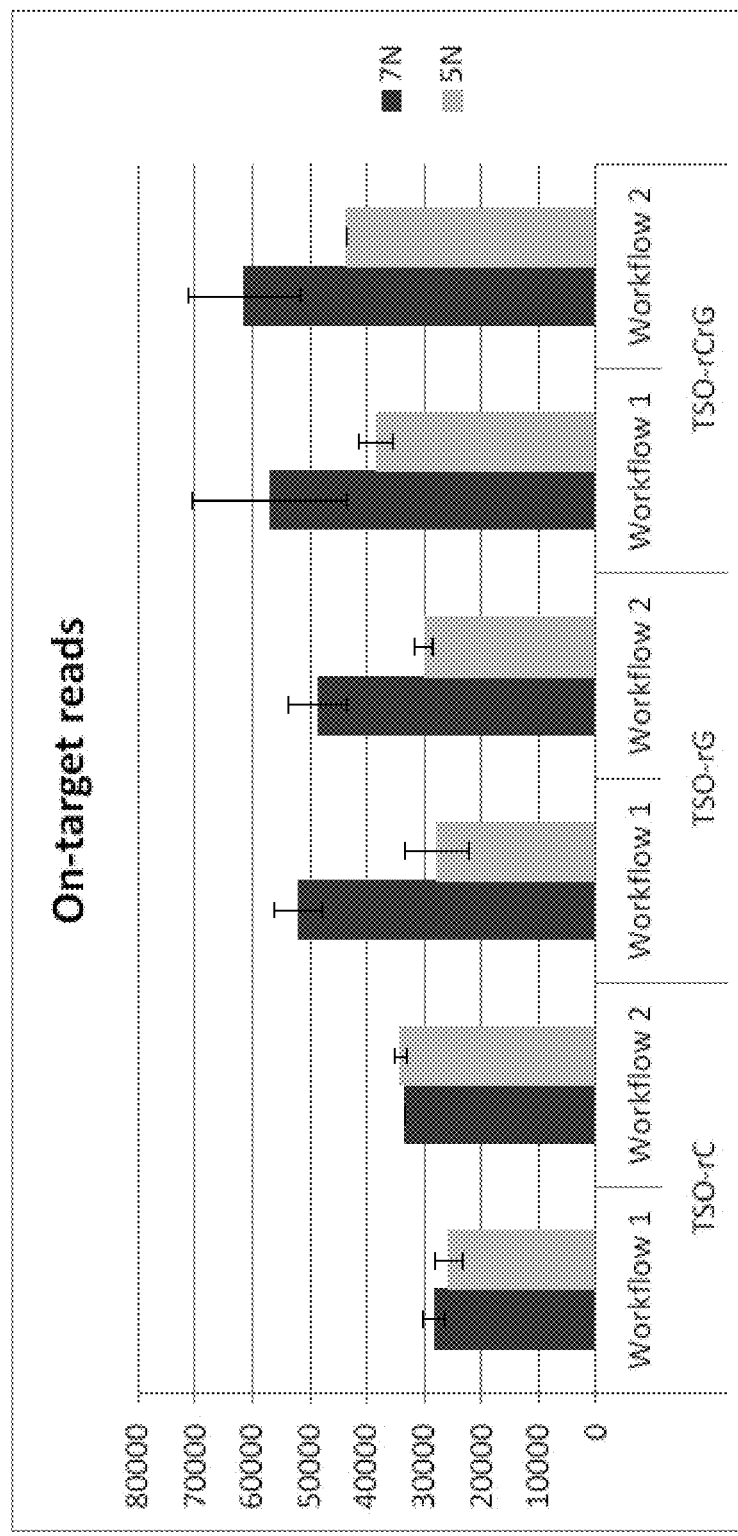

FIG. 30 is a graph showing the on-target reads of 5N or 7N UMI-containing TSOs wherein the TSOs are TSO-rC, TSO-rG or TSO-rCrG using workflow 1 or workflow 2. The y-axis displays the number of reads.

Figure 31:
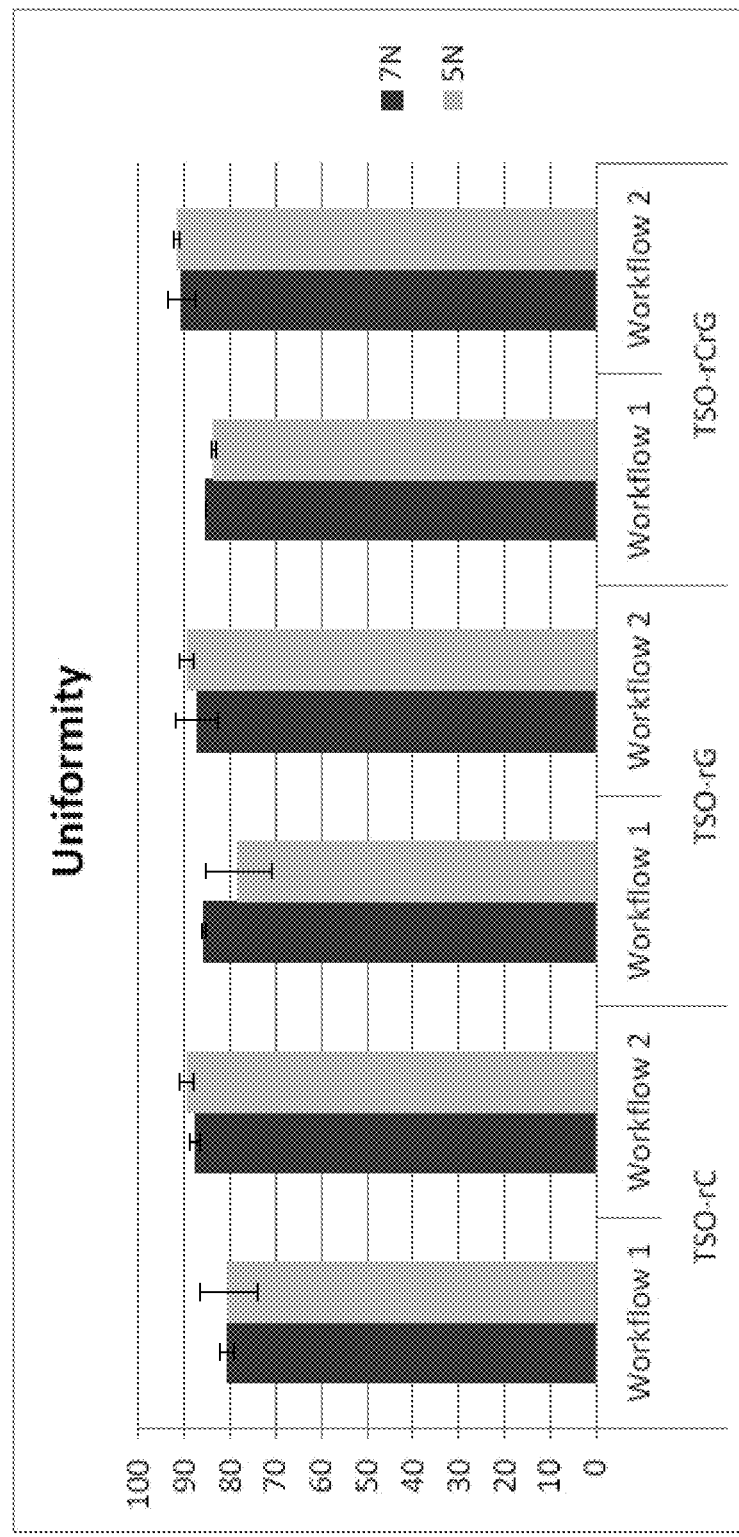

FIG. 31 is a graph showing the uniformity of 5N or 7N UMI-containing TSOs wherein the TSOs are TSO-rC, TSO-rG or TSO-rCrG using workflow 1 or workflow 2.

Figure 32:
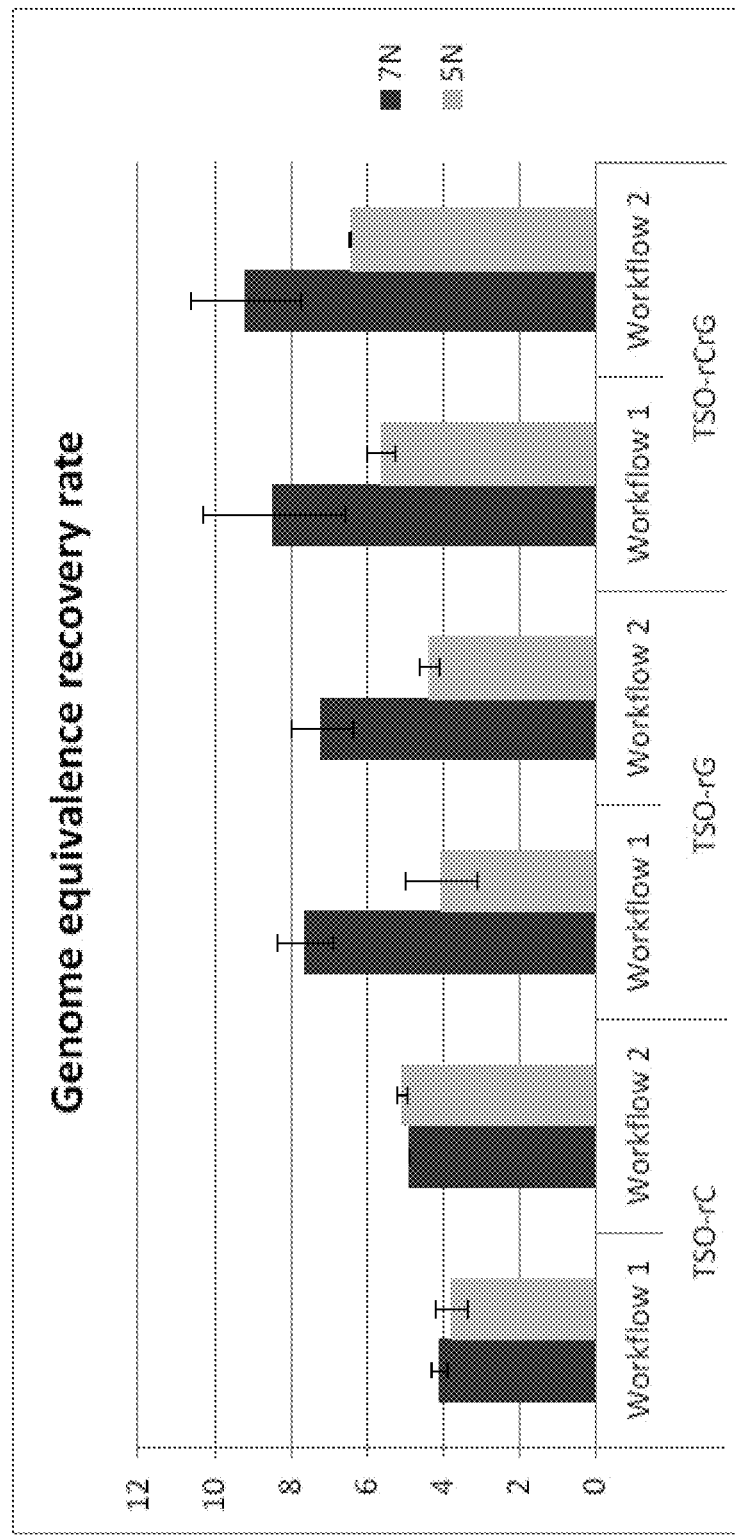

FIG. 32 is a graph showing the genome equivalence recovery rate of 5N or 7N UMI-containing TSOs wherein the TSOs are TSO-rC, TSO-rG or TSO-rCrG using workflow 1 or workflow 2.

DETAILED DESCRIPTION

Conventional amplicon sequencing technologies suffer from the inability to detect novel gene fusions due to the requirement for the existence of closely located known forward and reverse gene specific primer binding sites. Additionally, these methods are generally unable to distinguish between PCR duplicates and unique molecules. Technologies such as ArcherDx avoid this difficulty by using ligation to attach an adaptor to genomic DNA or cDNA and then perform PCR with one or two (nested) gene specific primers and an adaptor-specific primer. There are disadvantages to ligation based technologies which include workflow, time (often, overnight ligation is required for low input samples), sensitivity to input (ligation reactions are not very efficient at sub-nanogram levels) and propensity for artefact formation, such as the formation of adaptor dimers.

The extant disclosure provides for the efficient attachment of an adaptor to a small amount (less than 10 nanograms) of sheared genomic DNA or cDNA, or PCR product, followed by multiplex PCR using target-specific primers in combination with an adaptor specific primer. One way to achieve this is by using the terminal transferase activity and template switching (TS) ability of Moloney Murine Leukemia Virus reverse transcriptase (MMLV RT). The mechanism involves the ability of the MMLV RT to add non-templated bases to the 3' end of a cDNA strand, once the template (which is normally RNA) end is reached (terminal transferase activity), followed by the annealing of a complementary 3' oligo (template-switching oligo, TSO). The MMLV RT subsequently switches the template which is being reverse transcribed, from the original template to the TSO. The end result is the attachment of a 3' adaptor sequence to the reverse transcribed strand and forms the basis of the SMART technology originally invented to amplify full-length cDNA and which forms the basis of many single cell RNA-seq workflows.

The template switching mechanism works on DNA as well. The RT will copy single stranded DNA and is able to use the TSO to add a 3' adaptor to the growing strand, much like with RNA templates. However, this process is problematic as MMLV RT is error prone and the resulting copied strand will contain mismatches which may present as false positive single nucleotide variant calls during subsequent sequence analysis.

Therefore, the methods of the disclosure use the template switching activity of MMLV RT (and other enzymes capable of performing these activities) to add 3' adaptor sequences to DNA.

There are a number of advantages to this approach. First, the reaction is extremely efficient. In RNA applications, picogram quantities of template are routinely used. The TSO-based method has the potential of working with much smaller quantities of input than ligation-based methods. Second, the workflow for the reaction is simple. Attachment of adaptors via TS of MMLV RT is a single-tube reaction, which has the potential of being much shorter than ligation. Following adaptor addition by TS, the product can be directly used in PCR. At a minimum, building a library involves only an oligo (TSO), the RT enzyme and buffer. Third, no extra adaptors are required. The adaptor sequence is added via the TSO. Fourth the method captures both strands of a template molecule, as in a dsDNA template, 3' adaptor is added to both strands. Fifth, the method can be easily adapted to add unique identifiers and/or sample identifiers (barcodes) to the DNA molecules during the template-switching step. Lastly, the template switching step can be performed with methylated deoxycytidine, resulting in the addition of adaptors which are resistant to bisulfite treatment, enabling the use of this method for bisulfite sequencing.

Aside from using the TS to simply add adaptors, the method can be adapted to uncoupling the extension and template-switching (adaptor addition) reactions, allowing it to work with a versatile range of starting materials. The starting template DNA can be double stranded DNA prepared by a variety of methods, or single stranded DNA.

The disclosure thus provides for compositions and methods of using a fast and simple template switching mechanism to add terminal sequences to a template DNA or library of template DNAs in preparation for sequencing applications. The compositions and methods of the disclosure provide solutions for significant problems in the field, namely provide methods for sequencing across novel fusion events, improving the workflow of cumbersome ligation-based processes and reducing the amount of starting material needed.

Definitions

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

Nucleotide: As used herein, a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus.

Universal bases: As used herein, the term "universal base" refers to a nucleic acid analog that is able to base pair indiscriminately with each of the four standard nucleotide bases. Non limiting examples of universal bases include inosines, indoles, hypoxanthine, nitroazoles, isocarbostyril analogues, azole carboxamides and aromatic triazole analogues. Exemplary universal bases include, but are not limited to 2'-deoxyinosine (dI), nitroindole, 2'-deoxyNebularine, 3-nitropyrrole and 5-nitroindole.

Oligonucleotide or Polynucleotide: As used herein, the term "oligonucleotide" or "oligo" is defined as a molecule including two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning. As used herein, the term "polynucleotide" refers to a polymer molecule composed of nucleotide monomers covalently bonded in a chain. DNA (deoxyribonucleic acid) and RNA (ribonucleic acid) are examples of polynucleotides.

Polymerase: As used herein, a "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. A "DNA polymerase" catalyzes the polymerization of deoxynucleotides.

Reverse transcriptase: As used herein, a "reverse transcriptase (RT) refers to an enzyme that is capable of catalyzing the polymerization of a complementary DNA polynucleotide from an RNA polynucleotide template. Reverse transcriptase enzymes are typically isolated or derived from retroviruses. Retroviral RTs typically comprise several biochemical activities, including but not limited to RNA-dependent DNA polymerase activity, ribonuclease activity, and DNA-dependent DNA polymerase activity. Exemplary RTs include the Moloney Murine Leukemia Virus RT (MMLV RT) and the Avian Myeloblastosis Virus RT (AMV RT).

Terminal transferase: As used herein, the term "terminal transferase" refers to an enzyme capable of adding nucleotides to the 3' end(s) of a DNA molecule in template independent manner. "Terminal transferase activity" refers to the terminal transferase activity of any an enzyme with that capability.

Exonuclease: As used herein, the term "exonuclease" refers to an enzyme that works by cleaving nucleotides from the ends of a polynucleotide. Exonucleases can work 5' to 3', or 3' to 5', and can target single stranded DNA or double stranded DNA, depending on the enzyme.

Primer: As used herein, the term "primer" refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is a deoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

Template DNA molecule: As used herein, the term "template DNA molecule" refers to a strand of a nucleic acid from which a complementary nucleic acid strand is synthesized by a DNA polymerase, for example, in a primer extension reaction.

Template switching: as used herein, the term "template switching" refers to an activity of a polymerase that is capable of switching template strands in a homology dependent manner during DNA synthesis. An example of a polymerase with template switching activity is MMLV RT.

Random sequence: As used herein, the phrase "random sequence" refers to, in some embodiments, a mixture of nucleotides, which are synthesized in a way that allows the incorporation of any one of the four bases (i.e., A, T, G, and C) at specific oligonucleotide positions during the synthesis. For example, ACGCGACGNNNNNNTGGGACGA (SEQ ID NO: 13) contains a random sequence, where 'N' represents a random nucleotide. Oligonucleotide synthesis with the exemplified sequence could produce $4^6$ distinct oligonucleotides due to the presence of the 6 consecutive random nucleotides and the use of 4 different bases (i.e., A, T, G, and C). In some embodiments, the phrase "random sequence" refers to a mixture of amino acids, which are synthesized in a way that allows the incorporation of any one of the 26 amino acids at specific amino acid positions during the synthesis. For example, "XXXXXX" (SEQ ID NO: 14) contains a random sequence, where 'X' represents a random amino acid. Peptide synthesis with the exemplified sequence could produce $26^6$ peptides due to the presence of the 6 consecutive random amino acids and the use of 26 different amino acids.

Sample identifier: As used herein, the phrase "sample identifier (SID)" refers to a short nucleic acid sequence, typically contained within a primer, oligonucleotide or adaptor sequence, that is added to the ends of DNA fragment being prepared for sequencing applications. SID sequences may be predetermined, or may comprise random sequences. A typical use of SIDs is as indexing sequences during sequencing of a library. Random, different SIDs are added to the ends of DNA fragments in a library, the SID is read through as part of a high throughput sequencing reaction, and the SID sequence is used to match reads back to an individual DNA fragment or sample.

Unique identifier: As used herein, the phrase "unique identifier (UID)" refers to a short nucleic acid sequence, typically contained within a primer, oligonucleotide or adaptor sequence, that is added to the ends of DNA fragment being prepared for sequencing applications. UID sequences may be predetermined, or may comprise random sequences. A typical use of UIDs is as indexing sequences during sequencing of a library. Random, different UIDs are added to the ends of DNA fragments in a library, the UID is read through as part of a high throughput sequencing reaction, and the UID sequence is used to match reads back to an individual DNA fragment or sample. Depending on the application, DNA fragments, or libraries of DNA fragments, may require 1 or 2 rounds of indexing. The SID and the UID may therefore be the same, or comprise different sequences.

Template DNA

The disclosure provides efficient methods for adding terminal sequences to a template DNA or template DNA library, and amplifying that DNA if called for. In some embodiments, the starting template DNA is blunt ended. There are a number of ways to generate blunt ended DNA template. For example, the template DNA may be a PCR product. Many DNA polymerases, particularly high fidelity polymerases contain an intrinsic 3' to 5' exonuclease activity as part of their proofreading function that results in a blunt ended PCR product. Other polymerases, such as the canonical Taq polymerase, add 3' adenosine overhangs to PCR amplification products resulting in sticky (not blunt) PCR products. PCR products with overhangs incompatible to the methods of the disclosure can be blunted enzymatically to produce blunt ended template DNA, using enzymes such as DNA polymerase large fragment I (Klenow), T4 DNA polymerase, or Mung Bean nuclease.

In some embodiments, the template DNA is sheared DNA. Shearing the DNA takes large size DNA molecules and reduces them to fragments of a small enough size that their sequences can be captured by the read lengths of current sequencing technologies. DNA can be sheared a mechanically or enzymatically. Mechanical methods of shearing DNA include sonication, passing the DNA in solution through a fine gage needle, nebulization, point-sink shearing and passage through a French pressure cell. Focused acoustic shearing devices and high power sonication devices, of which the Covaris Focused Ultrasonicator is one example, are able to efficiently fragment DNA down to 100 bp.

An alternative to mechanical methods of shearing DNA is enzymatic shearing. Enzymatic shearing fragments DNA either by simultaneous cleavage of both strands, or by the generation of nicks on each strand of the dsDNA to produce dsDNA breaks. For example, DNA could be treated with a restriction enzyme that cuts at every instance of a particular restriction enzyme recognition sequence. Alternatively, DNA could be treated with a combination of two enzymes, one of which nicks the DNA at random, and the other of which recognizes the nicked sites and cuts the dsDNA on the strand across from the nick, generating a double strand break. If the particular method of shearing, mechanical or enzymatic, generates sticky ends, the resulting DNA fragments can be treated, or "repaired" enzymatically to be blunt ended by enzymes such as DNA polymerase large fragment I (Klenow), T4 DNA polymerase or Mung Bean nuclease.

Any number of DNA sources are potential starting material for the methods and compositions of the disclosure. For example, the DNA to undergo the template switching reaction could be from an extrachromosomal cloning vector such as a plasmid, a viral vector, a lambda phage vector or some other cloning product, such as a bacterial or yeast artificial chromosome (BAC or YAC), a phosmid, or a cosmid. Larger, more complex DNA templates are also suitable starting materials for the methods of the disclosure. For example, the methods of the disclosure can be used to generate sequencing libraries for genomic DNA, mitochondrial DNA or chloroplast DNA. Another potential application is in the sequencing of cell free DNA, such as fetal DNA circulating in the maternal blood stream.

The choice of DNA shearing method depends on the type of DNA starting material, the desired fragment size, and the desired end application. For example, if the DNA to be fragmented and treated with the methods of the disclosure is fairly small and previously characterized, such as a vector or a plasmid, fragmenting it through restriction digest may produce an adequate size range of fragments. In contrast, if the starting material is genomic DNA, random enzymatic or mechanical methods may produce a more uniform range of fragment sizes, and reduce bias in the representation of the genomic DNA in the final sequencing library.

Methods of the disclosure include starting with a single stranded DNA template, for example a DNA that has been sheared and then denatured. When starting with a single stranded DNA template, the first step of the methods comprises priming a single round of polymerase extension with a template specific primer before undergoing the template switching reaction.

One advantage of the methods of the disclosure is that the methods work with very small amounts of starting material. In some embodiments of the methods of the disclosure, the concentration of starting template DNA in is between 0.1 ng and 100 ng, inclusive of the endpoints. In some embodiments, the concentration of the template DNA in is equal to or less than 0.1 ng, 1 ng, 10 ng or 100 ng. Standard protocols in the field for making genomic DNA sequencing libraries still routinely call for 100 ng to a 1 μg or more of starting DNA. The methods of the disclosure call for between 1-4 orders of magnitude less starting DNA.

Addition of the 3' Adaptor Sequences

The methods of the disclosure comprise the addition of an adaptor sequence to the ends of the blunt ended template DNA fragment(s). This is typically accomplished through an enzyme with terminal transferase activity, which adds several non-templated nucleotides to the 3' hydroxyl terminus of each strand of the blunt ended dsDNA template.

The methods of the disclosure comprise the use of one or more enzymes with terminal transferase activity.

An exemplary enzyme of the disclosure having terminal transferase activity is the Moloney Murine Leukemia Virus reverse transcriptase, or MMLV RT, a reverse transcriptase isolated or derived from the Moloney Murine Leukemia Virus.

An exemplary wild type MMLV RT protein sequence comprises the amino acid sequence:

An exemplary enzyme of the disclosure having terminal transferase activity is the HIV-1 reverse transcriptase, which is capable of adding non-templated deoxynucleotides to the 3' end of DNA molecule.

An exemplary enzyme of the disclosure having terminal transferase activity is the human DNA nucleotidyltransferase (TdT), which is capable of adding non-templated deoxynucleotides to the 3' end of DNA molecule.

MMLV RT typically adds between 1 and 5 non-templated nucleotides to the 3' end of a dsDNA molecule. MMLV RT preferentially adds cytosines, resulting in the poly(C) adap-

```
                                                                    (SEQ ID NO: 9)
  1 AFPLERPDWD YTTQAGRNHL VHYRQLLLAG LQNAGRSPTN LAKVKGITQG PNESPSAFLE

61 RLKEAYRRYT PYDPEDPGQE TNVSMSFIWQ SAPDIGRKLG RLEDLKSKTL GDLVREAEKI

121 FNKRETPEER EERIRRETEE KEERRRTVDE QKEKERDRRR HREMSKLLAT VVIGQEQDRQ

181 EGERKRPQLD KDQCAYCKEK GHWAKDCPKK PRGPRGPRPQ TSLLTLGDXG GQGQDPPPEP

241 RITLKVGGQP VTFLVDTGAQ HSVLTQNPGP LSDKSAWVQG ATGGKRYRWT TDRKVHLATG

301 KVTHSFLHVP DCPYPLLGRD LLTKLKAQIH FEGSGAQVVG PMGQPLQVLT LNIEDEYRLH

361 ETSKEPDVSL GFTWLSDFPQ AWAESGGMGL AVRQAPLIIP LKATSTPVSI KQYPMSQEAR

421 LGIKPHIQRL LDQGILVPCQ SPWNTPLLPV KKPGTNDYRP VQDLREVNKR VEDIHPTVPN

481 PYNLLSGLPP SHQWYTVLDL KDAFFCLRLH PTSQPLFAFE WRDPEMGISG QLTWTRLPQG

541 FKNSPTLFDE ALHRDLADFR.
```

An exemplary enzyme of the disclosure having terminal transferase activity is the Avian Myeloblastosis Virus reverse transcriptase (AMV RT), a reverse transcriptase isolated or derived from the Avian Myeloblastosis Virus.

An exemplary wild type AMV RT protein sequence comprises the amino acid sequence:

tor sequence of the disclosure. Under the conditions provided in the examples of the disclosure, MMLV RT adds 3 cytosines to the 3' ends of the DNA. However, as other terminal transferases have different nucleotide preferences, and nucleotide incorporation can be controlled, for example, by the availability of dNTPs in the reaction mixture, the

```
                                                                    (SEQ ID NO: 10)
  1 IGRATVLTVA LHLAIPLKWK PNHTPVWIDQ WPLPEGKLVA LTQLVEKELQ LGHIEPSLSC

61 WNTPVFVIRK ASGSYRLLHD LRAVNAKLVP FGAVQQGAPV LSALPRGWPL MVLDLKDCFF

121 SIPLAEQDRE AFAFTLPSVN NQAPARRFQW KVLPQGMTCS PTICQLIVGQ ILEPLRLKHP

181 SLRMLHYMDD LLLAASSHDG LEAAGEEVIS TLERAGFTIS PDKVQREPGV QYLGYKLGST

241 YVAPVGLVAE PRIATLWDVQ KLVGSLQWLR PALGIPPRLR GPFYEQLRGS DPNEAREWNL

301 DMKMAWREIV RLSTTAALER WDPALPLEGA VARCEQGAIG VLGQGLSTHP RPCLWLFSTQ

361 PTKAFTAWLE VLTLLITKLR ASAVRTFGKE VDILLLPACF RDDLPLPEGI LLALRGFAGK

421 IRSSDTPSIF DIARPLHVSL KVRVTDHPVP GPTVFTDASS STHKGVVVWR EGPRWEIKEI

481 ADLGASVQQL EARAVAMALL LWPTTPTNVV TDSAFVAKML LKMGQEGVPS TAAAFILEDA

541 LSQRSAMAAV LHVRSHSEVP GFFTEGNDVA DSQATFQAYP LREAKDLHTA LHIGPRALSK

601 ACNISMQQAR EVVQTCPHCN SAPALEAGVN PRGLGPLQIW QTDFTLEPRM APRSWLAVTV

661 DTASSAIVVT QHGRVTSVAA QHHWATAIAV LGRPKAIKTD NGSCFTSKST REWLARWGIA

721 HTTGIPGNSQ GQAMVERANR LLKDKIRVLA EGDGFMKRIP TSKQGELLAK AMYALNHFER

781 GENTKTPIQK HWRPTVLTEG PPVKIRIETG EWEKGWNVLV WGRGYAAVKN RDTDKVIWVP

841 SRKVKPDIAQ KDEVTKKDEA SPLFAGWRHI DKRIITLHSS FSKINLLVCF IFH.
``` sequence of the adaptor is not limited to a poly(C) sequence. Poly(G), poly(A), poly(T) and random mixed sequence adaptors are also possible, and may even be preferred in some embodiments of the methods of the disclosure. For example, in some embodiments, poly(A) adaptors could make use of existing reagents developed to work with poly(A) tailed cDNAs.

The Template Switching Oligo (TSO)

In some embodiments, the adaptor added to the ends of the template DNA comprises a hybridization site for a Template Switching Oligo (TSO). In some embodiments, the hybridization site for a TSO comprises a poly(C) sequence. Exemplary TSO sequences of the disclosure may hybridize to adaptors of the disclosure through complementary base pairing at this hybridization site, and, optionally, TSO sequences of the disclosure may hybridize to additional sequences within the adaptors of the disclosure.

In some embodiments, the TSO is a single stranded nucleic acid sequence. In some embodiments, the TSO is a single stranded DNA (ssDNA) molecule. In some embodiments, the TSO is a single stranded RNA (ssRNA) molecule. In some embodiments, the TSO is a single stranded DNA:RNA hybrid molecule.

An exemplary TSO of the disclosure comprises the sequence: 5' TCGTCGGCAGCGTCA-GATGTGTATAAGAGACAGNNNNNNNNrGrGrG 3' (SEQ ID NO: 11). For example, SEQ ID NO: 11, contains DNA bases from positions 1-41, however, the bases at positions 42-44 are RNA ("rGrGrG"). In this embodiment, these poly(G) RNA bases hybridize to the poly(C) sequence added by the terminal transferase to the 3' ends of the double stranded template DNA.

In some embodiments, the base pairing between the TSO and the hybridization site may be imperfect. For example, while in some cases the TSO may comprises a hybridization site having only 50% complementarity to the hybridization site of the adaptor, in other cases the complementarity may be as high as 100% complementarity. In some embodiments, the TSO, the adaptor, or both, may incorporate universal bases. Universal bases are nucleic acid analogues such as inosines or nitroindole that can pair indiscriminately with the A, T, G or C nucleotides of the adaptor or the TSO.

Within exemplary TSO of the disclosure, ssDNA sequences may comprise at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the TSO. Within exemplary TSO of the disclosure, ssDNA sequences may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO. Within exemplary TSO of the disclosure, ssDNA sequences may be continuous or discontinuous.

Exemplary TSO of the disclosure may comprise a secondary structure. In some embodiments, the secondary structure may comprise a hairpin. In some embodiments, the secondary structure may comprise a stem-loop. In some embodiments, the secondary structure may be an RNA structure that facilitates template switching by the reverse transcriptase.

Exemplary TSO of the disclosure may comprise one or more indexing sequences. In the exemplary TSO shown in SEQ ID NO: 11, the " " sequence is a place holder for an indexing sequence, such as a sample identifier (SID) or unique identifier (UID), that can be used to index the template DNA fragments so that individual reads can traced back to individual fragments, or samples, or a combination of the two, in a pooled DNA sequencing library. UID and SID sequences of the disclosure range in length from 1 to 20 nucleotides, inclusive of the endpoints. The length of the indexing sequence depends on the complexity of the DNA template library, the number of fragments to be sequenced, and the sequencing applications. For example, it may be desirable to uniquely label each template DNA fragment with a random UID and/or SID. In this example, the larger and more complex the library, then the longer the UID and/or SID sequences need to be to uniquely label each fragment. Conversely, smaller libraries, such as those sequencing a plasmid, vector, or small genome such as a viral genome, need smaller UIDs and/or SIDs. Depending on the needs of a particular embodiment, the UID and SID sequences may be the same, or different sequences. UID sequences and/or SID sequences, may comprise a predetermined sequence designed to meet the needs of a particular embodiment of the disclosure. One of the strengths of the disclosure is the flexibility in designing the sequence of each TSO for a particular embodiment or application of the compositions and methods of the disclosure.

In some embodiments, a TSO of the disclosure may comprise, for example, in a 5' portion of the TSO, one or more sequences that can hybridize to a primer in either a PCR reaction to amplify the DNA template sequence or in a sequencing reaction. In some embodiments, in a 5' portion of the TSO, the one or more sequences that can hybridize to a primer comprise a ssDNA. In some embodiments, the ssDNA of the TSO comprises or consists of a sequence having at least 50% identity or complementarity to a sequence of a primer, an adaptor, or a component of an array. In some embodiments, the ssDNA of the TSO comprises or consists of a sequence having at least 50%, at least 55%, at least 60%, at least 65%, at least 70%, at least 75%, at least 80%, at least 85%, at least 90%, at least 95%, at least 97%, at least 99%, at least 100% or any percentage in between of identity or complementarity to a sequence of a primer, an adaptor, or a component of an array.

In some embodiments, a TSO of the disclosure may comprise a methylated deoxycitidine (5-methylcytosine). Methylated deoxycitidines are refractory to bisulfate treatment, which converts unmethylated deoxycitidines to uracil. Bisulphite sequencing may be used to determine the methylation status of DNA. In some embodiments of the methods of the disclosure, a template DNA or a DNA library may be prepared for or subject to bisulphite sequencing to determine methylation status.

Template Switching and Extension

In some embodiments of the methods of the disclosure, once a complementary portion of the TSO hybridizes to a sequence of an adaptor, a polymerase, a reverse transcriptase (RT), or a MMLV RT for example, switches strands of the DNA template and extends the strand complementary to the TSO in a 5' to 3' direction, thereby catalyzing DNA dependent DNA polymerization. In some embodiments, the template switching step produces a double stranded DNA (dsDNA) molecule, in which the original template sequence is flanked on either side by an adaptor sequence that has been added through the template switching mechanism. Reading from the sense strand, from 5' to 3', the dsDNA product of the template switching step comprises or consists of a first adaptor sequence, a template DNA sequence, and a second adaptor sequence. In some embodiments, the first adaptor sequence comprises a sequence identical to a sequence of the TSO. In some embodiments, the second adaptor sequence comprises a sequence identical to a sequence complementary to a sequence of the TSO. In some embodiments, the 3' and 5' adaptor sequences may comprise identical sequences. In other embodiments, the 3' and 5' adaptor sequences may not comprise identical sequences. For example, the 3' and 5' adaptor sequences may comprise a different SID sequence and/or a different UID sequence. In some embodiments, only one side of the template DNA, either the 3' or the 5' end of the template DNA, has an adaptor that has been added by the template switching methods of the disclosure. In some embodiments, the dsDNA product of the template switching step, this "dsDNA intermediate", can then be used as a template or starting material for in a variety of amplification reactions and/or sequencing reactions.

In some embodiments of the methods of the disclosure, comprise a strand extension step. In some embodiments, the strand extension step is performed after the template switching step. In some embodiments, the strand extension step comprises an incorporation of a methylated deoxycitidine (5-methylcytosine). Methylated deoxycitidines are refractory to bisulfate treatment, which converts unmethylated deoxycitidines to uracil. Bisulphite sequencing may be used to determine the methylation status of the DNA. In some embodiments of the methods of the disclosure, a template DNA or a DNA library may be prepared through a strand extension step after a template switching step. In some embodiments of the methods of the disclosure, a template DNA or a DNA library prepared through a strand extension step performed after a template switching step may be prepared for bisulphite sequencing to determine methylation status.

Amplification from Double Stranded DNA (dsDNA)

A double stranded DNA (dsDNA) of the disclosure may include, but is not limited to, a template DNA, a dsDNA of a DNA library, or a dsDNA flanked by one or more adaptor sequences of the disclosure (e.g. adaptor sequences that may have been added through a template switching step of the disclosure). dsDNAs of the disclosure may be used as substrates (including initial substrates) for a variety of additional applications, including, but not limited to amplification and sequencing reactions. dsDNAs of the disclosure may contact one or more primers. In some embodiments, dsDNAs of the disclosure contact a first primer having a sequence complementary to a sequence of a template sequence of the dsDNA and a second primer having a sequence complementary to a sequence of either an adaptor sequence of the disclosure or a TSO sequence of the disclosure.

In some embodiments, dsDNAs of the disclosure contact one or more primers and a DNA polymerase. Exemplary DNA polymerases of the disclosure include, but are not limited to, DNA polymerases isolated or derived from archaea. In some embodiments, the polymerase has been engineered for improved fidelity, processivity, elongation rate, thermostability, tetra-methyl ammonium chloride (TMAC) tolerance, salt resistance, or a combination thereof. In some embodiments, the polymerase comprises a sequence that is at least 80%, at least 85%, at least 90%, at least 91%, at least 92%, at least 93%, at least 94%, at least 95%, at least 96%, at least 97%, at least 98%, or at least 99% identical to the nucleotide sequence of any one of SEQ ID NOs 1, 3, 5, and 7 or the amino acid sequence of any one of SEQ ID NOs 2, 4, 6, and 8. In some embodiments, the polymerase comprises a sequence that is at least 80%, at least 85%, at least 90%, at least 91%, at least 92%, at least 93%, at least 94%, at least 95%, at least 96%, at least 97%, at least 98%, or at least 99% identical to the nucleotide sequence of SEQ ID NO: 1 or the amino acid sequence of SEQ ID NO: 2. In some embodiments, the polymerase comprises a sequence that is at least 80%, at least 85%, at least 90%, at least 91%, at least 92%, at least 93%, at least 94%, at least 95%, at least 96%, at least 97%, at least 98%, or at least 99% identical to the nucleotide sequence of SEQ ID NO: 3 or the amino acid sequence of SEQ ID NO: 4.

Figure 5:
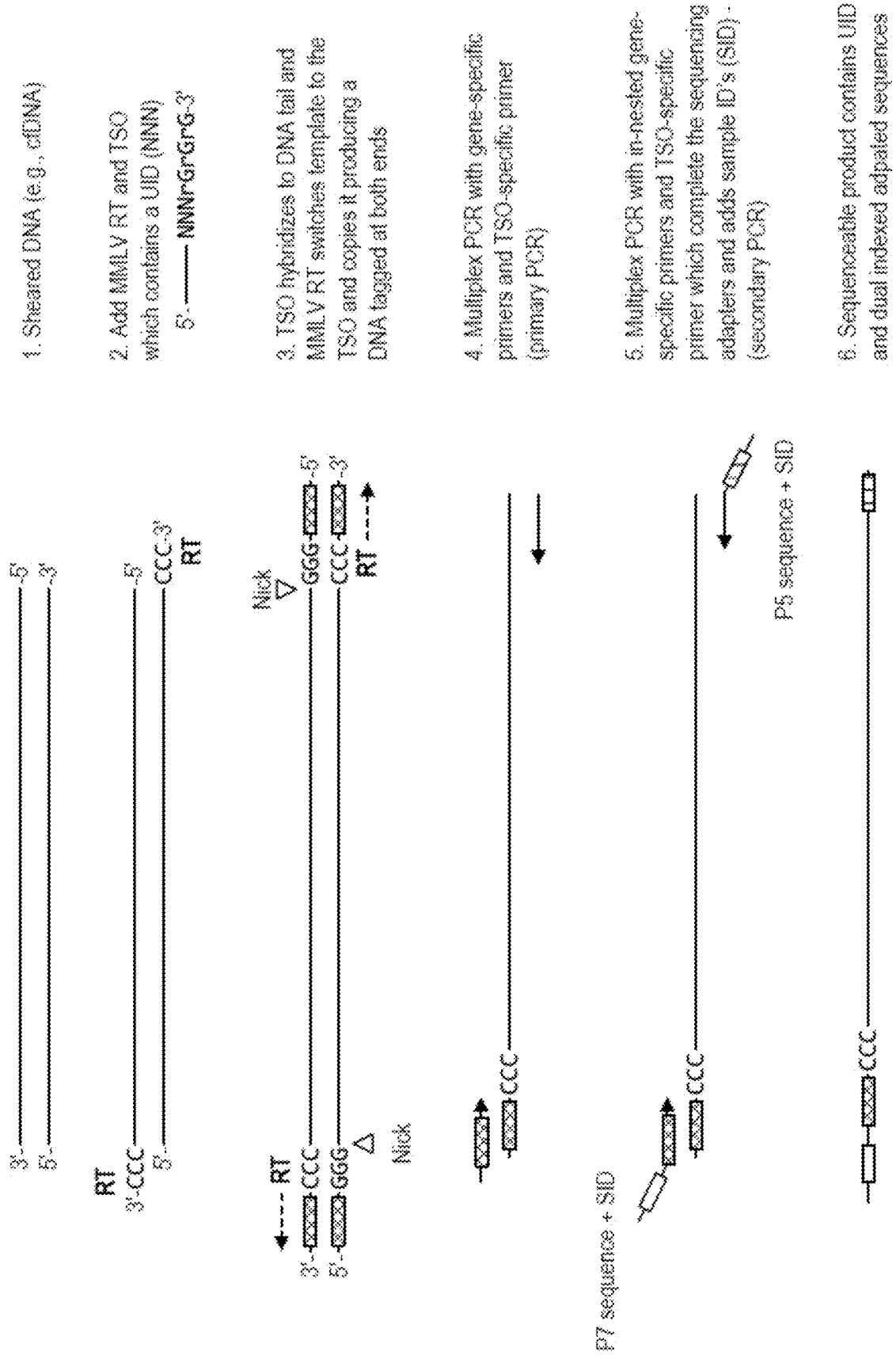
FIG. 5 is a drawing of a method by which an adaptor sequence can be added to either end of a blunted ended double stranded DNA molecule through the use MMLV RT and a TSO.

Double-stranded DNAs (dsDNAs) of the disclosure, including, for example, those depicted in FIG. 5 (third step), are particularly useful when only one end of a target sequence is known (e.g. target sequences comprising novel fusion events) (see Examples 2, 3 and 4).

In some embodiments, a second or subsequent DNA amplification is performed. In some embodiments, a first DNA amplification is performed using a first primer that comprises a sequence complementary to a template sequence and a second primer comprising a sequence complementary to a sequence of an adaptor, wherein the first DNA amplification can, for example, amplify a desired sequence from a dsDNA template or template library, and a second PCR amplification is performed using a pair of primers that are "nested" with respect to the first and second primers, respectively. For example, a second PCR amplification is performed using a pair of primers that are "in-nested" with respect to the first and second primers, respectively, meaning that one or more of the pair of primers used in the second PCR amplification comprise a sequence that is complementary to a sequence of the dsDNA that is further 3' than the 5' primer or further 5' than the 3' primer. In some embodiments, the product of the second PCR amplification comprises fewer nucleotides than the product of the first PCR amplification. In some embodiments, the product of the second PCR amplification consists of fewer nucleotides than the product of the first PCR amplification. In some embodiments, the product of the second PCR amplification is shorter than the product of the first PCR amplification.

In some embodiments, primers of the disclosure comprise having one or more SID or UID sequences to provide a sample index, or an additional sequence identifier for a subsequent application or step.

In some embodiments, one or more primers used in the first PCR amplification comprises an SID and/or UID sequence, thereby incorporating the SID and/or UID sequence into the product of the first PCR amplification.

In some embodiments, one or more primers used in the second PCR amplification comprises an SID and/or UID sequence, thereby incorporating the SID and/or UID sequence into the product of the second PCR amplification.

Amplification Single Stranded DNA

In some embodiments of the methods of the disclosure, the methods uncouple an extension step and a template-switching (e.g. adaptor addition) step. The uncoupling of extension and a template-switching steps expands the range of starting materials to which the methods of the disclosure may be applied.

In some embodiments of the methods of the disclosure, a DNA template of the disclosure is extended by denaturing a fragmented double stranded DNA (dsDNA), annealing a primer to the denatured dsDNA and extending the sequence of the dsDNA:primer complex by contacting the dsDNA:primer complex and a high-fidelity DNA polymerase to produce a dsDNA extension product. In some embodiments, the dsDNA extension product, a template switching oligonucleotide (TSO) and an enzyme capable of terminal transferase activity and template switching (e.g., a MMLV RT)

are contacted under conditions suitable for terminal transferase and template switching activity. In some embodiments, conditions suitable for terminal transferase and template switching activity include a temperature at which the DNA polymerase is mostly inactive but the enzyme capable of terminal transferase activity and template switching (e.g. MMLV RT) is active, resulting in the addition of a 3' adaptor sequence to the DNA strand synthesized during the extension step. During the template-switching step, the enzyme capable of terminal transferase activity and template switching (e.g. MMLV RT) then switches strands and extends the strand complementary to the TSO in the 5' to 3' direction to generate a single stranded DNA (ssDNA) product comprising a sequence identical to a sequence of the template DNA and a 3' adaptor sequence that is complementary to a sequence of the TSO. In some embodiments, excess or unbound primer(s) are removed through the addition of a nuclease to the extension and/or template switching reactions. In some embodiments, the ssDNA product is amplified using, for example, a first primer comprising a sequence complementary to the template DNA of the ssDNA product and a second primer comprising a sequence complementary to a sequence of an adaptor of the ssDNA. In some embodiments, either the first primer or the second primer further comprise a second or subsequent adaptor sequence.

Fusion Detection by Template Switching and Amplicon Sequencing

Figure 9:
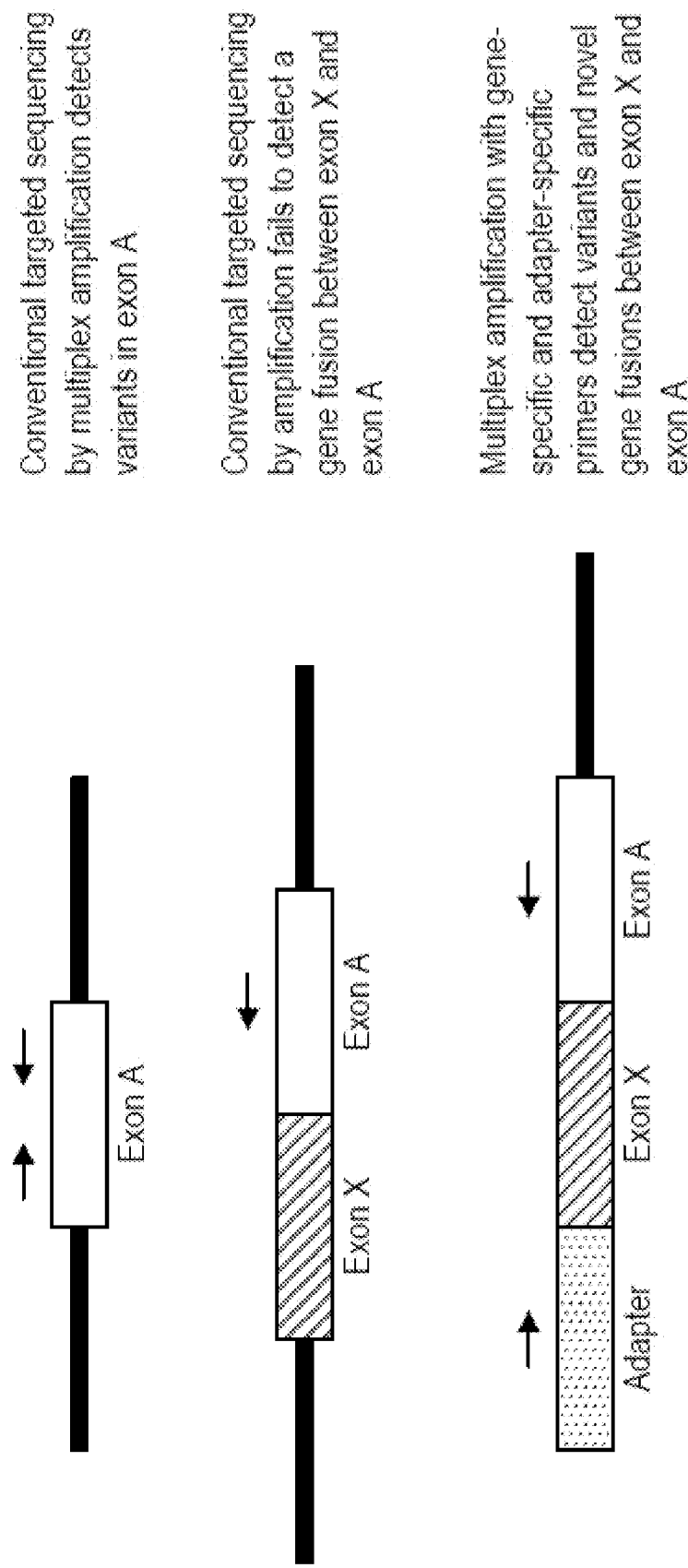
FIG. 9 is a diagram illustrating the problem of detecting novel gene fusion events, and how these events might be detected through the use of the adaptor sequences and methods of the disclosure.
Figure 10:
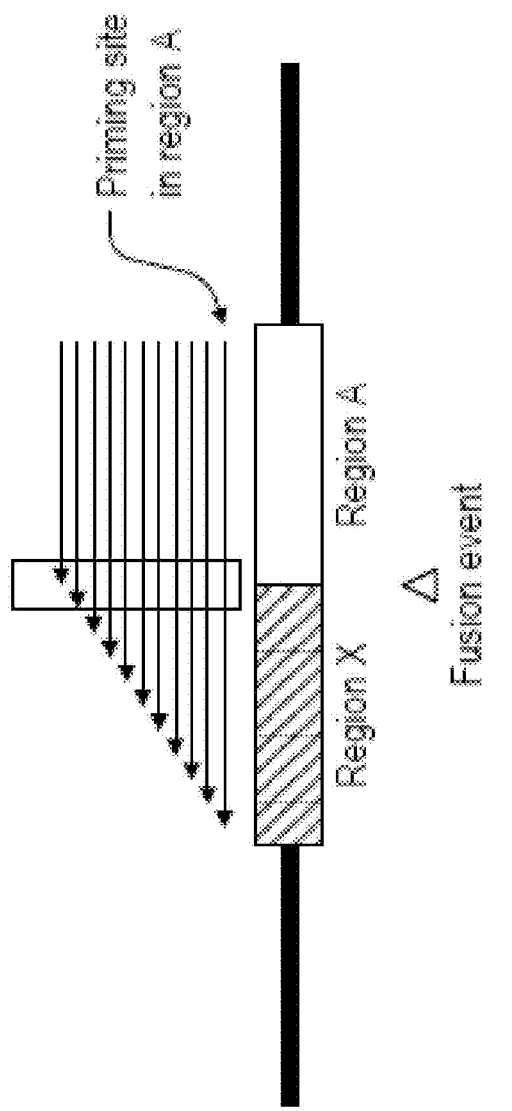
FIG. 10 is a diagram illustrating how sequencing reads generated with an adaptor such as the one used in the template switching method of the disclosure are capable of detecting novel fusion events.

The addition of an adaptor sequence at both ends of a dsDNA template library provides a solution to the problem of detecting fusion events which are missed by more conventional methods (e.g. amplicon sequencing technologies) (FIG. 9). By adding an adaptor to the template DNA library, and amplifying with primers specific to the adaptor and to the gene of interest in the fusion event, it is possible to generate a range of amplicon fragments that are anchored on one end in the gene or region of interest in the fusion event (FIG. 10, region A), and within the adaptor sequence on the other. These amplicon fragments span the join between the two sequences that are fused (region A/region X join in FIG. 10).

Figure 11:
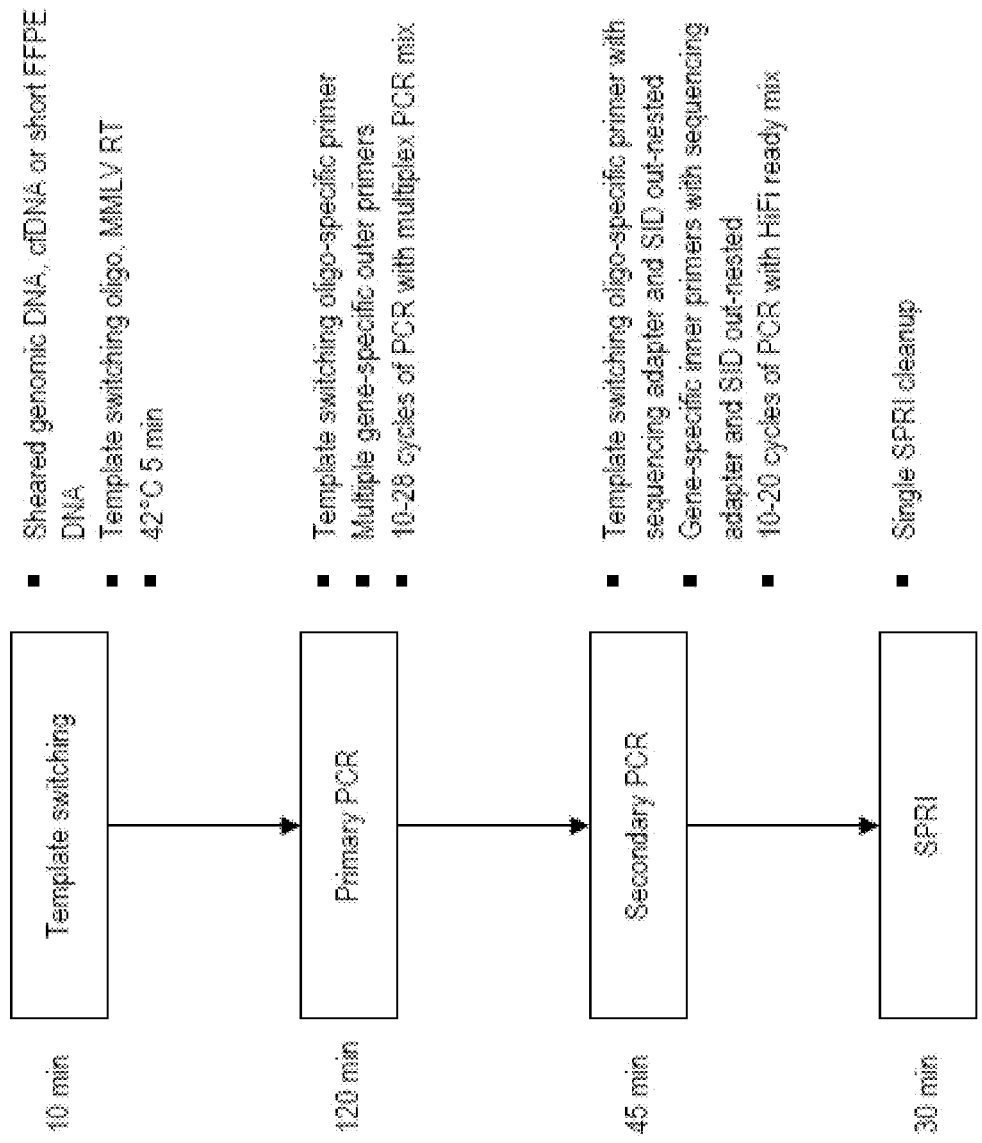
FIG. 11 is a diagram illustrating the workflow for generating sequencing-ready PCR product using the methods of the disclosure.

The use of a template switching compositions and methods of the disclosure provide significant advantages when compared to conventional ligation reactions, particularly in terms of workflow. The compositions and methods of the disclosure transform raw template dsDNA or ssDNA into sequencing-ready samples in four hours (FIG. 11). In contrast, traditional ligation protocols using T4 DNA ligase require at least one overnight incubation step.

Exemplary workflow for detecting fusion events using a 31 primer panel is shown in FIG. 5 and mirrors the compositions and methods described in Example 2. Two alternative, exemplary, designs were explored for the design of the TSO and for multiplex PCR reactions following the template switching steps of the disclosure (FIG. 12).

In the first strategy, a TSO 1202 (labeled R1-TSO), comprises both a sequence 1204 complementary to the poly(C) sequence added by the MMLV RT and an extended primer sequence 1206, which, in some embodiments, includes a UID sequence (FIG. 12). A first round PCR step 1207 was carried out with a forward primer 1208 that hybridized to this extended TSO sequence 1202 and added an SID 1210, and a reverse primer 1212 that bound the template sequence 1214 at a region 1215 adjacent to the region of interest 1216 (FIG. 12, top left panel). The second PCR step 1217 (FIG. 12, bottom left panel) was carried out with a primer 1218 specific to the indexing primer sequence 1210 introduced in the first round PCR step 1207 (primer 1208), a second in-nested template specific primer (1220) and a second indexing primer 1222, which also contained an SID 1224), therefore incorporating additional sequences into the template sequence 1214 resulting in the product 1226. Notably, the primer 1220 and the primer 1222 each have the shared sequence 1227. In the second strategy, the ME-TSO strategy (FIG. 12, right hand panels), the TSO 1242 itself includes minimal sequence elements. SID 1244, UID 1246 and additional sequences 1248 were added to the template sequence 1214 through their inclusion on primers 1250, 1252, 1254, 1256 and 1258 during the two progressive rounds of PCR (steps 1260 and 1262, resulting in the a final product 1264 having features equivalent to the product 1226 derived from the R1-TSO strategy. In this embodiment the dual indexing is carried out in the second PCR step 1262, thus simplifying the workflow. Notably, the primer 1256 and the primer 1258 each have the shared sequence 1259.

Human genomic DNA was prepared for analysis using several different strategies prior to template switching and amplicon sequencing. In the first, Covaris-sheared human genomic DNA (Genotype NA12878, Coriell Institute, 300 bp median distribution) was end repaired using the Kapa End Repair module. In the second, the human DNA was fragmented enzymatically using the Kapa Frag enzyme. Sheared or enzymatically fragmented DNA was then used in the template switching reaction with either the R1-TSO or ME-TSO TSO, and the resulting reaction product either purified using SPRI or used directly as the template for the first round PCR reaction. A tagmentation library prepared from 10 ng genomic DNA and Tnp was used as a control ("Sterling" control with the METsome or R1 Tsome). The tagmentation-based protocol is a positive control anchored PCR technique which does not utilize template switching, but is compatible with the primer design used for the template switching methodologies.

Human DNA from the template switch reactions was then used as a template with a panel of 31 template specific primers. When reads from this panel were aligned with the EGFR (FIGS. 14 and 15) and Kit (FIG. 16) loci, results from the template switching reactions compared favorably with the "Sterling" control. When the average insert sizes were calculated, the reads generated using the R1-TSO primer compared favorably to the Sterling control, with the bulk of the reads in the 150-250 base pair size range (FIG. 17). Reads produced with the R1-TSO also had the highest on-target rates, with on-target rates at greater than 80% (FIG. 18), out-performing the "Sterling" control and ME-TSO under most conditions. The R1-TSO consistently out-performed the "Sterling" control in terms of panel coverage uniformity (FIG. 19). ME-TSO also out-performed the "Sterling" control with certain types of input DNA at some loci (end-repaired and cleaned up DNA, enzymatically fragmented DNA used directly in the first PCR). Enzymatically fragmented and cleaned up DNA consistently out-performed the "Sterling" control in terms of target coverage (FIG. 19), while DNA reacted with ME-TSO that was used directly in the first PCR reaction had the most uneven target coverage. The template switching reactions in which the template DNA was enzymatically fragmented had a higher percent of unique reads than when the template DNA was sheared and end repaired (FIG. 20), although the enzymatically fragmented DNA with R1-TSO that was cleaned up did not perform as well as the other samples. GC content bias is a well-known problem in high throughput sequencing: GC rich fragments can be under- or over-represented in sequencing results. We estimated the extent of the GC content bias using the CollectGCBiasMetrics program from the Picard Tools suite (github.com/broadinstitute/picard), which provides a GC dropout metric for an NGS library by comparing the observed GC content of the library to the (idealized) expected GC content of the target loci. The magnitude of the value of the GC dropout metric serves as a relative estimate of the under-representation of GC-rich genomic fragments in the library. The enzymatically fragmented and cleaned up DNA reacted with the R1-TSO and ME-TSO had the lowest calculated GC dropout values (FIG. 21).

Uncoupling the Extension and Template Switching Reactions

The methods of the disclosure can comprise an extension step and a template-switching (adaptor addition) step, while uncoupling the extension and template-switching steps, allowing the method to be applied to a single stranded DNA (ssDNA) template. The method may comprises the steps of denaturing a fragmented double stranded DNA (dsDNA) to provide an at least partially single stranded ssDNA 2102, annealing a primer 2104 to the ssDNA to form a ssDNA:primer complex and extending the ssDNA:primer complex using a high-fidelity DNA polymerase (e.g. Kapa HiFi, SEQ ID NO: 1 or 3, FIG. 22 step 1) to produce an extension product 2106. The extension product 2106, a TSO 2108 and an enzyme capable of terminal transferase activity and template switching (e.g. MMLV RT) are contacted under conditions sufficient for terminal transferase and template switching activity (the reaction is incubated at a temperature where the DNA polymerase is mostly inactive but the MMLV RT is active, resulting in the addition of a 3' adaptor 2110 to the synthesized strand). The MMLV RT then switches strands to extend the adaptor sequence 2110 complementary to the TSO 2108 in the 5' to 3' direction (FIG. 22, step 2). The addition of an exonuclease removed excess amplicon, TSO, and primers. The exonuclease is neutralized either by heating the reaction or by purifying the reacted template DNA 2102 (FIG. 22, step 3). Finally, a polymerase and PCR primers 2112 and 2114 that hybridize to the template sequence 2106 and the TSO 2110, which optionally contain SIDs 2116, are added to produce a dsDNA 2118 ready for sequencing (FIG. 22, step 4). This method includes a single round of PCR to produce a sequencing ready PCR product comprising a UID 2120 provided by the TSO 2110. This method is expected to increase specificity by ensuring that only (specifically primed and extended) products are subjected to template switching.

EXAMPLES

In order to better understand the embodiments of the disclosure, the following examples are provided. These examples are intended to be illustrative, and do not limit the scope of the disclosure.

Example 1: Addition of Adaptor Sequence to Double Stranded DNA Templates

Figure 1:
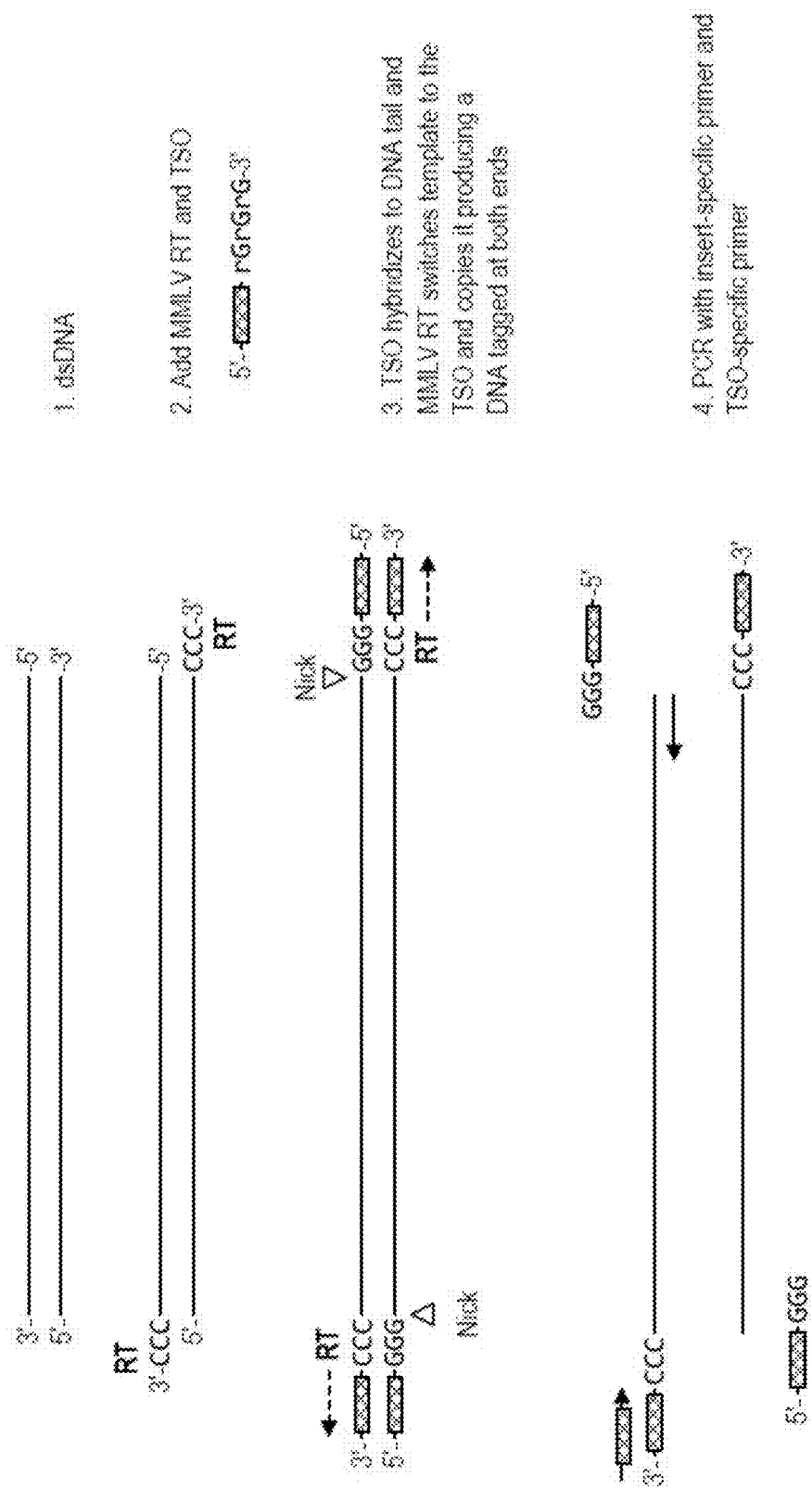
FIG. 1 is a drawing of a method by which an adaptor sequence can be added to either end of a blunted ended double stranded DNA molecule through the use of a Moloney murine leukemia virus reverse transcriptase (MMLV RT) and a template switching oligo (TSO).

Summary of Methods:

A double stranded DNA template, such as a fragmented DNA (mechanically, enzymatically or natively—e.g., a cfDNA) or a PCR product was provided. This dsDNA template was then contacted with a TSO and MMLV RT. The reaction was incubated at 42° C. for 10 minutes. The terminal transferase activity of MMLV RT added an adaptor sequence to the 3' end of each strand of the template (FIG. 1, polyC sequence in step 2). The TSO hybridized to the 3' adaptor sequence of the dsDNA template and the MMLV RT switched strands from the template to the TSO, synthesizing a strand complementary to the DNA template that incorporates the TSO sequence. The template-switching step resulted in the addition of the adaptor sequence to the 3' end of each strand of the template DNA (FIG. 1, step 3), referred to herein as a dsDNA intermediate. The dsDNA intermediate was then used as substrate for PCR with template/gene-specific primers and adaptor-specific primers (FIG. 1, step 4). In some embodiments of the disclosure, template-specific primers are multiplexed.

Experimental Protocol:

A 153 base pair (bp) PCR product was used as template for a template switching reaction. 10 nanograms (ng), 1 ng, 100 picograms (pg) or 0 pg of purified 153 bp blunt PCR product produced with Kapa HiFi polymerase (encoded by the sequence of SEQ ID NO: 1 and 2) was used as template. To this, 10 picomoles (100 ng) of TSO, 200 Units of MMLV RT, dNTPs and reaction buffer were added and the mixture was incubated at 42° C. for 5 minutes. An additional set of reactions was performed where the MMLV RT was omitted (FIG. 2 and FIG. 3, +RT reactions are in the top panels, −RT reactions are in the bottom panels). Following a 2×SPRI clean-up with Kapa Pure beads, the resulting products were subjected to real-time amplification with Kapa SYBR Fast, using the following primer combinations: (a) forward TSO-specific and reverse template-specific primers (FIG. 2) and (b) forward and reverse primers specific to the template only (FIG. 3), and (c) a negative control reaction with TSO-specific forward primer only (no amplification after 35 cycles).

When the template switching product DNA was amplified with the forward TSO-specific and reverse template-specific primers (FIG. 2), the results indicated that addition of TSO sequence by template switching occurred linearly in the 10 ng to 100 pg input range and required the presence of MMLV RT. Conversely, when the template switching product DNA was amplified with forward and reverse template-specific primers (FIG. 3), the +RT and −RT reactions amplified after approximately the same number of cycles, unlike the PCR reactions carried out with TSO and template specific primers (FIG. 2).

Figure 4:
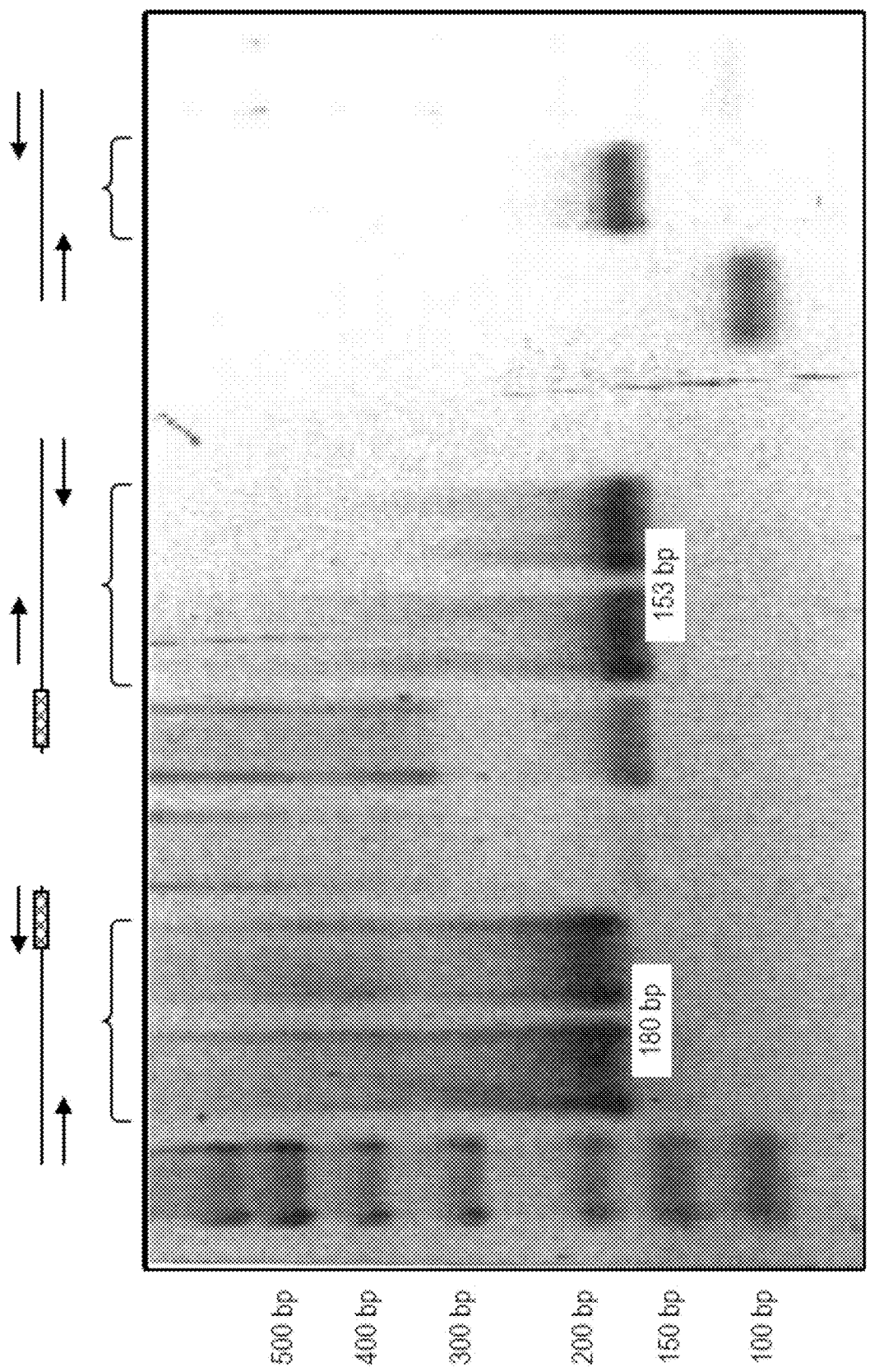
FIG. 4 is a picture of a gel showing the sizes of PCR products, with diagrams of the PCR templates and positions of the PCR primers for the PCR reactions shown at top. The y-axis indicates the size of the bands, with a DNA ladder loaded in the extreme left and right hand columns. The size of the bands of the DNA ladder are indicated to the left. From top to bottom, the labeled bands are 500 bp, 400 bp, 300 bp, 200 bp and 100 bp. In the diagrams of the PCR reactions, the template sequence is indicated in black, the TSO sequence as a hatched box, and primers are drawn as arrows parallel to the template and/or TSO sequence.

The real-time amplified PCR products were analyzed by agarose gel electrophoresis to confirm the addition of template switching oligo sequence (FIG. 4). The resulting product of the 153 bp template and template switching reaction was amplified with the following primer combinations: (a) combination of TSO-specific primer and template-specific primer (producing a 180 bp product, FIG. 4, lanes 2 and 3) and (b) forward and reverse primers specific to the template only (producing a 153 bp product, FIG. 4, lanes 6 and 7). Template which was not subject to template switching was also amplified with the template-specific forward and reverse primers (FIG. 4, lane 9). The results in FIG. 4 indicate that the template switching reaction added an additional 27 bp in length to the target template, as predicted based on length of the TSO.

Example 2: Multiplexed Targeted Amplification for Fusion Detection from Sheared DNA with UID Addition A diagram of the workflow for this example is shown in FIG. 5. Double stranded sheared DNA was subjected to template switching using a template switching oligo which had the partial sequence of a platform-specific adaptor and also contained a Unique Identifier (UID) sequence. MMLV RT added the poly(C) sequence of the adaptor to each end of the blunt ended double stranded DNA template. (FIG. 5, step 2). The TSO hybridized to the poly(C) sequence of the adaptor, and MMLV RT switched strands from the template to the TSO and copied the TSO to produce a dsDNA comprising an adaptor sequence at both ends. The UID was incorporated into the 3' adaptor sequence during the template switching reaction. In some embodiments, the UID identifies individual template molecules (FIG. 5, step 3). The primary PCR used template (or gene) specific primers and a TSO-specific primer. The primary PCR enriched the library for uniquely-tagged gene-specific fragments (FIG. 5, step 4). Next, a secondary PCR was performed with in-nested template specific primers which contained 5' regions that harbored sample identifiers (also known as SIDs) as well as the remainder of the platform-specific adaptor sequence, and with TSO-specific primers with 5' regions containing SIDs and the remainder of the other sequencing adaptor (FIG. 5, step 5). Following the secondary PCR, the products contained adaptor sequences which comprised UIDs and SIDs and were ready for sequencing.

An exemplary TSO used for template switching reaction in this example comprises the sequence:

```
                                                 (SEQ ID NO: 12)
5' TCGTCGGCAGCGTCAGATGTGTATAAGAGACAGNNNNNNNNrGrGr
G 3'.
```

The "rGrGrG" sequence indicates RNA bases (i.e. guanine RNAs) which were used for hybridization during template switching. "N" indicates the UID which will be read as the first 8 bases during sequencing. The read 1 sequencing primer anneals to the GAGACA sequence immediately upstream of the UID. The first 8 bases read will be part of the UID, followed by GGG. The next base read will be insert-derived. The UID-GGG sequence serves as a means of identifying the start of the gene specific region in the read.

Example 3: Addition of Adaptors to Sheared DNA by Template Switching Followed by Multiplex PCR with Gene-Specific and Adaptor (TSO)-Specific Primers to Simulate Fusion Detection The workflow for this example is summarized in FIG. 6.

Figure 6:
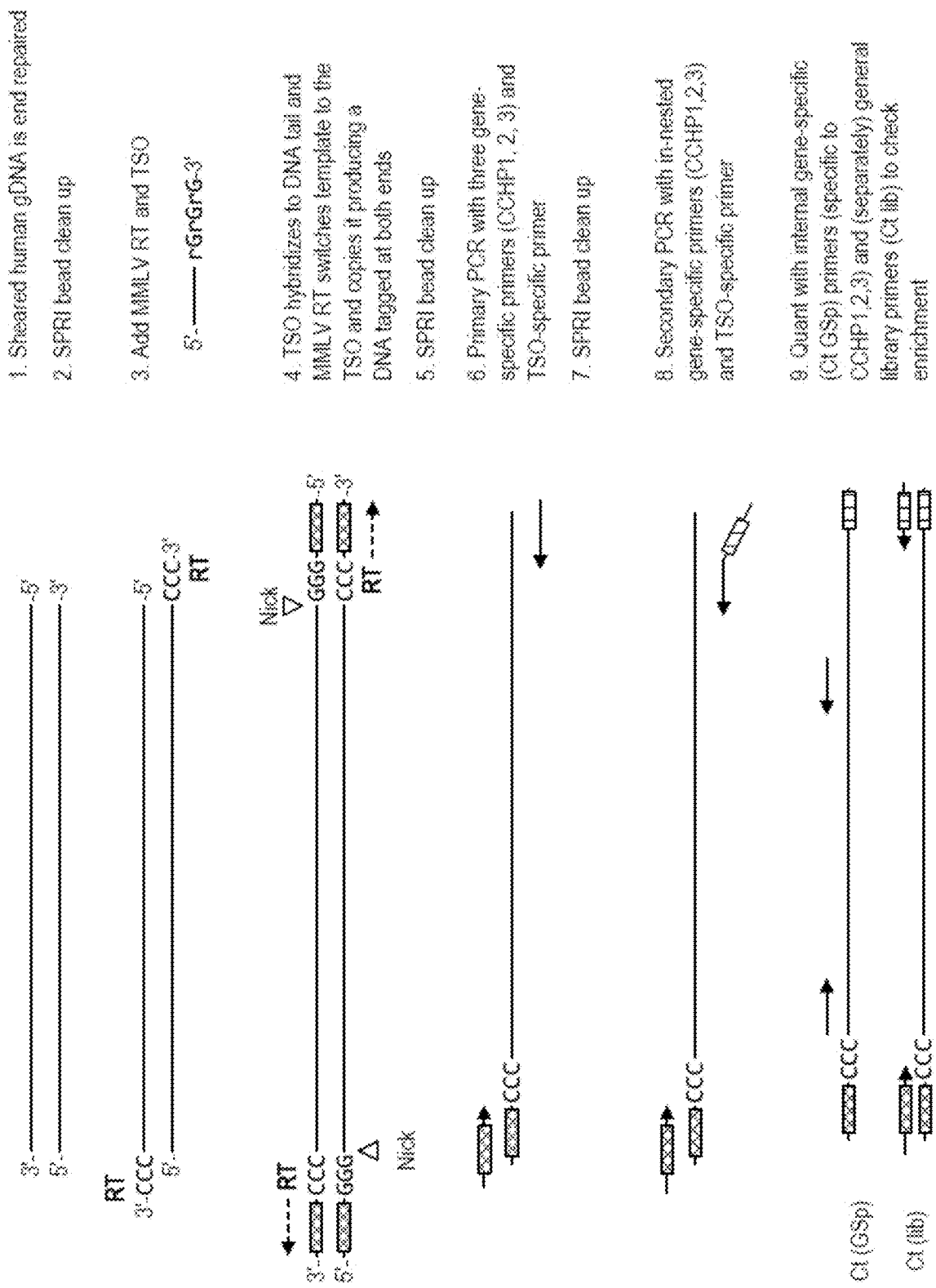
FIG. 6 is a drawing of a method by which an adaptor sequence can be added to either end of a blunted ended double stranded DNA molecule through the use of MMLV RT and a TSO to generate a sequencing library.
Figure 7A:
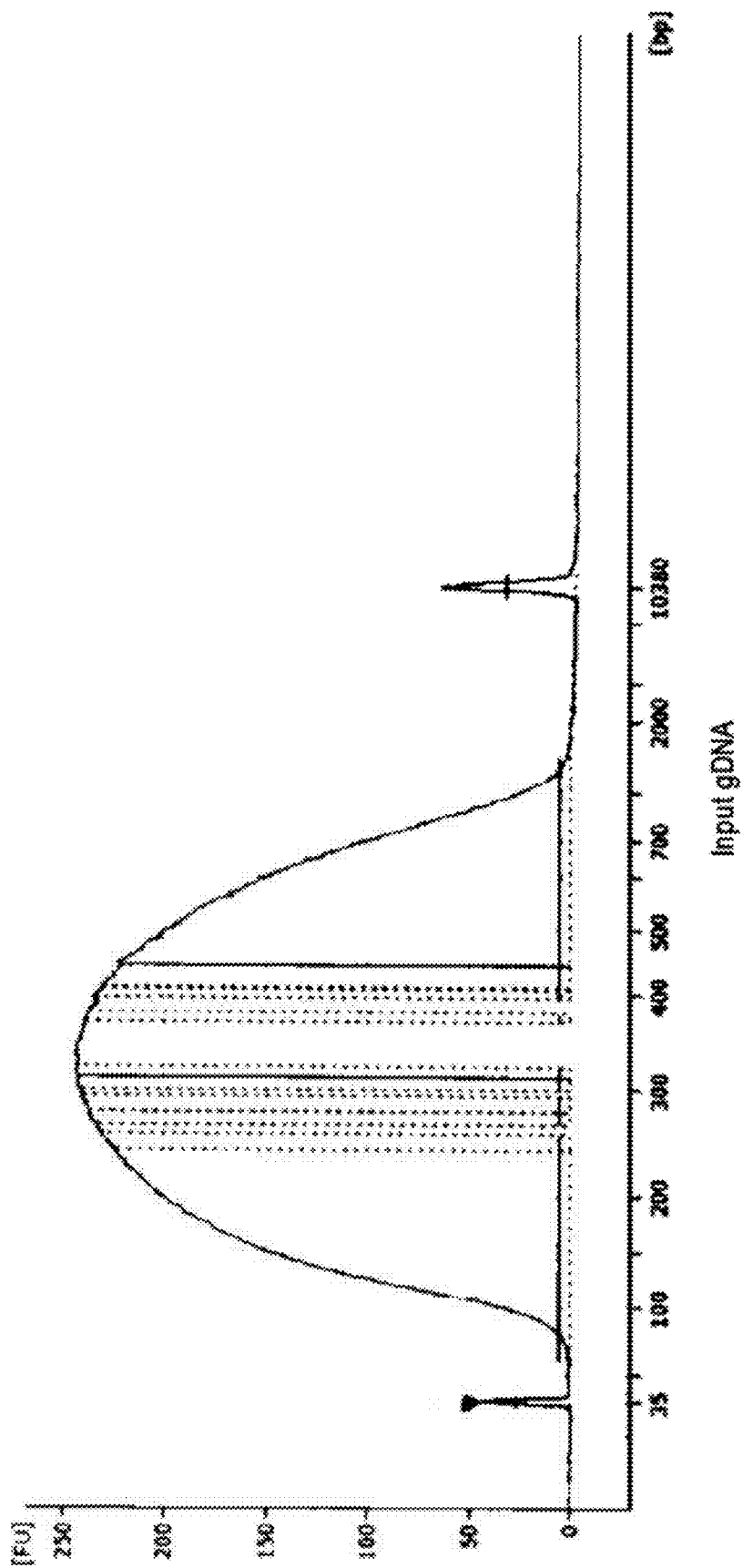
FIG. 7A is a graph showing the size distribution of Covaris-sheared human genomic DNA fragments analyzed using a BioAnalyzer High Sensitivity Assay. On the x-axis is plotted input fragment size in base pairs (bp). Sizes are labeled from left to right at 35 bp, 100 bp, 200 bp, 300 bp, 400 bp, 500 bp, 700 bp, 2,000 bp and 10,380 bp. On the y-axis, fluorescence intensity [FU], incrementing in intervals of 50 from 0 to 250. Peak labels indicated by dashed vertical lines are from left to right: 35, 240, 256, 275, 290, 314, 315, 372, 398, 413, 448, and 10380.

Covaris-sheared human genomic DNA (Promega, 300 bp median distribution) was end repaired using the Kapa End Repair module and purified using SPRI (FIG. 6, steps 1 and 2). Characteristics of the input genomic DNA (gDNA) are shown in FIG. 7A. When the gDNA was analyzed using a BioAnalyzer High Sensitivity assay, it exhibited a distribution with a median of 300 bp. 5 ng, 500 pg, 50 pg or 0 pg of this material was used as input in template switching reaction in the presence of 200U MMLV RT, 20 picomoles of TSO, dNTPs and 1×RT buffer. The reactions were incubated for 10 minutes at 42° C. for 10 minutes. An additional set of reactions was performed where the MMLV RT was omitted (-RT reactions). MMLV RT added the poly(C) sequence of the adaptor to each end of the blunt ended double stranded DNA template. The TSO hybridized to the poly(C) sequence of the adaptor, and MMLV RT switched strands from the template to the TSO and copies the TSO to produce a dsDNA tagged at both ends (FIG. 6, step 3 and 4).

Figure 7B:
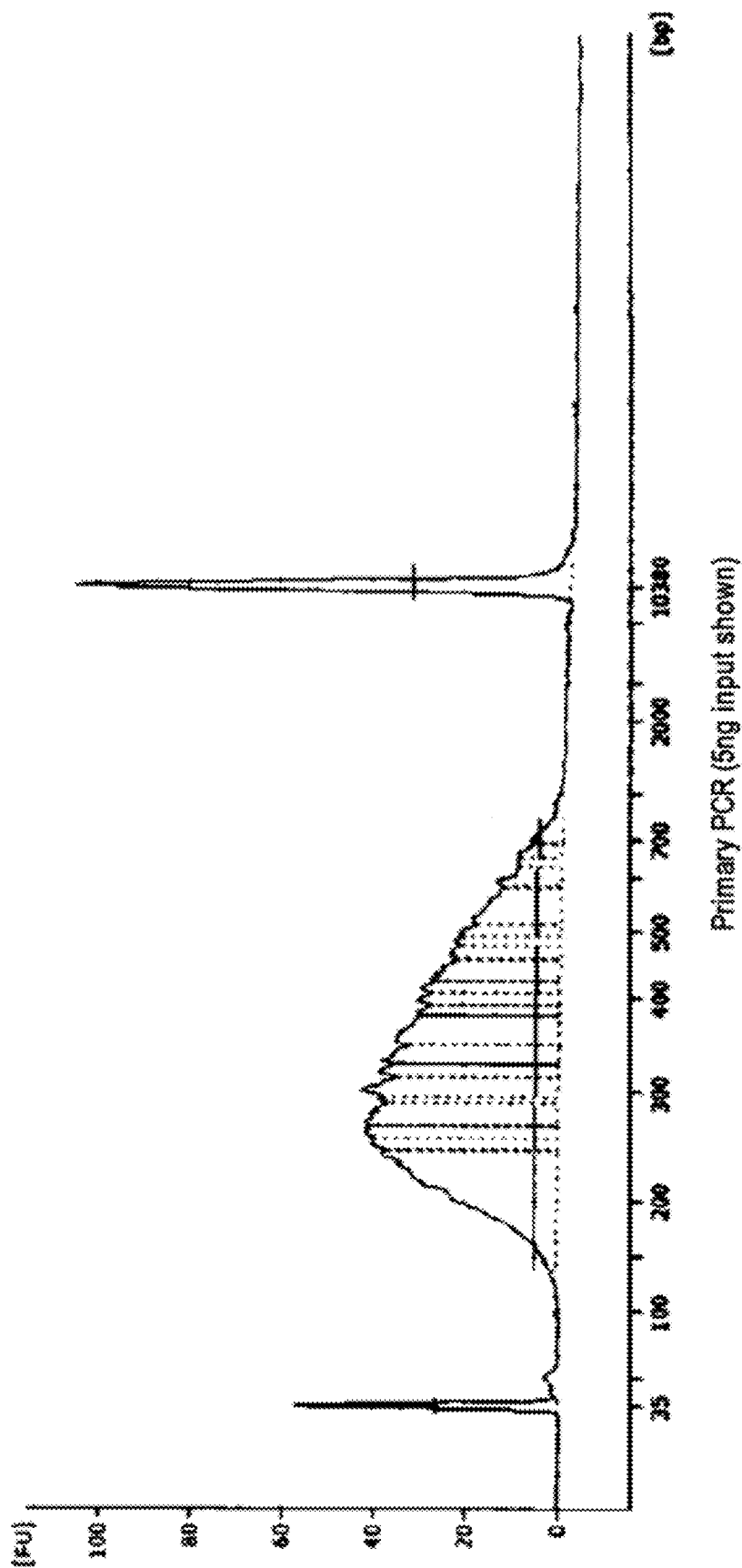
FIG. 7B is a plot showing the size distribution of first round primary PCR products, consisting of fragments with the TSO sequence at one end the CCHP1, CCHP2 and CCHP3 primer sequences at the other end, analyzed using a BioAnalyzer High Sensitivity Assay. On the x-axis is plotted input fragment size in base pairs (bp). Sizes are labeled from left to right at 35 bp, 100 bp, 200 bp, 300 bp, 400 bp, 500 bp, 700 bp, 2,000 bp and 10,380 bp. On the y-axis, fluorescence intensity [FU], incrementing in intervals of 20 from 0 to 100. Peak labels indicated by dashed vertical lines are from left to right: 35, 248, 260, 273, 302, 322, 332, 358, 385, 386, 414, 426, 465, 496, 522, 591, 663, 699, and 10380.

Following a 2×SPRI clean-up with Kapa Pure beads (FIG. 6, step 5), the template was amplified in a primary PCR reaction (shown in FIG. 6, step 6) using the TSO-specific primer and three gene-specific primers from the comprehensive cancer hot spot panel (CCHP1,2 and 3). The primary PCR reaction used a custom multiplex PCR cycling mix for 23 (5 ng input library), 26 (500 pg input library) or 28 cycles (50 pg input library and NTC library). The primary PCR product from the 5 ng input library was analyzed using a BioAnalyzer High-sensitivity assay (FIG. 7B). When the primary PCR product (product from step 6 in FIG. 6), consisting of fragments with the TSO sequence at one end and the CCHP 1, 2 and 3 sequences at the other end, was analyzed using the BioAnalyzer, it exhibited a distribution similar to that seen in the original input DNA. This product was subsequently used as template in step 8 of FIG. 6 to conduct the secondary PCR.

Figure 8:
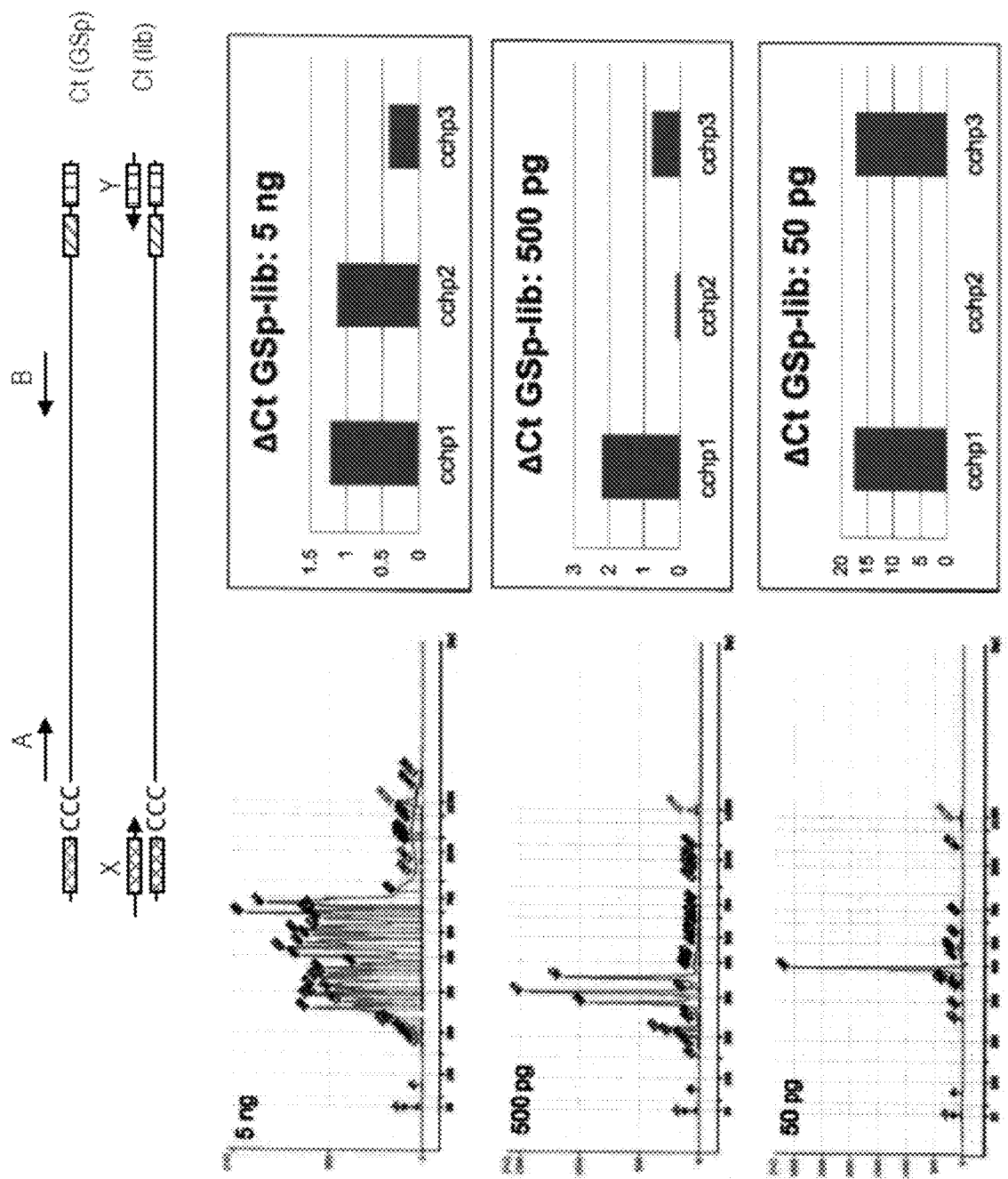
FIG. 8 is a series of graphs with a diagram of primer binding sites at the top, which shows additional analysis of the library generated using the diagram of FIG. 6 and the genomic DNA and PCR product characterized in FIG. 7. At top, a diagram of the primer sets used to characterize the library. Gene specific primers (Gsp, arrows A and B) amplify from within the template DNA sequence, while library (lib) primers (arrows X and Y) hybridize to sequences within the TSO (hatched box) and opposing adapter region (vertical lined box). At left, the secondary PCR product amplified from 5 nanograms starting material (top panel), 500 picograms (middle panel) or 50 picograms (bottom panel), consisting of fragments with the TSO sequence at the 5' end and the CCHP1, CCHP2 and CCHP3 sequences at the 3' end, was analyzed using the BioAnalyzer High Sensitivity assay. Each of the left three panel shows fragment size distribution on the x-axis in base pairs (labeled, from left to right at 35 bp, 100 bp, 200 bp, 300 bp, 400 bp, 500 bp, 700 bp, 2,000 bp and 10,380 bp), with fluorescence intensity [FU] on the y-axis. In the top left panel, [FU] is labeled from 0 at the bottom to 1000 in increments of 500. In the middle left panel, [FU] is labeled from 0 at the bottom to 1500 in increments of 500. In the bottom left panel, [FU] is labeled from 0 at the bottom to 3,000 in increments of 500. The three right hand panels show enrichment for the genes of interest corresponding to the CCHP1, CCHP2 and CCHP3 primers in three libraries generated from 5 nanograms starting material (top panel), 500 picograms of starting material (middle panel) or 50 picograms of starting material (bottom panel). In each right hand panel, the gene of interest is given on the x-axis, and the change in crossing point metric ΔCt Gsp-lib on the y-axis. The enrichment of the library for genes of interested was assessed by real time PCR using the secondary PCR product as input, with library-specific primers (which amplify all fragments) producing the crossing point Ct(lib), and with the three gene-specific primer combinations, CCHP 1, 2 and 3, producing the crossing points Ct(Gsp) for each of the three targets. The metric of ΔCt Gsp-lib was calculated for each of the three target genes by subtracting the Ct(lib) from the Ct(Gsp). The lower the value, the more enriched the library is for that particular target gene. Small differences in ΔCt Gsp-lib between the three gene targets indicate that the targets are represented uniformly in the library.

Half of the SPRI-purified primary PCR products were used as template for the secondary PCR, using the TSO-specific primer in combination with inner gene specific primers (in-nested relative to the gene specific primers used in the primary PCR). This reaction is shown in step 8 of FIG. 6. The in-nesting was performed to improve specificity, but could feasibly be omitted in a single PCR workflow. The secondary PCR was performed using Kapa HiFi Hot Start Ready Mix (Kapa HiFi HS RM). The secondary PCR products were SPRI-purified and analyzed using a BioAnalyzer High-sensitivity assay (FIG. 8, left hand panels). When the secondary PCR product, consisting of fragments with the TSO sequence at one end and the CCHP1, 2 and 3 sequences at the other end, was analyzed using the BioAnalyzer the Library from 5 ng of input showed a characteristic distribution of discrete fragments (FIG. 8, top left), with sizes suitable for short read sequencing. The libraries from 500 pg and 50 pg (FIG. 8, middle and bottom left panels) showed considerably less complex profiles, indicating reduced complexity.

The effectiveness of the enrichment of the various inputs was assessed by qPCR using library-specific primers which amplify all the library fragments, and template/gene-specific primers which amplify a short section of the targeted loci (FIG. 6, step 9). The real time PCR used the secondary PCR product as input, and either library-specific primers (that bound sequences in the TSO) and amplified all fragments, producing the crossing point Ct(lib), or three gene-specific primer combinations, CCHP 1, 2 and 3, which produced the crossing points Ct(Gsp) for each of the three targets. The difference in crossing point (Ct value) between the library-specific and each template/gene specific primer set (L~Ct) indicates how much of the library is composed of each of the target loci (FIG. 8). A high ~Ct indicates that a small proportion of the library is composed of that particular target. FIG. 8 illustrates that a fragment library produced using the method from 5 ng of input sheared human genomic DNA is highly enriched for the three targets of interest and the three targets are represented fairly evenly (~Ct values for CCHP1, 2 and 3 are not very discordant). As the input is decreased to 500 pg, the library complexity decreases and the enrichment for the three target genes decreases as does the uniformity of enrichment (~Ct values for CCHP1, 2 and 3 are discordant). Lastly, a library prepared from 50 pg of human genomic PCR consists almost entirely from one of the three targets, —CCHP2.

Importantly, no libraries which underwent the template switching reaction in the absence of MMLV RT produced any product, even after two rounds of extensive PCR amplification. In addition, no-template controls which underwent the TS reaction in the presence of MMLV RT produced no product after two rounds of extensive CR amplification. These data indicate that the process is relatively resistant to PCR artefacts and non-specific amplification. The reduction in complexity with decreased amounts of gDNA input may be related to the small target size (500 pg is less than 200 haploid genomes) and the use of multiple cleanups. The eventual optimized reaction will include direct PCR after TSO addition, leading to lower loss of target DNA.

These results together demonstrate that the method works in principle. MMLV RT is able to add an adaptor to the 3' end of sheared genomic DNA in the clinically-relevant size and concentration range of 300 bp fragments, with 5 ng or less of input. The resulting product is a suitable substrate for amplification with template/gene-specific and adaptor specific primers leading to a fragment library enriched for the genes of interest. Lastly, the method can be seen as a generic means of adding a 3' adaptor to a 3' end of a DNA template using only the TSO and the MMLV RT in a reaction.

Example 4: Determination of Mg2+ Concentration and Amount of Complementary Nucleotide for Effective Adapter Addition of the dsDNA Template The TSO used in this experiment were TSO-rG: where 5N and three RNA Guanine bases are separated by an H base. TSO-rG was used with all four dNTPs plus different concentrations of additional dCTP promote C-tailing of the dsDNA amplicon template. To adjust for the additional nucleotides, more Mg2+ was added. Tailing and template-switching of the amplicon was allowed to happen in the presence of all four nucleotides. The template-switched products are analyzed on a LabChip high sensitivity fragment analyzer and the molarity calculated. Three distinct species can be observed in the LabChip trace: 1) the dsDNA amplicon with no adapter addition, 2) the amplicon with an adapter added to one end, 3) and the amplicon with an adapter added on both ends. The ratio of these species to the total molarity is calculated and plotted (FIG. 24).

Ten (10) nanograms (ng) of purified 153 bp blunt PCR product produced with Kapa HiFi polymerase was used as template. The reactions contained 1 mM of each dNTP, with an additional dCTP added at 0 mM, 5 mM, 10 mM, or 20 mM. The reactions also contained reaction buffer and 200 U of MMLV RT. Reaction buffer includes either 0 mM, 12 mM, 24 mM, or 36 mM Mg2+. A control reaction with no added nucleotides was also included with 12 mM Mg2+. The reactions were incubated at 42° C. for 10 min. Following a 2×SPRI cleanup with Kapa Pure beads, the resulting product was loaded on the LabChip GX Touch High sensitivity DNA chip.

Mg2+ is required as a cofactor for the enzyme to function. Too much additional dCTP requires more Mg2+. At 24 mM Mg2+, additional 5 mM or 10 mM dCTP results in improvement over base line dNTPs (which contain 1 mM dCTP). 10 mM additional dCTP seems optimal both at 24 and 36 mM Mg2+, with more than 40% of the product having an adapter on one or both ends (FIG. 24).

Example 5: Use of Different RNA Bases in the TSO with Corresponding Complementary Nucleotide Incubation for Adapter Addition of the dsDNA Template The basic TSO sequence used in this experiment was as follows: the adapter sequence is followed by a 5N (five nucleotide) UMI, together with a spacer base separating the RNA tail from the DNA bases. In this example the TSO is tailed with 3 Uracil bases (with a V base spacer), or 3 Adenine bases (with a B base spacer), or 3 Cytidine bases (with a G base spacer), or 3 Guanine bases (with an H base spacer), all RNA bases. Another TSO was also tested with 3 N RNA bases, but with 6 N (6 nucleotide) UMI and no distinct spacer base. The template switching reaction was performed with only a single complementary nucleotide to the RNA base of the TSO, in contact with MMLV RT, and a dsDNA amplicon. Tailing of the amplicon with the single nucleotide was allowed for 20 min, after which the remaining 3 nucleotides were added and template switching and adapter addition allowed for 10 min. The template-switched products are analyzed on a LabChip high sensitivity fragment analyzer and the molarity calculated. Three distinct species can be observed in the LabChip trace: 1) the dsDNA amplicon with no adapter addition, 2) the amplicon with an adapter added to one end, 3) and the amplicon with an adapter added on both ends. The ratio of these species to the total molarity is calculated and plotted (FIG. 25).

Ten (10) nanograms (ng) of purified 153 bp blunt PCR product produced with Kapa HiFi polymerase was used as template. To this, 500 nM of TSO, 200 Units of MMLV RT, 1 mM of single nucleotide, and reaction buffer was added and the mixture incubated at 42° C. for 20 min. The remaining three nucleotides were then spiked-in at 1 mM each and incubated at 42° C. for 10 min. Controls for the experiment include: one reaction with no dNTPs added (performed with TSO-rN) and one reaction for each TSO with all the dNTPs added at once. Following a 2×SPRI cleanup with Kapa Pure beads, the resulting product was loaded on the LabChip GX Touch High sensitivity DNA chip.

Double adapter addition is most effective where the TSO-rC is used: either tailing with dGTP first, or tailing in the presence of all four nucleotides. Using TSO-rC with dGTP tailing allows for more than 50% of the total product to have a single or double adapter added to the DNA amplicon. TSO-rU and TSO-rA did not result in high double adapter-added product, indicating that the MMLV RT does not prefer A- or T-tailing. Using TSO-rN, tailing and adapter-addition is marginally better when tailing first with dCTP or dGTP, but most effective in the presence of all four nucleotides.

Example 6: Use of DNA Bases or RNA Bases in the TSO with Complementary Nucleotide Addition The basic TSO sequence used in this experiment is as follows: the adapter sequence is followed by a 5N UMI, together with a spacer base separating the tail from the DNA bases. In this example the TSO is tailed with 3 RNA Guanine bases, or 3 RNA Cytosine bases, or 3 DNA Guanine bases, or 3 DNA Cytosine bases. The Cytosine TSO has a D spacer base and the Guanine TSO has an H spacer base. The template-switching reaction was performed with all four nucleotides, and additional complementary nucleotide to the specific TSO used. Tailing and template-switching was allowed to occur for 10 min at 42° C. The template-switched products are analyzed on a LabChip high sensitivity fragment analyzer and the molarity calculated. Three distinct species can be observed in the LabChip trace: 1) the dsDNA amplicon with no adapter addition, 2) the amplicon with an adapter added to one end, 3) and the amplicon with an adapter added on both ends. The ratio of these species to the total molarity is calculated and plotted (FIG. 26).

Ten (10) nanograms (ng) of purified 153 bp blunt PCR product produced with Kapa HiFi polymerase was used as template. To this, 500 nM of TSO-rC, or TSO-rG, or TSO-dC, or TSO-dG, 200 Units of MMLV RT, 1 mM of single nucleotide, and reaction buffer was added. Additional 10 mM of the complementary nucleotide was added to the specific TSO reactions. A no TSO control was included with only 1 mM dNTPs added. The reactions were incubated for 10 min at 42° C. Following a 2×SPRI cleanup with Kapa Pure beads, the resulting product was loaded on the LabChip GX Touch High sensitivity DNA chip.

The Cytosine-tailed TSO seems to perform better than the Guanine-tailed TSO, irrespective of whether it is an RNA or DNA base, with more than 50% of the product having an adapter added. This suggests MMLV RT prefers G-tailing of dsDNA template over C-tailing, and does not have a template preference for DNA or RNA.

Example 7: Use of TSO-rG and TSO-rC in Different Ratios in One Reaction

A TSO with three Guanine bases (with an H spacer base) and a TSO with three Cytosine bases (with a D spacer base) were combined in different ratios and incubated with different amounts and combinations of nucleotides, either with no additional nucleotides, or with additional dCTP and/or with additional dGTP in the presence of 24 mM Mg2+. The template switching reaction was performed in the presence of MMLV RT and a dsDNA amplicon. Reactions were incubated with all the reaction components from the start for 10 min at 42° C. The template-switched products are analyzed on a LabChip high sensitivity fragment analyzer and the molarity calculated. Three distinct species can be observed in the LabChip trace: 1) the dsDNA amplicon with no adapter addition, 2) the amplicon with an adapter added to one end, 3) and the amplicon with an adapter added on both ends. The ratio of these species to the total molarity is calculated and plotted (FIG. 27).

Ten (10) nanograms (ng) of purified 153 bp blunt PCR product produced with Kapa HiFi polymerase was used as template. The dsDNA amplicon was incubated with MMLV RT and reaction buffer containing either 1 mM dNTPs, or 1 mM dNTPs+10 mM dCTP, or 1 mM dNTPs+10 mM dGTP, or 1 mM dNTPs+5 mM dCTP+5 mM dGTP. The reactions also contained: no TSO, or 500 mM TSO-rC or TSO-rG, or 500 mM TSO-rC and 500 mM TSO-rG, or 250 mM TSO-rC and 250 mM TSO-rG, or 400 mM TSO-rC and 100 mM TSO-rG, or 100 mM TSO-rC and 400 mM TSO-rG. The reactions were incubated at 42° C. for 10 min. Following a 2×SPRI cleanup with Kapa Pure beads, the resulting product was loaded on the LabChip GX Touch High sensitivity DNA chip.

Irrespective of the ratio in which the two TSOs are mixed, they result in more single and double adapter-added product than each TSO individually. A 4:1 rG:rC ratio does seem slightly less efficient. Adapter addition is enhanced by adding both additional complementary nucleotides with the mixture of TSOs, with almost 80% of the product having an adapter added.

Example 8: Comparative Efficacy of 5N UMI to a 7N UMI

This experiment consists of two parts. In the first part template-switching and adapter addition was done on a 153 bp amplicon. The amplicon product that had adapter addition via template-switching is analyzed on the LabChip high sensitivity fragment analyzer. Three distinct species can be observed in the LabChip trace: 1) the dsDNA amplicon with no adapter addition, 2) the amplicon with an adapter added to one end, 3) and the amplicon with an adapter added on both ends. The ratio of these species to the total molarity is calculated and plotted (FIG. 28). In the second part of the experiment the libraries were made with human genomic DNA with a combination of TSO-rC and TSO-rG, either having a 5N (5 nucleotide) UMI or a 7N (7 nucleotide) UMI. The 361Plus No tiling primer panel was used to make libraries with a nested PCR approach after tailing and template-switching of fragmented genomic human DNA. Libraries were sequenced on the NextSeq 500.

Ten (10) nanograms (ng) of purified 153 bp blunt PCR product produced with Kapa HiFi polymerase was used as template. To this, 500 nM of TSO-rC, or 500 mM of TSO-rG, or 250 mM TSO-rC+250 mM TSO-rG was added to 200 U MMLV RT, 1 mM dNTPs and reaction buffer. Additional single nucleotides were added to the complementary TSO: or 10 mM dGTP to TSO-rC, or 10 mM dCTP to TSO-rG, or 5 mM dCTP+5 mM dGTP to the TSO mixture. The reactions were incubated for 10 min at 42° C. Following a 2×SPRI cleanup with Kapa Pure beads, the resulting product was loaded on the LabChip GX Touch High sensitivity DNA chip.

Human DNA (NA12878) was fragmented using Kapa Frag module in two different workflows: in the first workflow (workflow 1), 10 ng human genomic DNA (NA12878) is taken into a fragmentation reaction, the reaction product is purified with Kapa Pure beads, and the entire eluted product is taken into the template-switching reaction without quantification. In the second workflow (workflow 2), a large amount of DNA is fragmented, cleaned up with 2× Kapa Pure beads, eluted in 10 mM Tris-HCl, and the DNA is first quantified with a Qubit to add exactly 10 ng fragmented DNA to the template-switching reaction. The template-switching reaction contains 200 U MMLV RT, reaction buffer, 1 mM dNTPs plus additional 10 mM complementary nucleotide to the individual TSO, or 5 mM of each complementary nucleotide to the TSO mixture. This means TSO-rC receives 10 mM dGTP in addition to the 1 mM dNTPs, whereas TSO-rG receives 10 mM dCTP in addition to the 1 mM dNTPs, whereas the TSO-rCrG combination receives 5 mM dGTP+5 mM dCTP+1 mM dNTPs. The reaction contains a TSO, either 500 mM TSO-rC, or 500 mM TSO-rG, or 250 mM TSO-rC+250 mM TSO-rG. The reactions were incubated for 10 min at 42° C. and cleaned up with 0.8× Kapa Pure beads. The product was eluted in Tris-HCl, which is taken into the first of two nested, multiplexed PCR reactions. The 361Plus (no tiling) Outer primer panel is used to amplify 137 targets. The product from the first PCR is cleaned up with Kapa Pure beads and the elute taken into the second, nested multiplexed PCR with the inner primer panel, as well as i5 and i7 primers to index the libraries. A final Kapa Pure bead clean-up is done after the second PCR. The libraries were pooled and 1.5 pM sequenced on the NextSeq-500 with 30% phiX spiked-in. FIG. 29 is a graph showing the on-target rates of 5N or 7N UMI-containing TSOs wherein the TSOs are TSO-rc, TSO-rG or TSO-rCrG using workflow 1 or workflow 2. FIG. 30 is a graph showing the on-target reads of 5N or 7N UMI-containing TSOs wherein the TSOs are TSO-rC, TSO-rG or TSO-rCrG using workflow 1 or workflow 2. The y-axis displays the number of reads. FIG. 31 is a graph showing the uniformity of 5N or 7N UMI-containing TSOs wherein the TSOs are TSO-rC, TSO-rG or TSO-rCrG using workflow 1 or workflow 2. FIG. 32 is a graph showing the genome equivalence recovery rate of 5N or 7N UMI-containing TSOs wherein the TSOs are TSO-rC, TSO-rG or TSO-rCrG using workflow 1 or workflow 2.

The TSO with 7N UMI performs equal or better than the TSO with 5N UMI. The combination of the TSO-rC and TSO-rG also performs better than the individual TSOs, with more than 70% of the amplicon product having an adapter added (FIG. 28).

ADDITIONAL EXEMPLARY EMBODIMENTS

One embodiment of the present disclosure is directed to a composition comprising: a double-stranded deoxyribonucleic acid (dsDNA) sequence comprising: a sense strand comprising, from 5' to 3', a sequence comprising a first adaptor sequence, a template sequence, and a second adaptor sequence, and an anti-sense strand comprising a sequence comprising a sequence complementary to the sequence of the sense strand (a), wherein the second adaptor sequence comprises a hybridization site for a template switching oligonucleotide (TSO). In another embodiment, the anti-sense strand of (b) comprises, from 5' to 3', a sequence comprising a reverse complement of the sequence of the sense strand (a). In another embodiment, the first adaptor sequence comprises between 1 and 5 nucleotides, inclusive of the endpoints. In another embodiment, the first adaptor sequence comprises three nucleotides. In another embodiment, the first adaptor sequence comprises a poly(G) sequence or a poly (C) sequence. In another embodiment, the second adaptor sequence comprises between 1 and 5 nucleotides, inclusive of the endpoints. In another embodiment, the second adaptor sequence comprises three nucleotides. In another embodiment, the second adaptor sequence comprises a poly(G) sequence or a poly (C) sequence. In another embodiment, the first adaptor sequence and the second adaptor sequence are not identical. In another embodiment, the hybridization site for the TSO comprises the poly(G) sequence or the poly (C) sequence. In another embodiment, the hybridization site for the TSO consists of the poly(G) sequence or the poly (C) sequence. In another embodiment, the template sequence comprises a fragmented DNA sequence. In another embodiment, the fragmented DNA sequence comprises a PCR product, a sheared DNA, or a repaired DNA. In another embodiment, the PCR product is a blunt-ended product or a product with blunted ends. In another embodiment, the sheared DNA comprises a mechanically or enzymatically sheared DNA. In another embodiment, the sheared DNA comprises genomic DNA. In another embodiment, the sheared DNA comprises a vector. In another embodiment, the sheared DNA comprises a natively sheared DNA. In another embodiment, the natively sheared DNA comprises a cell free DNA (cfDNA). In another embodiment, the repaired DNA has been enzymatically repaired to be double-stranded. In another embodiment, the TSO comprises a single-stranded deoxyribonucleic acid (ssDNA) sequence. In another embodiment, the TSO further comprises a secondary structure. In another embodiment, the secondary structure comprises a hairpin. In another embodiment, the ssDNA sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the TSO. In another embodiment, the ssDNA sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO. In another embodiment, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO are continuous. In another embodiment, the TSO comprises a hybridization site having at least 50% complementarity to the hybridization site of the second adaptor. In another embodiment, the hybridization site has 100% complementarity to the hybridization site of the second adaptor. In another embodiment, the hybridization site comprises a single-stranded nucleic acid sequence. In another embodiment, the single-stranded nucleic acid sequence comprises between 1 and 5 nucleotides, inclusive of the endpoints. In another embodiment, the single-stranded nucleic acid sequence comprises three nucleotides. In another embodiment, the single-stranded nucleic acid sequence is a DNA sequence. In another embodiment, the DNA sequence comprises a poly(G) sequence or a poly(C) sequence. In another embodiment, the single-stranded nucleic acid sequence is an RNA sequence. In another embodiment, the RNA sequence comprises a poly(G) sequence or a poly(C) sequence. In another embodiment, the ssDNA comprises a sequence having at least 50% identity or complementarity to a sequence of a primer, an adaptor, or a component of an array. In another embodiment, the ssDNA comprises a sequence having at least 50%, at least 55%, at least 60%, at least 65%, at least 70%, at least 75%, at least 80%, at least 85%, at least 90%, at least 95%, at least 97%, at least 99%, at least 100% or any percentage in between identity or complementarity to a sequence of a primer, an adaptor, or a component of an array. In another embodiment, the first adaptor sequence or the second adaptor sequence comprises a sequence of the TSO. In another embodiment, the first adaptor sequence or the second adaptor sequence comprises a sequence identical to a sequence of the ISO or a sequence complementary to a sequence of the TSO. In another embodiment, the first adaptor sequence comprises a sequence identical to a sequence of a first TSO or a sequence complementary to a sequence of the first TSO and the second adaptor sequence comprises a sequence identical to a sequence of a second TSO or a sequence complementary to a sequence of the second TSO, and wherein the first TSO and the second TSO are not identical. In another embodiment, the first adaptor sequence or the second adaptor sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the sequence of the TSO. In another embodiment, the first adaptor sequence or the second adaptor sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO. In another embodiment, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO are continuous. In another embodiment, the first adaptor sequence or the second adaptor sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the sequence of the first TSO or the second TSO, respectively. In another embodiment, the first adaptor sequence or the second adaptor sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the first TSO or the second TSO, respectively.

In another embodiment, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the first TSO or the second TSO, respectively, are continuous. In another embodiment, the sense strand comprises, from 5' to 3', a sequence comprising a first adaptor sequence, a template sequence, and a second adaptor sequence, wherein the first adaptor sequence comprises a sequence identical to the sequence of the TSO, a sequence identical to the sequence of a unique identifier (UID) sequence, a sample identifier (SID) sequence or a unique molecular identifier (UMI) sequence and the poly(G) sequence, and wherein the second adaptor sequence comprises a sequence complementary to the sequence of the TSO, a sequence complementary to the UID sequence, the SID sequence or the UMI sequence and the poly(C) sequence. In another embodiment, to sense strand comprises, from 5' to 3', a sequence comprising a first adaptor sequence, a template sequence, and a second adaptor sequence, wherein the first adaptor sequence comprises a sequence identical to the sequence of the TSO, a sequence identical to the sequence of a unique identifier (UID) sequence, a sample identifier (SID) sequence or a unique molecular identifier (UMI) sequence and the poly(C) sequence, and wherein the second adaptor sequence comprises a sequence complementary to the sequence of the TSO, a sequence complementary to the UID sequence, the SID sequence or the UMI sequence and the poly(G) sequence. In another embodiment, the TSO comprises one or more of a UID sequence, a SID sequence or a UMI sequence. In another embodiment, the UID sequence, the SID sequence or the UMI sequence comprises a random sequence. In another embodiment, the UID sequence, the SID sequence or the UMI sequence comprises a pre-determined sequence. In another embodiment, the UID sequence, the SID sequence or the UMI sequence comprises a sequence between 1 and 20 nucleotides, inclusive of the endpoints. In another embodiment, the UID sequence, the SID sequence or the UMI sequence comprises a sequence between 2 and 12 nucleotides, inclusive of the endpoints. In another embodiment, the UID sequence, the SID sequence or the UMI sequence comprises a sequence between 4 and 10 nucleotides, inclusive of the endpoints. In another embodiment, the UID sequence or the SID sequence comprises eight nucleotides. In another embodiment, the UMI sequence comprises or consists of seven nucleotides. In another embodiment, the UMI sequence comprises or consists of five nucleotides.

Another embodiment of the present disclosure is directed to a method of making the compositions described previously, comprising: contacting a template sequence and a polymerase under conditions sufficient to allow for terminal transferase activity, to produce an intermediate double-stranded deoxyribonucleic acid (dsDNA) sequence, wherein the intermediate dsDNA comprises the adaptor sequence at the 3' end of the sense strand and the antisense strand; contacting the intermediate dsDNA, the polymerase and at least one template switching oligonucleotide (TSO) under conditions sufficient to allow for DNA-dependent DNA polymerase activity, to produce the dsDNA. In another embodiment, the adaptor sequence at the 3' end of the sense strand and the antisense strand comprises a poly(G) sequence or a poly(C) sequence. In another embodiment, the adaptor sequence at the 3' end of the sense strand and the antisense strand comprises a poly(G) sequence. In another embodiment, the conditions sufficient to allow for terminal transferase activity or DNA-dependent DNA polymerase activity comprise a plurality of deoxynucleotides (dNTPs).

In another embodiment, the conditions sufficient to allow for terminal transferase activity comprise a plurality of dCTPs, a plurality of dGTPs, or a combination thereof. In another embodiment, the conditions sufficient to allow for terminal transferase activity comprise a combination of dCTPs and dGTPs. In another embodiment, the conditions sufficient to allow for DNA-dependent DNA polymerase activity comprise an incubation at temperatures from between 27° C. and 50° C., inclusive of the endpoints, for a period of between 2 and 20 minutes. In another embodiment, the conditions sufficient to allow for DNA-dependent DNA polymerase activity comprise an incubation at 42° C. for 10 minutes. In another embodiment, the conditions sufficient to allow for DNA-dependent DNA polymerase activity comprise an incubation at 42° C. for 5 minutes. In another embodiment, the polymerase comprises a reverse transcriptase. In another embodiment, the reverse transcriptase is a Moloney Murine Leukemia Virus Reverse Transcriptase (MMLV) reverse transcriptase. In another embodiment, the conditions sufficient to allow for DNA-dependent DNA polymerase activity comprise the co-factor $Mg^{2+}$. In another embodiment, the co-factor $Mg^{2+}$ is present at a concentration of between 20 and 40 mM. In another embodiment, the co-factor $Mg^{2+}$ is present at a concentration of between 24 and 36 mM. In another embodiment, a concentration of template DNA in (a) is between 0.1 ng and 100 ng, inclusive of the endpoints. In another embodiment, the concentration of template DNA in (a) is equal to or less than 0.1 ng, 1 ng, 10 ng or 100 ng.

Another embodiment of the present disclosure is directed to a method of making a DNA fragment library comprising: contacting any of the compositions described previously herein, a first forward primer, a first reverse primer, a polymerase and a plurality of dNTPs, and amplifying a first portion of the composition under conditions sufficient for the amplification to proceed, thereby producing a first amplification product. In another embodiment, the first forward primer and the first reverse primer hybridize to the sense strand of the composition. In another embodiment, the first forward primer and the first reverse primer hybridize to the antisense strand of the composition. In another embodiment, the first forward primer hybridizes with a sequence within the first adaptor sequence. In another embodiment, the first forward primer hybridizes with a portion of a sequence identical to a sequence of the TSO. In another embodiment, the first reverse primer hybridizes with a sequence within the second adaptor sequence. In another embodiment, the first reverse primer hybridizes with a portion of a sequence identical to a sequence of the TSO. In another embodiment, the first reverse primer hybridizes with a sequence within the template sequence. In another embodiment, the method further comprises: contacting the first amplification product of claim 74, a second forward primer, a second reverse primer, a polymerase and a plurality of dNTPs, and amplifying the first amplification product under conditions sufficient for the amplification to proceed, thereby producing a second amplification product. In another embodiment, the second forward primer hybridizes with a sequence within the first adaptor sequence. In another embodiment, the second forward primer hybridizes with a sequence within a sequence identical to a sequence of the TSO. In another embodiment, the second reverse primer hybridizes with a sequence within the second adaptor sequence. In another embodiment, the second reverse primer hybridizes with a sequence within a sequence identical to a sequence of the TSO. In another embodiment, the second reverse primer hybridizes with a sequence within the template sequence. In another embodiment, the first forward primer and first reverse primer form a first primer pair, wherein the second forward primer and second reverse primer form a second primer pair, wherein the first primer pair contacted any of the composition previously described herein, and wherein the second primer pair contact the first amplification product. In another embodiment, a forward primer or a reverse primer comprises a UID sequence or a SID sequence. In another embodiment, the UID sequence or the SID sequence comprises a random sequence. In another embodiment, the UID sequence or the SID sequence comprises a pre-determined sequence. In another embodiment, the UID sequence or the SID sequence a sequence between 1 and 20 nucleotides, inclusive of the endpoints. In another embodiment, the UID sequence or the SID sequence comprises a sequence between 2 and 12 nucleotides, inclusive of the endpoints. In another embodiment, the UID sequence or the SID sequence comprises a sequence between 4 and 10 nucleotides, inclusive of the endpoints. In another embodiment, the UID sequence or the SID sequence comprises eight nucleotides. In another embodiment, the UID sequence or the SID sequence of the forward or reverse primer and the UID sequence the SID sequence or the UMI sequence of the TSO are not identical.

Another embodiment of the present disclosure is directed to a composition comprising a single-stranded deoxyribonucleic acid (ssDNA), the ssDNA comprising, from 5' to 3', a template sequence and an adaptor sequence, wherein the adaptor sequence comprises a hybridization site for a TSO. In another embodiment, the adaptor sequence comprises between 1 and 5 nucleotides, inclusive of the endpoints. In another embodiment, the adaptor sequence comprises three nucleotides. In another embodiment, the adaptor sequence comprises a poly(C) sequence or a poly(G) sequence. In another embodiment, the hybridization site for the TSO comprises the poly(C) sequence or the poly(G) sequence. In another embodiment, the template sequence comprises a fragmented DNA sequence. In another embodiment, the fragmented DNA sequence comprises a PCR product, a sheared DNA, or a repaired DNA. In another embodiment, the PCR product is a blunt-ended product or a product with blunted ends. In another embodiment, the sheared DNA comprises a mechanically or enzymatically sheared DNA. In another embodiment, the sheared DNA comprises genomic DNA. In another embodiment, the sheared DNA comprises a vector. In another embodiment, the sheared DNA comprises a natively sheared DNA. In another embodiment, the natively sheared DNA comprises a cell free DNA (cfDNA). In another embodiment, the repaired DNA has been enzymatically repaired to be double-stranded. In another embodiment, the TSO comprises a single-stranded deoxyribonucleic acid (ssDNA) sequence. In another embodiment, the TSO further comprises a secondary structure. In another embodiment, the secondary structure comprises a hairpin. In another embodiment, the ssDNA sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the TSO. In another embodiment, the ssDNA sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO. In another embodiment, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO are continuous. In another embodiment, the TSO comprises a hybridization site having at least 50% complementarity to the hybridization site of the adaptor. In another embodiment, the hybridization site has 100% complementarity to the hybridization site of the adaptor. In another embodiment, the hybridization site comprises a single-stranded nucleic acid sequence. In another embodiment, the single-stranded nucleic acid sequence comprises between 1 and 5 nucleotides, inclusive of the endpoints. In another embodiment, the single-stranded nucleic acid sequence comprises three nucleotides. In another embodiment, the single-stranded nucleic acid sequence is a DNA sequence. In another embodiment, the DNA sequence comprises a poly(G) sequence or a poly(C) sequence. In another embodiment, the single-stranded nucleic acid sequence is an RNA sequence. In another embodiment, the RNA sequence comprises a poly(G) sequence or a poly(C) sequence. In another embodiment, the ssDNA comprises a sequence having at least 50% identity or complementarity to a sequence of a primer, an adaptor, or a component of an array. In another embodiment, the ssDNA comprises a sequence having at least 50%, at least 55%, at least 60%, at least 65%, at least 70%, at least 75%, at least 80%, at least 85%, at least 90%, at least 95%, at least 97%, at least 99%, at least 100% or any percentage in between identity or complementarity to a sequence of a primer, an adaptor, or a component of an array. In another embodiment, the adaptor sequence comprises a sequence of the TSO. In another embodiment, the adaptor sequence comprises a sequence identical to a sequence of the TSO or a sequence complementary to a sequence of the TSO. In another embodiment, the adaptor sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the sequence of the TSO. In another embodiment, the adaptor sequence comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO. In another embodiment, the at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 nucleotides of the TSO are continuous. In another embodiment, the ssDNA comprises, from 5' to 3', a sequence comprising a template sequence and an adaptor sequence, and wherein the adaptor sequence comprises a sequence complementary to the sequence of the TSO, a sequence complementary to the UID sequence and the poly(C) sequence. In another embodiment, the ssDNA comprises, from 5' to 3', a sequence comprising a template sequence and an adaptor sequence, and wherein the adaptor sequence comprises a sequence complementary to the sequence of the TSO, a sequence complementary to the UID sequence and the poly(G) sequence. In another embodiment, the TSO comprises a UID sequence, a SID sequence or a UMI sequence. In another embodiment, the UID sequence, the SID sequence or the UMI sequence comprises a random sequence. In another embodiment, the UID sequence, the SID sequence or the UMI sequence comprises a pre-determined sequence. In another embodiment, the UID sequence, the SID sequence or the UMI sequence comprises a sequence between 1 and 20 nucleotides, inclusive of the endpoints. In another embodiment, the UID sequence, the SID sequence or the UMI sequence comprises a sequence between 2 and 12 nucleotides, inclusive of the endpoints. In another embodiment, the UID sequence, the SID sequence or the UMI sequence comprises a sequence between 4 and 10 nucleotides, inclusive of the endpoints. In another embodiment, the UID sequence or the SID sequence comprises eight nucleotides. In another embodiment, the UMI sequence comprises seven nucleotides. In another embodiment, the UMI sequence comprises five nucleotides.

Yet another embodiment of the present disclosure is directed to a method of making the ssDNA of any of the previously describe compositions described herein, comprising: denaturing a template sequence to produce a denatured template, contacting the denatured template, a primer that hybridizes with a sequence of the denatured template, and a polymerase under conditions sufficient to allow for an initial primer extension activity followed by a second terminal transferase activity, to produce an intermediate ssDNA sequence, wherein the intermediate ssDNA comprises an adaptor sequence at a 3' end; contacting the intermediate ssDNA, the polymerase and a TSO under conditions sufficient to allow for DNA-dependent DNA polymerase activity, to produce a ssDNA composition. In another embodiment, the adaptor sequence at the 3' end of the sense strand and the antisense strand comprises a poly (G) sequence or a poly(C) sequence.

(Original) The method of claim 144, wherein the adaptor sequence at the 3' end of the sense strand and the antisense strand comprises a poly(G) sequence. In another embodiment, the method further comprises contacting the ssDNA composition of (c) and an exonuclease under conditions sufficient to allow for nuclease activity, to remove the primer of (b) and/or the TSO of (c), and removing the exonuclease or a nuclease activity thereof to produce an isolated ssDNA composition. In another embodiment, the removing step comprises heating the ssDNA composition and the exonuclease of (c). In another embodiment, the polymerase comprises a thermostable polymerase. In another embodiment, the polymerase comprises a high-fidelity polymerase. In another embodiment, the polymerase comprises a sequence of a Pfu polymerase, a sequence of a KOD polymerase or a combination thereof. In another embodiment, the polymerase comprises an N-terminal domain, an exonuclease domain, and a thumb domain a KOD polymerase and a palm domain and a fingers domain of a Pfu polymerase. In another embodiment, the polymerase is encoded by the nucleic acid sequence of SEQ ID NO: 1, 3, 5, or 7 or wherein the polymerase is encoded by the amino acid sequence of SEQ ID NO: 2, 4, 6, or 8.

Another embodiment of the present disclosure is directed to a method of making a DNA fragment library comprising: contacting the ssDNA composition, as described previously herein, or the isolated ssDNA composition, as described previously herein, a forward primer, a reverse primer, a polymerase and a plurality of dNTPs under conditions sufficient for amplification of at least one ssDNA or a portion thereof, wherein the ssDNA comprises a first amplification product and wherein a second amplification product comprise a second DNA strand, wherein the second DNA strand is complementary to the ssDNA and/or the first amplification product. In another embodiment, the forward primer hybridizes with a sequence within the first adaptor sequence. In another embodiment, the forward primer hybridizes with a sequence within a sequence identical to a sequence of the TSO. In another embodiment, the reverse primer hybridizes with a sequence within the template sequence. In another embodiment, the reverse primer comprises a linking sequence and a UID sequence or a SID sequence. In another embodiment, the linking sequence comprises a sequence having at least 50% identity or complementarity to a sequence of a primer, an adaptor, or a component of an array. In another embodiment, the linking sequence comprises a sequence having at least 50%, 55%, 60%, 65%, 70%, 75%, 80%, 85%, 90%, 95%, 97%, 99%, 100% or any percentage in between identity or complementarity to a sequence of a primer, an adaptor, or a component of an array. In another embodiment, the UID sequence or the SID sequence comprises a random sequence. In another embodiment, the UID sequence or the SID sequence comprises a pre-determined sequence. In another embodiment, the UID sequence or the SID sequence comprises a sequence between 1 and 20 nucleotides, inclusive of the endpoints. In another embodiment, the UID sequence or the SID sequence comprises a sequence between 2 and 12 nucleotides, inclusive of the endpoints. In another embodiment, the UID sequence or the SID sequence comprises a sequence between 4 and 10 nucleotides, inclusive of the endpoints. In another embodiment, the UID sequence or the SID sequence comprises eight nucleotides. In another embodiment, the UID sequence or the SID sequence of a primer and the UID sequence, the SID sequence or the UMI sequence of the TSO are not identical. In another embodiment, the first amplification product comprises a sequence complementary to a sequence of the reverse primer. In another embodiment, the reverse primer comprises a UID sequence or a SID sequence and wherein the first amplification product comprises a sequence complementary to the UID sequence or the SID sequence. In another embodiment, the reverse primer comprises a linking sequence and wherein the first amplification product comprises a sequence complementary to the linking sequence.

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER EMBODIMENTS

While particular embodiments of the disclosure have been illustrated and described, various other changes and modifications can be made without departing from the spirit and scope of the disclosure. The scope of the appended claims includes all such changes and modifications that are within the scope of this disclosure.

The invention claimed is:

1. A composition comprising:
   a double-stranded deoxyribonucleic acid (dsDNA) sequence comprising:
   (a) a sense strand comprising, from 5' to 3', a sequence comprising a first adaptor sequence, a template sequence, and a second adaptor sequence, and
   (b) an anti-sense strand comprising a sequence comprising a sequence complementary to the sequence of the sense strand (a),
   wherein the second adaptor sequence comprises a hybridization site for a template switching oligonucleotide (TSO), and
   wherein either:
      (1) the first adaptor sequence comprises: (i) a sequence identical to the sequence of the TSO; (ii) a sequence identical to the sequence of a unique identifier (UID) sequence, a sample identifier (SID) sequence, or a unique molecular identifier (UMI) sequence; and (iii) a poly(G) sequence; and the second adaptor sequence comprises: (i) a sequence complementary to the sequence of the TSO; (ii) a sequence complementary to the UID sequence, the SID sequence, or the UMI sequence; and (iii) a poly(C) sequence; or
      (2) the first adaptor comprises: (i) a sequence identical to the sequence of the TSO; (ii) a sequence identical to the sequence of a UID sequence, a SID sequence, or a UMI sequence; and (iii) a poly(C) sequence; and the second adaptor sequence comprises: (i) a sequence complementary to the sequence of the TSO; (ii) a sequence complementary to the UID sequence, the SID sequence, or the UMI sequence; and (iii) a poly(G) sequence.

2. The composition of claim 1, wherein the anti-sense strand of (b) comprises, from 5' to 3', a sequence comprising a reverse complement of the sequence of the sense strand (a).

3. The composition of claim 1, wherein the first adaptor sequence and/or the second adaptor sequence comprises between 1 and 5 nucleotides, inclusive of the endpoints.

4. The composition of claim 1, wherein the hybridization site for the TSO comprises the poly(G) sequence or the poly(C) sequence.

5. The composition of claim 1, wherein the template sequence comprises a fragmented DNA sequence.

6. The composition of claim 5, wherein the fragmented DNA sequence comprises a PCR product, a sheared DNA, or a repaired DNA.

7. The composition of claim 1, further comprising a template switching oligonucleotide (TSO).

8. The composition of claim 7, wherein the TSO comprises a single-stranded deoxyribonucleic acid (ssDNA) sequence.

9. The composition of claim 8, wherein the TSO further comprises a secondary structure.

10. The composition of claim 9, wherein the secondary structure comprises a hairpin.

11. The composition of claim 8, wherein the ssDNA sequence comprises at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or any percentage in between of the TSO.

12. The composition of claim 8, wherein the TSO comprises a hybridization site having at least 50% complementarity to the hybridization site of the second adaptor.

13. The composition of claim 12, wherein the hybridization site of the TSO comprises a single-stranded nucleic acid sequence.

14. The composition of claim 8, wherein the ssDNA comprises a sequence having at least 50% identity or complementarity to a sequence of a primer, an adaptor, or a component of an array.

15. The composition of claim 14, wherein the ssDNA comprises a sequence having at least 50%, at least 55%, at least 60%, at least 65%, at least 70%, at least 75%, at least 80%, at least 85%, at least 90%, at least 95%, at least 97%, at least 99%, 100% or any percentage in between identity or complementarity to a sequence of a primer, an adaptor, or a component of an array.

16. The composition of claim 1, wherein
   (1) the first adaptor sequence comprises: (i) a sequence identical to the sequence of the TSO; (ii) a sequence identical to the sequence of a UID sequence, a SID sequence, or a UMI sequence; and (iii) a poly(G) sequence; and the second adaptor sequence comprises: (i) a sequence complementary to the sequence of the TSO; (ii) a sequence complementary to the UID sequence, the SID sequence, or the UMI sequence; and (iii) a poly(C) sequence.

17. The composition of claim 1, wherein
   (2) the first adaptor sequence comprises: (i) a sequence identical to the sequence of the TSO; (ii) a sequence identical to the sequence of a UID sequence, a SID sequence, or a UMI sequence; and (iii)a poly(C) sequence; and the second adaptor sequence comprises: (i) a sequence complementary to the sequence of the TSO; (ii) a sequence complementary to the UID sequence, the SID sequence, or the UMI sequence; and (iii) a poly(G) sequence.

18. The composition of claim 7, wherein the TSO comprises one or more of a UID sequence, a SID sequence, or a UMI sequence.

19. The composition of claim 18, wherein the UID sequence, the SID sequence, or the UMI sequence comprises a random sequence.

20. The composition of claim 18, wherein the UID sequence, the SID sequence, or the UMI sequence comprises a pre-determined sequence.

21. The composition of claim 19, wherein the UID sequence, the SID sequence, or the UMI sequence comprises a sequence between 1 and 20 nucleotides, inclusive of the endpoints.

22. A method of making the composition of claim 1, comprising:
   (a) contacting a template sequence and a polymerase under conditions sufficient to allow for terminal transferase activity, to produce an intermediate double-stranded deoxyribonucleic acid (dsDNA) sequence, wherein the intermediate dsDNA comprises the adaptor sequence at the 3' end of the sense strand and the antisense strand;
   (b) contacting the intermediate dsDNA, the polymerase and at least one template switching oligonucleotide (TSO) under conditions sufficient to allow for DNA-dependent DNA polymerase activity, to produce the dsDNA of claim 1.

23. The method of claim 22, wherein the adaptor sequence at the 3' end of the sense strand and the antisense strand comprises a poly(G) sequence or a poly(C) sequence.

24. The method of claim 22, wherein the adaptor sequence at the 3' end of the sense strand and the antisense strand comprises a poly(G) sequence.

25. The method of claim 22, wherein the conditions sufficient to allow for terminal transferase activity or DNA-dependent DNA polymerase activity comprise a plurality of deoxynucleotides (dNTPs).

26. The method of claim 22, wherein the conditions sufficient to allow for terminal transferase activity comprise a plurality of dCTPs, a plurality of dGTPs, or a combination thereof.

27. The method of claim 22, wherein the conditions sufficient to allow for DNA-dependent DNA polymerase activity comprise an incubation at temperatures from between 27° C. and 50° C., inclusive of the endpoints, for a period of between 2 and 20 minutes.

28. The method of claim 22, wherein the polymerase comprises a reverse transcriptase.

29. The method of claim 28, wherein the reverse transcriptase is a Moloney Murine Leukemia Virus Reverse Transcriptase (MMLV) reverse transcriptase.

30. The method of claim 29, wherein the conditions sufficient to allow for DNA-dependent DNA polymerase activity comprise the co-factor $Mg^{2+}$.

31. The method of claim 30, wherein the co-factor $Mg^{2+}$ is present at a concentration of between 20 and 40 mM.

32. The method of claim 22, wherein a concentration of template DNA in (a) is between 0.1 ng and 100 ng, inclusive of the endpoints.

33. A method of making a DNA fragment library comprising:
   contacting the composition of claim 1, a first forward primer, a first reverse primer, a polymerase and a plurality of dNTPs, and
   amplifying a first portion of the composition under conditions sufficient for the amplification to proceed,
   thereby producing a first amplification product.

34. The method of claim 33, wherein the first forward primer and the first reverse primer hybridize to the sense strand or the antisense strand of the composition.

35. The method of claim 33, wherein the first forward primer hybridizes with a sequence within the first adaptor sequence.

36. The method of claim 33, wherein the first forward primer hybridizes with a portion of a sequence identical to a sequence of the TSO.

37. The method of claim 33, wherein the first reverse primer hybridizes with a sequence within the second adaptor sequence.

38. The method of claim 33, wherein the first reverse primer hybridizes with a portion of a sequence complementary to a sequence of the TSO.

39. The method of claim 33, wherein the first reverse primer hybridizes with a sequence within the template sequence.

40. The method of claim 33, further comprising:
   contacting the first amplification product of claim 33, a second forward primer, a second reverse primer, a polymerase and a plurality of dNTPs, and
   amplifying the first amplification product under conditions sufficient for the amplification to proceed,
   thereby producing a second amplification product.

41. The method of claim 40, wherein the second forward primer hybridizes with a sequence within the first adaptor sequence.

42. The method of claim 40, wherein the second forward primer hybridizes with a sequence within a sequence identical to a sequence of the TSO.

43. The method of claim 40, wherein the second reverse primer hybridizes with a sequence within the second adaptor sequence.

44. The method of claim 40, wherein the second reverse primer hybridizes with a sequence within a sequence complementary to a sequence of the TSO.

45. The method of claim 40, wherein the second reverse primer hybridizes with a sequence within the template sequence.

46. The method of claim 40, wherein the first forward primer and first reverse primer form a first primer pair, wherein the second forward primer and second reverse primer form a second primer pair, wherein the first primer pair contacted the composition of claim 1 and wherein the second primer pair contact the first amplification product.

47. The method of claim 33, wherein a forward primer or a reverse primer comprises a UID sequence or a SID sequence.

48. The method of claim 47, wherein the UID sequence or the SID sequence comprises a random sequence.

49. The method of claim 47, wherein the UID sequence or the SID sequence comprises a pre-determined sequence.

50. The method of claim 48, wherein the UID sequence or the SID sequence a comprises sequence between 1 and 20 nucleotides, inclusive of the endpoints.

* * * * *